United States Patent
Bielinski et al.

(10) Patent No.: US 8,975,061 B2
(45) Date of Patent: Mar. 10, 2015

(54) REGULATION OF TOXIN AND ANTITOXIN GENES FOR BIOLOGICAL CONTAINMENT

(75) Inventors: Vincent A. Bielinski, San Diego, CA (US); Nicholas Bauman, San Diego, CA (US); Kate Lyons Boyd, Encinitas, CA (US); Srividya Akella, San Diego, CA (US); Stanley Bower, San Diego, CA (US); Paul G. Roessler, Bonita Springs, FL (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/536,345

(22) Filed: Jun. 28, 2012

(65) Prior Publication Data
US 2013/0023035 A1   Jan. 24, 2013

Related U.S. Application Data

(60) Provisional application No. 61/503,306, filed on Jun. 30, 2011.

(51) Int. Cl.
*C12N 1/20* (2006.01)
*C12N 15/74* (2006.01)
*C12N 1/38* (2006.01)
*C12N 1/12* (2006.01)

(52) U.S. Cl.
CPC   *C12N 15/74* (2013.01); *C12N 1/20* (2013.01); *C12N 1/38* (2013.01); *C12N 1/12* (2013.01)
USPC ...................................... 435/252.3

(58) Field of Classification Search
None
See application file for complete search history.

(56) References Cited

U.S. PATENT DOCUMENTS

| | | | | |
|---|---|---|---|---|
| 5,455,167 | A | 10/1995 | Voelker et al. | 435/172.3 |
| 5,654,495 | A | 8/1997 | Voelker et al. | 800/250 |
| 5,851,796 | A | 12/1998 | Schatz | 435/69.1 |
| 6,337,208 | B1 | 1/2002 | Graupner | 435/320.1 |
| 7,135,290 | B2 | 11/2006 | Dillon | 435/6 |
| 7,183,097 | B1 | 2/2007 | Gerdes et al. | 435/252.3 |
| 7,595,185 | B2 | 9/2009 | Gerdes et al. | 435/252.3 |
| 7,595,186 | B2 | 9/2009 | Gerdes et al. | 435/252.3 |
| 2008/0206840 | A1 | 8/2008 | Gerdes et al. | 435/252.3 |
| 2009/0124012 | A1 | 5/2009 | Nikolsky et al. | 435/455 |
| 2009/0215179 | A1 | 8/2009 | Gressel et al. | 435/471 |
| 2009/0298143 | A1 | 12/2009 | Roessler et al. | 435/134 |
| 2010/0035346 | A1* | 2/2010 | Inouye et al. | 435/471 |
| 2010/0234287 | A1 | 9/2010 | Inouye et al. | 514/12 |
| 2010/0304432 | A1 | 12/2010 | O'Keefe et al. | 435/69.1 |

FOREIGN PATENT DOCUMENTS

| | | | | |
|---|---|---|---|---|
| WO | WO 99/58652 | 11/1999 | ............ | C12N 15/00 |
| WO | WO-2004/113498 A2 | 12/2004 | | |
| WO | WO 2007/136762 | 11/2007 | ............ | C12N 1/00 |
| WO | WO 2008/119082 | 10/2008 | ............ | C12P 7/64 |
| WO | WO 2009/009391 | 1/2009 | ............ | C07C 67/08 |
| WO | WO 2009/076559 | 6/2009 | ............ | C12P 7/64 |
| WO | WO 2009/140701 | 11/2009 | ............ | C12N 15/87 |
| WO | WO 2010/027516 | 3/2010 | ............ | C12N 15/74 |
| WO | WO 2010/044960 | 4/2010 | ............ | C12P 7/06 |
| WO | WO 2010/075483 | 7/2010 | ............ | C12N 9/16 |
| WO | WO 2010/118410 | 10/2010 | ............ | C12N 1/20 |
| WO | WO 2010/126891 | 11/2010 | ............ | C12P 7/64 |
| WO | WO 2011/008535 | 1/2011 | ............ | C12P 7/64 |
| WO | WO 2011/019858 | 2/2011 | ............ | C12N 1/13 |
| WO | WO 2012/006307 | 1/2012 | ............ | C12N 1/02 |
| WO | WO 2013/003597 | 1/2013 | ............ | C12N 15/31 |

OTHER PUBLICATIONS

Geerts et al., "Inducible expression of heterologous genes targeted to a chromosomal platform in the cyanobacterium *Synechococcus* sp. PCC 7942", Microbiology (1995), 141,831-841.*
Altschul, S., et al. (1997), "Gapped BLAST and PSI-BLAST: a new generation of protein database search programs", *Nucleic Acids Research*, 25(17): 3389-3402.
Anantharaman, V., et al. (2003), "New connections in the prokaryotic toxin-antitoxin network: relationship with the eukaryotic nonsense-mediated RNA decay system" *Genome Biology*, 4:R81.
Anderson, S., et al., (1991), "Light-activated heterotrophic growth of the cyanobacterium *Synechocystis* sp. strain PCC 6803: a blue-light-requiring process", *Journal of Bacteriology*, 173(9): 2761-2767.
Andreev, D., et al., (2008), "The bacterial toxin RelE induces specific mRNA cleavage in the A site of the eukaryotic ribosome", *RNA*, 14: 233-239.
Armalyté, J., et al., (2012), "Characterization of *Escherichia coli* dinJ-yafQ toxin-antitoxin system using insights from mutagenesis data", *Journal of Bacteriology* 194: 1523-1532.
Audoly, G., et al., (2011), "Effect of rickettsial toxin vapC on its eukaryotic host", *PLoS ONE*, 6(10): e26528.
Barnard, A., et al., (2004), "Regulation at complex bacterial promoters: how bacteria use different promoter organizations to produce different regulatory outcomes", *Current Opinion in Microbiology*, 7: 102-108.
Bertrand, K., et al., (1984), "Construction of a single-copy promoter vector and its use in analysis of regulation of the transposon Tn10 tetracycline resistance determinant", *Journal of Bacteriology*, 158: 3: 910-919.
Bettiga, M., et al., (2009), "Arabinose and xylose fermentation by recombinant *Saccharomyces cervisiae* expressing a fungal pentose utilization pathway", *Microbial Cell Factories*, 8:40.
Blancato, V., et al., (2008), "Transcriptional regulation of the citrate gene cluster of *Enterococcus faecalis* involves the GntR family translational Activator CitO", Journal of Bacteriology, 190(22): 7419-7430.

(Continued)

*Primary Examiner* — Suzanne M Noakes
(74) *Attorney, Agent, or Firm* — Harness, Dickey & Pierce, P.L.C.

(57) ABSTRACT

The present invention relates to the regulation of a toxin and/or antitoxin genes in a genetically engineered microorganism, such as cyanobacterial or eukaryotic algal strains, in particular for preventing unintentional and/or uncontrolled spread of the microorganisms. The present invention also includes methods of controlling the growth and/or survival of the engineered microorganism

24 Claims, 9 Drawing Sheets
(2 of 9 Drawing Sheet(s) Filed in Color)

(56) References Cited

OTHER PUBLICATIONS

Brautaset, T., et al., (2009), "Positively regulated bacterial expression systems", *Microbial Biotechology*, 2(1): 15-30.
Bukowski, M., et al., (2011), "Prokaryotic toxin-antitoxin systems—the role in bacterial physiology and application in molecular biology", *Acta Biochimica Polonica*, 58(1): 1-9.
Carrasco, C., et al., (1994), "*Anabaena* xisF gene encodes a developmentally regulated site-specific recombinase", *Genes & Development*, 8: 74-83.
Castruita, M., et al. (2011), "Systems biology approach in *Chlamydomonas* reveals connections between copper nutrition and multiple metabolic steps[C][W][OA]", *The Plant Cell*, 23: 1273-1292.
Cataudella, I., et al. (2012), "Conditional cooperativity in toxin-antitoxin regulation prevents random toxin activation and promotes fast translational recovery", *Nucleic Acids Research*, 40(14): 6424-6434.
Chang, J., et al., (2009), "Identification of a pair of toxin-antitoxin (TA) gene in the chromosome of cyanobacteria *Synechocystis* sp. PCC6803", *Microbiology*; Abstract only.
Christensen-Dalsgaard, M., et al., (2008), "Translation affects YoeB and MazF messenger RNA interfase activities by different mechanisms", *Nucleic Acids Research*, 36(20): 6472-6481.
Christensen-Dalsgaard, M., et al., (2010), "Three new RelE-homologous mRNA interferases of *Escherichia coli* differentially induced by environment stresses", *Molecular Microbiology*, 75(2): 333-348.
Christoffersen, C., et al. (2001), "Regulatory architecture of the iron-regulated fepD-ybdA bidirectional promoter region in *Escherichia coli*", *Journal of Bacteriology*, 183(6), 2059-2070.
Coll, N., et al., (2010), *Arabidopsis* type I metacaspases control cell death, *Science*, 330: 1393-1397.
Contreras, A., et al., (1991), "Conditional-suicide containment system for bacteria which mineralize aromatics", *Applied and Environmental Microbiology*, 57(5): 1504-1508.
Condon, C., et al., (2006), "Shutdown decay of mRNA", *Molecular Microbiology*, 61(3): 573-583.
De La Cueva-Mendez, G., et al., (2003), "Regulatable killing of eukaryotic cells by the prolaryotic proteins kid and kis", *The EMBO Journal* 22(2): 246-251.
Diago-Navarro, E., et al., (2010), "ParD toxin-antitoxin system of plasmid R1—basic contributions, biotechnological applications and relationships with closely-related toxin-antitoxin systems", *FEBS Journal*, 277: 3097-3117.
Engelberg-Kulka, H., et al., (2006), "Bacterial programmed cell death and multicellular behavior in bacteria", *PloS Genetics*, 2(10): e135.
Fico, S., et al., (2006), "TasA-tasB, a new putative toxin-antitoxin (TA) system from *Bacillus thuringiensis* pGII plasmid is a widely distributed composite maze-doc TA system" *BMC Genomics*, 7: 259.
Ferrante, P. et al. (2008), "An optimized, chemically regulated gene expression system for *Chlamydomonas*", *PloS ONE*, 3(9): e3200.
Georg, J., et al. (2009), "Evidence for a major role of antisense RNAs in cyanobacterial gene regulation", *Molecular Systems Biology* 5: 305.
Giacalone, M., et al. (2006), "Toxic protein expression in *Escherichia coli* using a rhamnose-based tightly regulated and tunable promoter system", *Bio Techniques*, 40: 355-364.
Gibson, D., et al. (2009), "Enzymatic assembly of DNA molecules up to several hundred kilobases", *Nature Methods*, 6(5): 343-345.
Gotfredsen, G., et al. (1998), "The *Escherichia coli* relBE genes belong to a new toxin-antitoxin gene family", *Molecular Microbiology*, 29(4): 1065-1076.
Guzman, L., et al. (1995) "Tight regulation, modulation, and high-level expression by vectors containing the arabinose $P_{BAD}$ promoter", *Journal of Bacteriology*, 177(14): 4121-4130.
Halvorsen, E., et al., (2011), "Txe, an endoribonuclease of the enterococcal axe-txe toxin-antitoxin system, cleaves mRNA and inhibits protein synthesis", *Microbiology*, 157: 387-397.
Henikoff, S., et al. (1992), "Amino acid substitution matrices from protein blocks", *Proc. Natl. Acad. Sci USA*, 89:10915-10919.

Holčik, M., et al., (1997), "Conditionally lethal genes associated with bacterial plasmids", *Microbiology*, 143: 3403-3416.
Hurley, J., et al., (2011), "Bacterial toxin RelE mediates frequent codon-independent mRNA cleavage from the 5' end of coding regions in vivo", *the Journal of Biological Chemistry*, 286(17): 14770-14778.
International Search Report for PCT/US2012/044654 dated Sep. 10, 2012.
Jiang, Q., et al., (2010), "Genome-wide comparative analysis of metacaspases in unicellular and filamentous cyanobacteria", *BMC Genomics*, 11: 198.
Jiwaji, M., et al. (2008), "A broad host range reporter plasmid for the analysis of divergent promoter regions", *South African Journal of Science*, 104: 305-307.
Karlin, S., et al., (1990), "Methods for assessing the statistical significance of molecular sequence features by using general scoring schemes", *Proc. Natl. Acad. Sci. USA*, 87: 2264-2268.
Khlebnikov, A., et al. (2000), "Regulatable arabinose-inducible gene expression system with consistent control in all cells of a culture", *Journal of Bacteriology*, 182(24): 7029-7034.
Khlebnikov, A., et al. (2001), "Homogeneous expression of the $P_{BAD}$ promoter in *Escherichia coli* by constitutive expression of the low-affinity high capacity AraE transporter" *Microbiology*, 147: 3421-3247.
Klemm, P., et al. (1995), "A stochastic killing system for biological containment of *Escherichia coli*", *Applied and Environmental Microbiology*, 61(2): 481-486.
Knudson, S.M., et al., (1991) "Development of efficient suicide mechanisms for biological containment of bacteria", *Applied and Envornmnemtal Microbiology*, 57(1): 85-92.
Knudson, S.M., et al., (1995), "Development and testing of improved suicide functions for biological containment of bacteria", *Applied and Environmental Microbiology*, 61(3): 985-991.
Koksharova, O.A., et al., (2002), "Genetic tools for cyanobacteria", *Appl Microbiol Biotechnol*, 58: 123-137.
Kong, W., et al., (2008), "Regulated programmed lysis of recombinant *Salmonella* in host tissues to release protective antigens and confer biological containment", *PNAS*, 105(27): 9361-9366.
Kretzschmar, U., et al. (2010), "Transcriptional regulation of the acetyl-CoA synthetase gene acsA in *Pseudomonas aeruginosa*", *Arch Microbiol*, 192: 685-690.
Kristoffersen, P., et al. (2000), "Bacterial toxin-antitoxin gene system as containment control in yeast cells" *Applied and Environmental Microbiology*, 66(12): 5524-5526.
La Fontaine, S., et al. (2002), "Copper-dependent iron assimilation pathway in the model photosynthetic Eukaryote *Chlamydomonas reinhardtii*", *Eukaryotic Cell*, 1(5): 736-757.
Lloyd, G., et al. (2008), "Transcription initiation in the *Escherichia coli* K-12 mall-malX intergenic region and the role of the cyclic AMP receptor protein", *FEMS Microbiol Lett*, 288: 250-257.
Magnuson, R., et al., (1996), "Autoregulation of the plasmid addiction operon of Bacteriophage P1", *The Journal of Biological Chemistry*, 271(31), 18705-18710.
Makarova, K., et al. (2009), "Comprehensive comparative-genomic analysis of type 2 toxin-antitoxin systems and related mobile stress response systems in prokaryotes", *Biology Direct*, 4:19.
Mazzoni, C., et al., (2008), "Caspase-dependent apoptosis in yeast", *Biochimica et Biophysica Acta*, 1783: 1320-1327.
Méndez-Alvarez, S., et al. (1994), "Transformation of chlorobium limicola by a plasmid that confers the ability to utilize thiosulfate" *Journal of Bacteriology*,176 (23):7395-7397.
Miller, R., et al. (2010), "Changes in transcript abundance in *Chlamydomonas reinhardtii* following nitrogen deprivation predict diversion of metabolism", *Plant Physiology*, 154: 1737-1752.
Morby, A., et al. (1993), "SmtB is a metal-dependent repressor of the cyanobacterial metallothionein gene smtA: identification of a Zn inhibited DNA-protein complex", Nucleic Acids Research, 21(4): 921-925.
Mortazavi, A., et al. (2008), "Mapping and quantifying mammalian transcriptomes by RNA-Seq", *Nature Methods*, 5(7): 621-628.
Moseley, J., et al., (2006), "Genome-based approaches to understanding phosphorus deprivation responses and PSR1 control in *Chlamydomonas reinhardtii*", *Eukaryotic Cell*, 5(1): 26-44.

(56) References Cited

OTHER PUBLICATIONS

Moseley, J., et al., (2009), "Genetic interactions between regulators of *Chlamydomonas* phosphorus and sulfur deprivation responses", *Genetics*, 181: 889-905.
Munthali, M., et al. (1996), "Use of E3 for biological containment of microorganisms" *Applied and Environmental Microbiology*, 62(5): 1805-1807.
Ohnuma M., et al. (2008), "Polyethylene glycol (PEG)-mediated transient gene expression in a red alga, *Cyanidioschyzon merolae* 10D", *Plant Cell Physiol.* 49(1):117-120.
Opel, M., et al. (2001), "The effects of DNA supercoiling on the expression of operons of the ilv regulon of *Escherichia coli* suggest a physiological rationale for divergently transcribed operons" *Molecular Microbiology*, 39(5): 1109-1115.
Overgaard, M., et al. (2009), "RelB and RelE of *Eschericia coli* form a tight complex that represses transcription via the ribbon-helix-helix motif in RelB", *J. Mol. Biol.*, 394: 183-196.
Pandey, G., et al. (2005), "Conceptualizing "suicidal genetically engineered microorganisms" for bioremediation applications" *Biochemical and Biophysical Research Communications*, 327: 637-639.
Pecota, D, et al. (1997), "Combining the hok/sok, parDE, and pnd postsegregational killer loci to enhance plasmid stability" *Applied and Environmental Microbiology*, 63(5): 1917-1924.
Perrone, C., et al. (1998), "The *Chlamydomonas* IDA7 locus encodes a 140 kDa dynein intermediate chain required to assemble the I1 inner arm complex", *Molecular biology of the Cell*, 9:3351-3365.
Poulsen, N., et al. (2005), "A new molecular tool for transgenic diatoms control of mRNA and protein biosynthesis by an inducible promoter-terminator cassette", *FEBS Journal*, 272: 3413-3423.
Quinn, J., et al. (2000), "Coordinate cooper- and Oxygen-responsive Cyc6 and Cpx1 expression in *Chlamydomonas* is mediated by the same element" *The Journal of Biological Chemistry*, 275(9): 6080-6089.
Revelles, O., et al. (2007), "Identification of the initial steps in $_D$ Lysine catabolism in *Pseudomonas putida*", *Journal of Bacteriology*, 189(7): 2787-2792.
Ronchel, C., et al. (1995), "Construction and behavior of biologically contained bacteria for environmental applications in bioremediation" *Applied and Environmental Microbiology*, 61(8): 2990-2994.
Saavedra De Bast, M., et al. (2008), "Chromosomal Toxin-Antitoxin Systems May Act as Antiaddiction Modules", *Journal of Bacteriology*, 190(13): 4603-4609.
Schmidt, O., et al. (2007), "prlF and yhaV encodes a new toxin-antitoxin system in *Escherichia coli*", *Journal of Mol. Biol.*, 372:894-905.
Schweder, T., et al. (1992), "An expression vector system providing plasmid stability and conditional suicide of plasmid-containing cells", *Appl Microbiol Biotechnol*, 38:91-93.
Sevin, E., et al. (2007), "RASTA-Bacteria: a web-based tool for identifying toxin-antitoxin loci in prokaryotes", *Genome Biology*, 8: R155.
Singh, V., et al. (1999), "ZntR is an autoregulatory protein and negatively regulates the chromosomal zinc resistance operon znt of *Staphylococcus aureus*", *Molecular Microbiology*, 33(1): 200-207.
Stieber, D., et al. (2008), "The art of selective killing: palasmid toxin/antitoxin systems and their technological applications", *Biotechniques*, 45(3): 344-346.
Stemmer, W., (1994), "DNA shuffling by random fragmentation and reassembly: in vitro recombination for molecular evolution", Proc. Natl. Acad. Sci. USA, 91: 10747-10751.
Suzuki, M., et al. (2005), "Single protein production in living cells facilitated by an mRNA interferase", *Molecular cell*, 18: 253-261.
Torres, B., et al., (2003), "A duel lethal system to enhance containment of recombinant micro-organisms" *Microbiology*, 149: 3595-3601.
Tramonti, A., et al., (2008), "GadX/GadW-dependent regulation of the *Escherichia coli* acid fitness island: transcriptional control at the gadY-gadW divergent promoters and identification of four novel 42 by GadX/GadW-specific binding sites", *Molecular Microbiology*, 70(4): 965-982.

Tsiatsiani, L., et al., (2011), "Metacaspases", Cell Death and Differentiation 18: 1279-1288.
Van Melderen, L., et al., (2009), "Bacterial toxin-antitoxin systems: more than selfish entities?", *PLoS Genetics*, 5(3): e1000437.
Van Melderen, L. (2010), "Toxin-antitoxin systems: why so many, what for?" *Current Opinion in Microbiology*, 13: 781-785.
Vercammen, D., et al., (2007), "Are metacaspases caspases?", *Journal of Cell Biology*, 375-380.
Watt, S., et al. "urg1: A Uracil-regulatable promoter system for fission yeast with short induction and repression times", *PLoS ONE*, 1: e1428.
Williams, J., et al., (2008), "Exposing plasmids as the achilles' heel of drug-resistant bacteria" *Current Opinion in Chemical Biology*, 12: 389-399.
Wurch, L., et al., (2011), "Nutrient-regulated transcriptional responses in the brown tide forming alga *Aureococcus anophagefferens*", *Environ Microbiol*, 13(2): 468-481.
Yamamoto, T., et al., (2002), "Bacterial toxin RelE induces apoptosis in human cells", FEBS Letters, 519: 191-194.
Yehudai-Resheff, S., et al. (2007), "Integration of chloroplast nucleic acid metabolism into the phosphate deprivation response in *Chlamydomonas reinhardtii*$^{[OA]}$", *The Plant Cell*, 19: 1023-1038.
Zhang, J., et al., (2004), "Interference of mRNA function by sequence-specific endoribonuclease PemK" *The Journal of Biological Chemistry*, 279(20), 20678-20684.
Zhang, Y., et al., (2005), "Characterization of ChpBK, an mRNA interferase from *Escherichia coli*," *The Journal of Biological Chemistry*, 280(28): 26080-26088.
Zhu, L., et al., (2008), "The mRNA interferases, MazF-mt3 and MazF-mt7 from *Mycobacterium tuberculosis* target unique pentad sequences in single-stranded RNA", *Molecular Microbiology*, 69(3): 559-569.
Zhuang, Q., et al., (2009) "Bacterial programmed cell death mediated by mazEF system under stressful conditions", *Microbiology China*, 36(6):905-909 (Abstract in English).
International Preliminary Report on Patentability dated Jan. 7, 2014 issued in PCT Application No. PCT/US2012/044654.
Chen, Y., et al. (2008) "The complete sequence and functional analysis of pANL, the large plasmid of the unicellular freshwater cyanobacterium *Synechococcus elongatus* PCC 7942", *Plasmid*, 59(3):176-192.
Supplemental European Search Report dated Sep. 29, 2014 issued in EP Application No. 12805262.8.
Makarova, K.S., et al. (2009) "Comprehensive comparative-genomic analysis of type 2 toxin-antitoxin systems and related mobile stress response systems in prokaryotes", *Biology Direct*, 4(19):1-38.
Ning, D., et al (2011) "The proteolytic activation of the reINEs (ssr1114/slr0664) toxin-antitoxin system by both proteases Ions and ClpP2s/Xs of *Synechocystis* sp. PCC6803", *Curr. Microbiol.*, 63:496-502.
Radakovits, R., et al. (2012) "Draft genome sequence and genetic transformation of the oleaginour alga *Nannochloropis gaditana*", *Nature Communications*, pp. 1-10.
UniProt Accession No. JU964024, May 17, 2012, 2 pages.
UniProt Accession No. JU966779, May 17, 2012, 2 pages.
UniProt Accession No. JU969013, May 17, 2012, 1 page.
UniProt Accession No. JU971427, May 17, 2012, 1 page.
UniProt Accession No. JU972789, May 17, 2012, 1 page.
UniProt Accession No. JU973541, May 17, 2012, 1 page.
UniProt Accession No. JU976044, May 17, 2012, 1 page.
UniProt Accession No. JU978567, May 17, 2012, 1 page.
Ye, S. et aL (2010) "The interaction between chromosome-encoded toxin slr0664 and antitoxin slr1114 of cyanobacteria synechocystis sp. PCC6803", *Acta Microbiologica Sinica*, 50(6):743-748—English Abstract Only.
Ye, S. et aL (2010) "The research on the chromosomal toxin-antitoxin genes ssr1114/slr0664 and ssl2920/ssl2921 of synechocystis sp. PCC6803", China Master, 87 pages—English Abstract Only.

* cited by examiner

```
                    1                                                                80
E. coli_MazF    (1)  ATGGTAAGCCGATACGTACCCGATATGGGCGATCTGATTTGGGTTGATTTTGACCCGACAAAAGGTAGCGAGCAAGCTGG
MazE-insens     (1)  ATGGTAAGCCGATACGTACCCGATATGGGCGATCTGATTTGGGTTGATTTTGACCCGACAAAAGGTAGCGAGCAAGCTGG
                    81                                                               160
E. coli_MazF   (81)  ACATCGTCCAGCTGTTGTCCTGAGTCCTTTCATGTACAACAAAAACAGGTATGTGTCTGTGTTCCTTGTACAACGC
MazE-insens    (81)  GCATCGTCCAGCTGTTGTCCTGAGTCCTTTCATGTATATAATAAAACCGGTATGTGTCTGTGTTCCTTGTACAACGC
                    161                                                              240
E. coli_MazF  (161)  AATCAAAAGGATATCCGTTCGAAGTTGTTTTATCCGGTCAGGAACGTGATGGCGTTAGCGTTAGCTGATCAGGTAAAAAGT
MazE-insens   (161)  AATCAAAAGGATATCCGTTCGAAGTTGTTTTATCCGGTCAGGAACGTGATGGCGTTAGCGTTAGCTGATCAGGTAAAAAGT
                    241                                                              320
E. coli_MazF  (241)  ATCGCCTGGCGGGCAAGAGGAGCAAGAAGAAGAACAGTTGCCCAGAGGAATTACAACTCATTAAAGCCAAATTAA
MazE-insens   (241)  ATCGCCTGGCGGGCAAGAGGAGCAAGAAGAAGAACCGTTGCCCAGAGGAATTGCAACTCATTAAAGCCAAATTAA
                    321            336
E. coli_MazF  (321)  CGTACTGATTGGGTAG
MazE-insens   (321)  CGTACTGATTGGGTAG
```

Figure 7

```
                 1                                                                        80
pemK_native   (1) ATGCTGAAATATCAGCTGAAGAACGAGAATGGCTGAAGATGCACCGGCGACTGGTCAGGAGGAAATCTGACATGGAAAGAGG
pemK_insens   (1) ATGCTGAAATACCAGCTGAAGAACGAGAATGGCTGAAGATGCACCGGCGACTGGTCAGGAGGAAATCTGACATGGAAAGAGG
                 81                                                                       160
pemK_native  (81) GGAAATCTGGCTTGTCTCGCTTGATCCTACCGCAGGTCATGAGCAGGAACGCGGCCGGTGCTGATTGTCACACCGG
pemK_insens  (81) GGAAATCTGGACTTGTCTCGACTTGATCCTACCGCAGGTCATGAGCAGGAACGCGGCCGGTGCTGATTGTCACACCGG
                 161                                                                      240
pemK_native (161) CGGCCTTTAATCGCGTGACCCGCTGCCTGTTGTTGCCCGTAACCAGCGGAGGCAATTTTGCCCGACCACTGCCGGCTTT
pemK_insens (161) CGGCCTTTCAATCGCGTGACCCGCTGCCTGTTGTTGCCCGTGACCAGCGGAGGCAATTTTGCCCGACCACTGCCGGCTTT
                 241                                                                      320
pemK_native (241) GCGGTGTCGTTGGATGGTGTTGGCATAGTACCACAGGTGTTGTAGTTGCGATCAATTGACAATTGATATGAAAGC
pemK_insens (241) GCGGTGTCGTCGGATGGTGTTGGCATCGTACCACCAGGTGTTGCGTTGCGATCAACCCGGACAATTGACAATGAAAGC
                 321                                                                      400
pemK_native (321) ACGGGGCGGAAAACGACTCGAACGAAGACTATCATGAACGGGTTCCGGAGACTGAACGAAGACTATCATCCACTATTCTGACTT
pemK_insens (321) ACGGGGCGGAAAACGACTCGAACGAAGACCATCATGAACGGGTTCCGGAGACCGAACGAAGTTCTTGCCGCCTGTCCACTATTCTGACTT
                 401
pemK_native (401) GA
pemK_insens (401) GA
```

Figure 8

```
                  1                                                                       80
       yafQ   (1) ATGATTCAAAGGGATATATTGAATACTCGGGACAATATTCAAAGGATGTAAAACTTGCACAAAAGGCGTCATAAGGATATGAA
MazE,YafQ-insens (1) ATGATTCAAAGGGATATATTGAATACTCGGGACAATATTCAAAGGATGTAAAACTTGCTCAAAAGGCGTCATAAGGATATGAA
                  81                                                                      160
       yafQ  (81) TAAATTGAAATATCTTATGACGCTTCTTATCAATAATACTTTACCGCTTCCAGCTGTTTATAAAGACCACCCGCTGCAAG
MazE,YafQ-insens(81) TAAATTGAAATATCTTATGACGCTTCTTATCAATAATACTTTACCGCTTCCAGCTGTTTATAAAGACCACCCGCTGCAAG
                  161                                                                     240
       yafQ (161) GTTCATGGAAGGTTATCGCGATGCTCATGTCATGTCGAACCGGAACCGGATCCTGATTTACAAACTTACCGATAAACTTTTACGA
MazE,YafQ-insens(161) GTTCATGGAAGGGTTATCGCGATGCTCATGTCATGTCGAACCGGAACCGGATCCTGATTTATAAACTTTATAAAACTTTTACGA
                  241      279
       yafQ (241) TTTGAGAGAACTGGAACTCACGCGGCGGCTCTTTGGGTAA
MazE,YafQ-insens(241) TTTGAGAGAACTGGAACTCACGCGGCGGCTCTTTGGGTAA
```

Figure 9

SEQUENCE LISTING

```
<160> NUMBER OF SEQ ID NOS: 80

<210> SEQ ID NO 1
<211> LENGTH: 264
<212> TYPE: DNA
<213> ORGANISM: Synechococcus elongatus

<400> SEQUENCE: 1
atgcgtaagc tggcttggac aaacgaggct tgggaagatt acctgtattg gcaagggcag    60
gacaagaaga ccttaaatcg catcaacaag ctcattaccg aaaccttgcg atcgcccttt   120 gagggggattg gtaagccaga agcgctcagg gagaacctga ctgggttttg gtcacgccgc   180
attgacgaca ccaatcgctt agtttacgca gtagcagatg actacctgac cattatttcc   240
tgtcgctacc actacagcga ttaa                                          264

<210> SEQ ID NO 2
<211> LENGTH: 87
<212> TYPE: PRT
<213> ORGANISM: Synechococcus elongatus

<400> SEQUENCE: 2

Met Arg Lys Leu Ala Trp Thr Asn Glu Ala Trp Glu Asp Tyr Leu Tyr
1               5                   10                  15

Trp Gln Gly Gln Asp Lys Lys Thr Leu Asn Arg Ile Asn Lys Leu Ile
                20                  25                  30

Thr Glu Thr Leu Arg Ser Pro Phe Glu Gly Ile Gly Lys Pro Glu Ala
            35                  40                  45

Leu Arg Glu Asn Leu Thr Gly Phe Trp Ser Arg Arg Ile Asp Asp Thr
        50                  55                  60

Asn Arg Leu Val Tyr Ala Val Ala Asp Asp Tyr Leu Thr Ile Ile Ser
65                  70                  75                  80

Cys Arg Tyr His Tyr Ser Asp
                85

<210> SEQ ID NO 3
<211> LENGTH: 414
<212> TYPE: DNA
<213> ORGANISM: Synechococcus elongatus

<400> SEQUENCE: 3
atgagctttg tgttggatgt ctcactggct tgtgcttggt gttttgcgga tgaggcaaca    60
ccggaatctt gggctttatt ggagcagttg caacaatctc cagcagttgt ccctgcactt   120
tggctctggg aagttgggca tgtcttggtg caagcagagc gccggcaaag gattagcgcc   180
gctgcgagtc gtgagttttt atcgctgcta gagatgttgc cgattgaggt agaacccgct   240
gctgtcggta ccgtttggca tgacacattg gcgatcgctt gcagtcaaca gctgactgct   300
tatgacgcag cttatttgga gctggcgatg cggcggggat tcgctctggc aacttgcgat   360
```
cgcgccttga tcagtgctgc ggaagccgtg ggagttacgt tactgccgac ctaa    414

<210> SEQ ID NO 4
<211> LENGTH: 137
<212> TYPE: PRT
<213> ORGANISM: Synechococcus elongatus

<400> SEQUENCE: 4

Met Ser Phe Val Leu Asp Val Ser Leu Ala Cys Ala Trp Cys Phe Ala
1               5                   10                  15

Asp Glu Ala Thr Pro Glu Ser Trp Ala Leu Leu Glu Gln Leu Gln Gln
            20                  25                  30

Ser Pro Ala Val Val Pro Ala Leu Trp Leu Trp Glu Val Gly His Val
        35                  40                  45

Leu Val Gln Ala Glu Arg Arg Gln Arg Ile Ser Ala Ala Ala Ser Arg
    50                  55                  60

Glu Phe Leu Ser Leu Leu Glu Met Leu Pro Ile Glu Val Glu Pro Ala
65                  70                  75                  80

Ala Val Gly Thr Val Trp His Asp Thr Leu Ala Ile Ala Cys Ser Gln
                85                  90                  95

Gln Leu Thr Ala Tyr Asp Ala Ala Tyr Leu Glu Leu Ala Met Arg Arg
            100                 105                 110

Gly Phe Ala Leu Ala Thr Cys Asp Arg Ala Leu Ile Ser Ala Ala Glu
        115                 120                 125

Ala Val Gly Val Thr Leu Leu Pro Thr
    130                 135

<210> SEQ ID NO 5
<211> LENGTH: 441
<212> TYPE: DNA
<213> ORGANISM: Anabaena PCC7120

<400> SEQUENCE: 5
gtgaagccgc cttactttcc caatagagga gacattgtta aattagagtt tggctctgca    60
caacagttca cggctgaatc aattcagcgt gtatttaccc ttcgtaattc tggaatgtca   120
tttgatgata ttgccataac actaaataac gagctacaac aacaagggcg tgagcaaact   180
ggctatcgcc ctgttcttgt tatatctcca attaagtaca atcaaatggc ttctttagtt   240
ttagcttgtc ctataactac taacgcaaag gggcttaggt ttgaagttcc ccttattgaa   300
ggaatgaaaa caaaggggt tgtgttagca gatcaaatta aaacactaga ttggaaagct   360
agaaaagtaa aatttgttga agtgtaaca gaagatttaa tagaagaagt acaagcaaaa   420
ctcgaaacat taattttata g                                            441

<210> SEQ ID NO 6
<211> LENGTH: 146
<212> TYPE: PRT
<213> ORGANISM: Anabaena PCC7120

<400> SEQUENCE: 6

Met Lys Pro Pro Tyr Phe Pro Asn Arg Gly Asp Ile Val Lys Leu Glu
1               5                   10                  15

Phe Gly Ser Ala Gln Gln Phe Thr Ala Glu Ser Ile Gln Arg Val Phe
            20                  25                  30

Thr Leu Arg Asn Ser Gly Met Ser Phe Asp Asp Ile Ala Ile Thr Leu
        35                  40                  45

```
Asn Asn Glu Leu Gln Gln Gly Arg Glu Gln Thr Gly Tyr Arg Pro
 50                  55                  60

Val Leu Val Ile Ser Pro Ile Lys Tyr Asn Gln Met Ala Ser Leu Val
 65                  70                  75                  80

Leu Ala Cys Pro Ile Thr Thr Asn Ala Lys Gly Leu Arg Phe Glu Val
                 85                  90                  95

Pro Leu Ile Glu Gly Met Lys Thr Lys Gly Val Val Leu Ala Asp Gln
                100                 105                 110

Ile Lys Thr Leu Asp Trp Lys Ala Arg Lys Val Lys Phe Val Glu Ser
            115                 120                 125

Val Thr Glu Asp Leu Ile Glu Glu Val Gln Ala Lys Leu Glu Thr Leu
130                 135                 140

Ile Leu
145
```

```
<210> SEQ ID NO 7
<211> LENGTH: 297
<212> TYPE: DNA
<213> ORGANISM: Anabaena PCC7120

<400> SEQUENCE: 7
atgggactta acagtaaaca tcaaaaaaca ctggatgaca tttttgaaaa tcccgttaga      60
tccaatattc cttggagtga tattgagtct atgctaattg cccttggtgc ggaagtgtca     120
gaaggaaggg ggtcaagggt gagaatagct cttaatggtg tcaaggcgac ttttcacaga    180
ccacacccgg aaaagaaac cgataaaggt gctgttaagt ctatgcggcg cttcttaaca     240
gagtctgggg ttcaagagga cttggagacg ggaggactta gtgacaatga aatataa       297

<210> SEQ ID NO 8
<211> LENGTH: 98
<212> TYPE: PRT
<213> ORGANISM: Anabaena PCC7120

<400> SEQUENCE: 8

Met Gly Leu Asn Ser Lys His Gln Lys Thr Leu Asp Asp Ile Phe Glu
  1               5                  10                  15

Asn Pro Val Arg Ser Asn Ile Pro Trp Ser Asp Ile Glu Ser Met Leu
                 20                  25                  30

Ile Ala Leu Gly Ala Glu Val Ser Glu Gly Arg Gly Ser Arg Val Arg
             35                  40                  45

Ile Ala Leu Asn Gly Val Lys Ala Thr Phe His Arg Pro His Pro Glu
 50                  55                  60

Lys Glu Thr Asp Lys Gly Ala Val Lys Ser Met Arg Arg Phe Leu Thr
 65                  70                  75                  80

Glu Ser Gly Val Gln Glu Asp Leu Glu Thr Gly Gly Leu Ser Asp Asn
                 85                  90                  95

Glu Ile

<210> SEQ ID NO 9
<211> LENGTH: 390
<212> TYPE: DNA
<213> ORGANISM: Anabaena PCC7120

<400> SEQUENCE: 9
atgagtggtg agattgcatt agatacttct gttgcaatac gttttttgaa tggtgatcct      60
gatgttgttt caagggtgtt ggcgttaccg gaaatatttt tgtcggtggt agtagttgga    120
```

```
gagttactgt ttggggctga gaactcgact cgaccgttga aaaatcttcc tcgatatttg    180
gagtttatgg aagtttgtac ggttgtgcct gtggaaaaga gaacagcagt tatctatgct    240
caaactcgtt ctgctttaaa gcgcaaagga cgaccaattc cgatgaatga tgtttggatt    300
gcagcgcatt gtctggaaca tggttgggtg cttgtgaccg ataattcaga ttttgattat    360
gtggatggat tggttataga gcattggtaa                                     390
```

```
<210> SEQ ID NO 10
<211> LENGTH: 129
<212> TYPE: PRT
<213> ORGANISM: Anabaena PCC7120

<400> SEQUENCE: 10
```

Met Ser Gly Glu Ile Ala Leu Asp Thr Ser Val Ala Ile Arg Phe Leu
1               5                   10                  15

Asn Gly Asp Pro Asp Val Val Ser Arg Val Leu Ala Leu Pro Glu Ile
                20                  25                  30

Phe Leu Ser Val Val Val Gly Glu Leu Leu Phe Gly Ala Glu Asn
            35                  40                  45

Ser Thr Arg Pro Leu Lys Asn Leu Pro Arg Tyr Leu Glu Phe Met Glu
    50                  55                  60

Val Cys Thr Val Val Pro Val Glu Lys Arg Thr Ala Val Ile Tyr Ala
65                  70                  75                  80

Gln Thr Arg Ser Ala Leu Lys Arg Lys Gly Arg Pro Ile Pro Met Asn
                85                  90                  95

Asp Val Trp Ile Ala Ala His Cys Leu Glu His Gly Trp Val Leu Val
            100                 105                 110

Thr Asp Asn Ser Asp Phe Asp Tyr Val Asp Gly Leu Val Ile Glu His
        115                 120                 125

Trp

```
<210> SEQ ID NO 11
<211> LENGTH: 357
<212> TYPE: DNA
<213> ORGANISM: Microcystis aeruginosa

<400> SEQUENCE: 11
atgacgattt ttcaaggaga gatttattgg attgatttag gagaaccaca aggttctgaa    60
cctgcttatc ttcgtccttg tgttgtggtg caaaatgatg ctctgaatca gtcacaaatt   120
gggacggtta ttgtgtgtcc attaacaacc aatttgagac gagcaaaagc tattggtaat   180
gttttattga atgagggtga agggaattta ccagaatcca gtgttgttaa tgtttcgcag   240
gttttcacgg ttgataagcg tcttttaaca gagtctatcg gaagactttc tcgggaaaaa   300
atcaaattaa ttattcaggg aattaatttg gttattgaac tcaagaact cgaataa      357
```

```
<210> SEQ ID NO 12
<211> LENGTH: 118
<212> TYPE: PRT
<213> ORGANISM: Microcystis aeruginosa

<400> SEQUENCE: 12
```

Met Thr Ile Phe Gln Gly Glu Ile Tyr Trp Ile Asp Leu Gly Glu Pro
1               5                   10                  15

Gln Gly Ser Glu Pro Ala Tyr Leu Arg Pro Cys Val Val Val Gln Asn
                20                  25                  30

Asp Ala Leu Asn Gln Ser Gln Ile Gly Thr Val Ile Val Cys Pro Leu

```
                35                  40                  45
Thr Thr Asn Leu Arg Arg Ala Lys Ala Ile Gly Asn Val Leu Leu Asn
     50                  55                  60

Glu Gly Glu Gly Asn Leu Pro Glu Ser Ser Val Asn Val Ser Gln
 65                  70                  75                  80

Val Phe Thr Val Asp Lys Arg Leu Leu Thr Glu Ser Ile Gly Arg Leu
                 85                  90                  95

Ser Arg Glu Lys Ile Lys Leu Ile Ile Gln Gly Ile Asn Leu Val Ile
            100                 105                 110

Glu Pro Gln Glu Leu Glu
        115

<210> SEQ ID NO 13
<211> LENGTH: 255
<212> TYPE: DNA
<213> ORGANISM: Synechococcus elongatus

<400> SEQUENCE: 13
atgaaagttg tttccttcag tgacgccaga aaaaatctca agactgtctt ggatgaagtc    60
gtcaacgacg ctgactacac gatcattact cgccgcaatg ccgaggaagt cgtggtcatg   120
tccctcgact ccttcaatag cctgatcgaa accttccacc tgctcaaatc ccctgccaat   180
gctgctcacc tacaacgtc gatcgctcag taccagcaag gtcaaacagt cgagcgaaat   240
ctattagatg cgtaa                                                     255

<210> SEQ ID NO 14
<211> LENGTH: 84
<212> TYPE: PRT
<213> ORGANISM: Synechococcus elongatus

<400> SEQUENCE: 14

Met Lys Val Val Ser Phe Ser Asp Ala Arg Lys Asn Leu Lys Thr Val
  1               5                  10                  15

Leu Asp Glu Val Val Asn Asp Ala Asp Tyr Thr Ile Ile Thr Arg Arg
                 20                  25                  30

Asn Ala Glu Glu Val Val Val Met Ser Leu Asp Ser Phe Asn Ser Leu
             35                  40                  45

Ile Glu Thr Phe His Leu Leu Lys Ser Pro Ala Asn Ala Ala His Leu
         50                  55                  60

Gln Arg Ser Ile Ala Gln Tyr Gln Gln Gly Gln Thr Val Glu Arg Asn
 65                  70                  75                  80

Leu Leu Asp Ala

<210> SEQ ID NO 15
<211> LENGTH: 315
<212> TYPE: DNA
<213> ORGANISM: Synechococcus elongatus

<400> SEQUENCE: 15
gtgcgggtga acctgaattt tgaaagcttt agcgatcgct tagactggtt ggcctctagt    60
tgtttgcttg ccatgcaaac tgttggcgcg tttgaagcca agaccatct ctccagcctg    120 ctcgactccg tctgtcaggg ggagcagatc gtgattaccc gccacggttg cccgatcgcc   180
cgtttggtgc cagcagaagg tcctgatcag tctgcggtcc aagccgcgat cgcccgtctt   240
cggcagctca gccaaggtca aaccctcaac ggaattacgg tgcaggaact ccgtgatact   300
gggcggcggg catga                                                     315
```

<210> SEQ ID NO 16
<211> LENGTH: 104
<212> TYPE: PRT
<213> ORGANISM: Synechococcus elongatus

<400> SEQUENCE: 16

```
Met Arg Val Asn Leu Asn Phe Glu Ser Phe Ser Asp Arg Leu Asp Trp
1               5                   10                  15

Leu Ala Ser Ser Cys Leu Leu Ala Met Gln Thr Val Gly Ala Phe Glu
            20                  25                  30

Ala Lys Thr His Leu Ser Ser Leu Leu Asp Ser Val Cys Gln Gly Glu
        35                  40                  45

Gln Ile Val Ile Thr Arg His Gly Cys Pro Ile Ala Arg Leu Val Pro
    50                  55                  60

Ala Glu Gly Pro Asp Gln Ser Ala Val Gln Ala Ile Ala Arg Leu
65                  70                  75                  80

Arg Gln Leu Ser Gln Gly Gln Thr Leu Asn Gly Ile Thr Val Gln Glu
                85                  90                  95

Leu Arg Asp Thr Gly Arg Arg Ala
            100
```

<210> SEQ ID NO 17
<211> LENGTH: 243
<212> TYPE: DNA
<213> ORGANISM: Anabaena PCC7120

<400> SEQUENCE: 17

```
atgacaacag ttgtagctaa atggggaaac agtttagcgg ttaggattcc tagatcgata    60
gctgaacaag cacacgtaac tgaaggaaca gatatcaatt ttagtgttga aggtaatagc   120
atagtaatta caccaaagag acgaaaaaaa tatacgcttg atgagttact tgaagggatg   180
accccctgata atttcatcc agaatttgaa acaggtgacg ctgtggggaa tgaagcttgg   240
tag                                                                 243
```

<210> SEQ ID NO 18
<211> LENGTH: 80
<212> TYPE: PRT
<213> ORGANISM: Anabaena PCC7120

<400> SEQUENCE: 18

```
Met Thr Thr Val Val Ala Lys Trp Gly Asn Ser Leu Ala Val Arg Ile
1               5                   10                  15

Pro Arg Ser Ile Ala Glu Gln Ala His Val Thr Glu Gly Thr Asp Ile
            20                  25                  30

Asn Phe Ser Val Glu Gly Asn Ser Ile Val Ile Thr Pro Lys Arg Arg
        35                  40                  45

Lys Lys Tyr Thr Leu Asp Glu Leu Leu Glu Gly Met Thr Pro Asp Asn
    50                  55                  60

Phe His Pro Glu Phe Glu Thr Gly Asp Ala Val Gly Asn Glu Ala Trp
65                  70                  75                  80
```

<210> SEQ ID NO 19
<211> LENGTH: 327
<212> TYPE: DNA
<213> ORGANISM: Nostoc sp. PCC7120

<400> SEQUENCE: 19

```
gtgacaatga aatataaagg atatgaagcc attgtcgaat ttgatgatga agctgaaatt    60
tttcatgggg aagtaattaa ccttcgagat gtgattacat ttcagggtga cagcgtcaaa   120
gagctaaagc aagcttttca tgattcagta gacgattatt tagaattttg tcaagaacgt   180
ggcgaagaac ctgaaaaacc cttttcagga aaactcatgc tcagaattaa ccctgaatta   240
cataaaatca tcgccatcaa agcgaagaaa gagggacaaa gccttaattc ttggatagaa   300
aaatgcttgt gtatgtatgt tccttag                                       327
```

```
<210> SEQ ID NO 20
<211> LENGTH: 108
<212> TYPE: PRT
<213> ORGANISM: Nostoc sp. PCC7120

<400> SEQUENCE: 20

Met Thr Met Lys Tyr Lys Gly Tyr Glu Ala Ile Val Glu Phe Asp Asp
1               5                   10                  15

Glu Ala Glu Ile Phe His Gly Glu Val Ile Asn Leu Arg Asp Val Ile
            20                  25                  30

Thr Phe Gln Gly Asp Ser Val Lys Glu Leu Lys Gln Ala Phe His Asp
        35                  40                  45

Ser Val Asp Asp Tyr Leu Glu Phe Cys Gln Glu Arg Gly Glu Glu Pro
    50                  55                  60

Glu Lys Pro Phe Ser Gly Lys Leu Met Leu Arg Ile Asn Pro Glu Leu
65                  70                  75                  80

His Lys Ile Ile Ala Ile Lys Ala Lys Lys Glu Gly Gln Ser Leu Asn
                85                  90                  95

Ser Trp Ile Glu Lys Cys Leu Cys Met Tyr Val Pro
            100                 105
```

```
<210> SEQ ID NO 21
<211> LENGTH: 210
<212> TYPE: DNA
<213> ORGANISM: Nostoc sp. PCC7120

<400> SEQUENCE: 21
atgactagcc gcgagcagct tatccaagaa cttgcagagg ttccagatga gttagttaaa    60
gtaatgttag atttttttaca tcgtcttcag acaacgcgca gtcatcatcc tctagcgaaa   120
tttgctggta ttttgagtga taatgaggcg gccgatttac aggaagcaat tcaagctgat   180
tgtcgtcagg ttgatttaaa tgagtggtga                                     210
```

```
<210> SEQ ID NO 22
<211> LENGTH: 69
<212> TYPE: PRT
<213> ORGANISM: Nostoc sp. PCC7120

<400> SEQUENCE: 22

Met Thr Ser Arg Glu Gln Leu Ile Gln Glu Leu Ala Glu Val Pro Asp
1               5                   10                  15

Glu Leu Val Lys Val Met Leu Asp Phe Leu His Arg Leu Gln Thr Thr
            20                  25                  30

Arg Ser His His Pro Leu Ala Lys Phe Ala Gly Ile Leu Ser Asp Asn
        35                  40                  45

Glu Ala Ala Asp Leu Gln Glu Ala Ile Gln Ala Asp Cys Arg Gln Val
    50                  55                  60

Asp Leu Asn Glu Trp
65
```

<210> SEQ ID NO 23
<211> LENGTH: 231
<212> TYPE: DNA
<213> ORGANISM: Microcystis aeruginosa

<400> SEQUENCE: 23

```
atgttatctt ctctgataat tgaactggaa caaaagttac gagactgttc tcttgaagat    60
aaacaatggt tattggagca gttacatcaa caattaggat tgaataatca aaaaacaact   120
aaacaacgat taatagatag ttggaatgaa gcttatagtg atggattgga cgaatcagaa   180
actttaatgt tagagcgaat acggcatcat caaagccaat tatctgagta a            231
```

<210> SEQ ID NO 24
<211> LENGTH: 76
<212> TYPE: PRT
<213> ORGANISM: Microcystis aeruginosa

<400> SEQUENCE: 24

```
Met Leu Ser Ser Leu Ile Ile Glu Leu Glu Gln Lys Leu Arg Asp Cys
1               5                   10                  15

Ser Leu Glu Asp Lys Gln Trp Leu Leu Glu Gln Leu His Gln Gln Leu
            20                  25                  30

Gly Leu Asn Asn Gln Lys Thr Thr Lys Gln Arg Leu Ile Asp Ser Trp
        35                  40                  45

Asn Glu Ala Tyr Ser Asp Gly Leu Asp Glu Ser Glu Thr Leu Met Leu
    50                  55                  60

Glu Arg Ile Arg His His Gln Ser Gln Leu Ser Glu
65                  70                  75
```

<210> SEQ ID NO 25
<211> LENGTH: 28
<212> TYPE: DNA
<213> ORGANISM: Artificial Sequence
<220> FEATURE:
<223> OTHER INFORMATION: UF primer PCC7942-axe

<400> SEQUENCE: 25

```
atgaaagttg tttccttcag tgacgcca                                       28
```

<210> SEQ ID NO 26
<211> LENGTH: 29
<212> TYPE: DNA
<213> ORGANISM: Artificial Sequence
<220> FEATURE:
<223> OTHER INFORMATION: IR primer PCC7942-axe

<400> SEQUENCE: 26

```
ttacgcatct aatagatttc gctcgactg                                      29
```

<210> SEQ ID NO 27
<211> LENGTH: 24
<212> TYPE: DNA
<213> ORGANISM: Artificial Sequence
<220> FEATURE:
<223> OTHER INFORMATION: UF primer PCC7942-txe

<400> SEQUENCE: 27

```
atgcgtaagc tggcttggac aaac                                           24
```

<210> SEQ ID NO 28
<211> LENGTH: 24

-continued

<210> SEQ ID NO 28
<211> LENGTH: 24
<212> TYPE: DNA
<213> ORGANISM: Artificial Sequence
<220> FEATURE:
<223> OTHER INFORMATION: IR primer PCC7942-txe

<400> SEQUENCE: 28
ttaatcgctg tagtggtagc gaca                                              24

<210> SEQ ID NO 29
<211> LENGTH: 26
<212> TYPE: DNA
<213> ORGANISM: Artificial Sequence
<220> FEATURE:
<223> OTHER INFORMATION: UF primer PCC7942-phd

<400> SEQUENCE: 29
gtgcgggtga acctgaattt tgaaag                                            26

<210> SEQ ID NO 30
<211> LENGTH: 22
<212> TYPE: DNA
<213> ORGANISM: Artificial Sequence
<220> FEATURE:
<223> OTHER INFORMATION: IR primer PCC7942-phd

<400> SEQUENCE: 30
tcatgcccgc cgcccagtat ca                                                22

<210> SEQ ID NO 31
<211> LENGTH: 27
<212> TYPE: DNA
<213> ORGANISM: Artificial Sequence
<220> FEATURE:
<223> OTHER INFORMATION: UF primer PCC7942-doc

<400> SEQUENCE: 31
atgagctttg tgttggatgt ctcactg                                           27

<210> SEQ ID NO 32
<211> LENGTH: 24
<212> TYPE: DNA
<213> ORGANISM: Artificial Sequence
<220> FEATURE:
<223> OTHER INFORMATION: IR primer PCC7942-doc

<400> SEQUENCE: 32
ttaggtcggc agtaacgtaa ctcc                                              24

<210> SEQ ID NO 33
<211> LENGTH: 30
<212> TYPE: DNA
<213> ORGANISM: Artificial Sequence
<220> FEATURE:
<223> OTHER INFORMATION: UF primer PCC7120-mazE

<400> SEQUENCE: 33
atgacaacag ttgtagctaa atggggaaac                                        30

<210> SEQ ID NO 34
<211> LENGTH: 23
<212> TYPE: DNA
<213> ORGANISM: Artificial Sequence
<220> FEATURE:
<223> OTHER INFORMATION: IR primer PCC7120-mazE

<400> SEQUENCE: 34

```
ctaccaagct tcattcccca cag                                              23
```

```
<210> SEQ ID NO 35
<211> LENGTH: 25
<212> TYPE: DNA
<213> ORGANISM: Artificial Sequence
<220> FEATURE:
<223> OTHER INFORMATION: UF primer PCC7120-mazF

<400> SEQUENCE: 35
gtgaagccgc cttactttcc caata                                            25
```

```
<210> SEQ ID NO 36
<211> LENGTH: 37
<212> TYPE: DNA
<213> ORGANISM: Artificial Sequence
<220> FEATURE:
<223> OTHER INFORMATION: IR primer PCC7120-mazF

<400> SEQUENCE: 36
ctataaaatt aatgtttcga gttttgcttg tacttct                               37
```

```
<210> SEQ ID NO 37
<211> LENGTH: 384
<212> TYPE: DNA
<213> ORGANISM: Artificial Sequence
<220> FEATURE:
<223> OTHER INFORMATION: Microcystis pemK codon-optimized for
      Synechocystis, FLAG tagged

<400> SEQUENCE: 37
atgacgattt ttcaaggaga gatttattgg attgatttag gagaaccaca aggttctgaa      60
cctgcttatc ttcgtccttg tgttgtggtg caaaatgatg ctctgaatca gtcacaaatt     120
gggacggtta ttgtgtgtcc attaacaacc aatttgagac gagcaaaagc tattggtaat     180
gttttattga atgagggtga agggaattta ccagaatcca gtgttgttaa tgtttcgcag     240
gttttcacgg ttgataagcg tcttttaaca gagtctatcg gaagactttc tcgggaaaaa     300
atcaaattaa ttattcaggg aattaatttg gttattgaac ctcaagaact cgaaggcagt     360
gactataaag atgacgatga caaa                                           384
```

```
<210> SEQ ID NO 38
<211> LENGTH: 258
<212> TYPE: DNA
<213> ORGANISM: Artificial Sequence
<220> FEATURE:
<223> OTHER INFORMATION: Microcystis pemI codon-optimized for
      Synechocystis, FLAG tagged

<400> SEQUENCE: 38
atgttatctt ctctgataat tgaactggaa caaaagttac gagactgttc tcttgaagat      60
aaacaatggt tattggagca gttacatcaa caattaggat tgaataatca aaaaacaact     120
aaacaacgat taatagatag ttggaatgaa gcttatagtg atggattgga cgaatcagaa     180
actttaatgt tagagcgaat acggcatcat caaagccaat tatctgaggg cagtgactat     240
aaagatgacg atgacaaa                                                  258
```

```
<210> SEQ ID NO 39
<211> LENGTH: 1217
<212> TYPE: DNA
<213> ORGANISM: Escherichia coli

<400> SEQUENCE: 39
```

```
cgtttcactc catccaaaaa aacgggtatg gagaaacagt agagagttgc gataaaaagc    60
gtcaggtagg atccgctaat cttatggata aaaatgctat ggcatagcaa agtgtgacgc   120
cgtgcaaata atcaatgtgg actttttctgc cgtgattata gacacttttg ttacgcgttt   180
ttgtcatggc tttggtcccg ctttgttaca gaatgctttt aataagcggg gttaccggtt   240
gggttagcga gaagagccag taaaagacgc agtgacggca atgtctgatg caatatggac   300
aattggtttc ttctctgaat ggtgggagta tgaaaagtat ggctgaagcg caaaatgatc   360
ccctgctgcc gggatactcg tttaacgccc atctggtggc gggtttaacg ccgattgagg   420
ccaacggtta tctcgatttt tttatcgacc gaccgctggg aatgaaaggt tatattctca   480
atctcaccat tcgcggtcag ggggtggtga aaaatcaggg acgagaattt gtctgccgac   540
cgggtgatat tttgctgttc ccgccaggag agattcatca ctacggtcgt catccggagg   600
ctcgcgaatg gtatcaccag tgggtttact ttcgtccgcg cgcctactgg catgaatggc   660
ttaactggcc gtcaatattt gccaatacgg gtttctttcg cccggatgaa gcgcaccagc   720
cgcatttcag cgacctgttt gggcaaatca ttaacgccgg gcaaggggaa gggcgctatt   780
cggagctgct ggcgataaat ctgcttgagc aattgttact gcggcgcatg gaagcgatta   840
acgagtcgct ccatccaccg atggataatc gggtacgcga ggcttgtcag tacatcagcg   900
atcacctggc agacagcaat tttgatatcg ccagcgtcgc acagcatgtt tgcttgtcgc   960
cgtcgcgtct gtcacatctt ttccgccagc agttagggat tagcgtctta agctggcgcg  1020
aggaccaacg cattagtcag gcgaagctgc ttttgagcac tacccggatg cctatcgcca  1080
ccgtcggtcg caatgttggt tttgacgatc aactctattt ctcgcgagta tttaaaaaat  1140
gcaccggggc cagcccgagc gagtttcgtg ccggttgtga agaaaaagtg aatgatgtag  1200
ccgtcaagtt gtcataa                                                 1217

<210> SEQ ID NO 40
<211> LENGTH: 989
<212> TYPE: DNA
<213> ORGANISM: Synechocystis PCC6803

<400> SEQUENCE: 40
attgctgaag cggaatccct ggttaatgcc gccgccgatg ccaattgcat tctccaagtg    60
gggcacattg aacgcttcaa cccggcattt ttagagctaa ccaaaattct caaaacggaa   120
gagttattgg cgatcgaagc ccatcgcatg agtccctatt cccagcgggc caatgatgtc   180
tccgtggtat tggatttgat gatccatgac attgacctgt tgctggaatt ggtgggttcg   240
gaagtggtta aactgtccgc cagtggcagt cgggcttctg ggtcaggata tttggattat   300
gtcaccgcta cgttaggctt ctcctccggc attgtggcca ccctcaccgc cagtaaggtc   360
acccatcgta aaattcgttc catcgccgcc cactgcaaaa attccctcac cgaagcggat   420
tttctcaata cgaaattttt gatccatcgc caaaccaccg ctgattggag cgcggactat   480
ggccaggtat tgtatcgcca ggatggtcta atcgaaaagg tttacaccag taatattgaa   540
cctctccacg ctgaattaga acatttttatt cattgtgtta ggggaggtga tcaaccctca   600
gtgggggagg aacaggccct caaggccctg aagttagcca gtttaattga agaaatggcc   660
ctggacagtc aggaatggca tgggggggaa gttgtgacag aatatcaaga tgccaccctg   720
gccctcagtg cgagtgttta aatcaactta attaatgcaa ttattgcgag ttcaaactcg   780
ataactttgt gaaatattac tgttgaatta atctatgact attcaataca ccccctagc   840
```

| cgatcgcctg ttggcctacc tcgccgccga tcgcctaaat ctcagcgcca agagtagttc | 900 |
| cctcaacacc agtattctgc tcagcagtga cctattcaat caggaagggg gaattgtaac | 960 |
| agccaactat ggctttgatg gttatatgg | 989 |

<210> SEQ ID NO 41
<211> LENGTH: 989
<212> TYPE: DNA
<213> ORGANISM: Synechocystis PCC6803

<400> SEQUENCE: 41

| ccggtatgga tggcaccgat gcggaatccc aacagattgc ctttgacaac aatgtggcct | 60 |
| ggaataacct gggggatttg tccaccacca cccaacgggc ctacacttcg gctattagca | 120 |
| cagacacagt gcagagtgtt tatggcgtta atctggaaaa aaacgataac attcccattg | 180 |
| tttttgcgtg gcccattttt cccaccaccc ttaatcccac agattttcag gtaatgctta | 240 |
| acacgggga aattgtcacc ccggtgatcg cctctttgat tcccaacagt gaatacaacg | 300 |
| aacggcaaac ggtagtaatt acgggcaatt ttggtaatcg tttaacccca ggcacggagg | 360 |
| gagcgattta tcccgtttcc gtaggcacag tgttggacag tactcctttg gaaatggtgg | 420 |
| gacccaacgg cccggtcagt gcggtgggta ttaccattga tagtctcaac ccctacgtgg | 480 |
| ccggcaatgg tcccaaaatt gtcgccgcta agttagaccg cttcagtgac ctggggggaag | 540 |
| gggctcccct ctggttagcc accaatcaaa ataacagtgg cggggattta tatggagacc | 600 |
| aagcccaatt tcgtttgcga atttacacca gcgccggttt ttcccccgat ggcattgcca | 660 |
| gtttactacc cacagaattt gaacggtatt ttcaactcca gcggaagat attacgggac | 720 |
| ggacagttat cctaacccaa actggtgttg attatgaaat tcccggcttt ggtctggtgc | 780 |
| aggtgttggg gctggcggat ttggccgggg ttcaggacag ctatgacctg acttacatcg | 840 |
| aagatcatga caactattac gacattatcc tcaaggggga cgaagccgca gttcgccaaa | 900 |
| ttaagagggt tgctttgccc tccgaaggg attattcggc ggtttataat cccggtggcc | 960 |
| ccggcaatga tccagagaat ggtccccca | 989 |

<210> SEQ ID NO 42
<211> LENGTH: 216
<212> TYPE: DNA
<213> ORGANISM: Artificial Sequence
<220> FEATURE:
<223> OTHER INFORMATION: cDNA for ccdA from Escherichia coli

<400> SEQUENCE: 42

| atgaagcagc gtattacagt ggcaggtgac agcgacaact atcagttgct caaggcatat | 60 |
| gatgtcaata tctccggtct ggtaagcacc cccatgcaga atgaagcccg tcgtctgcgt | 120 |
| cccgaacgtt ggaaagtggc aaatcaggaa gggatggctg aggtcgcccg gtttattgaa | 180 |
| atgaacggct cttttgctga cgagaacagg gactgg | 216 |

<210> SEQ ID NO 43
<211> LENGTH: 72
<212> TYPE: PRT
<213> ORGANISM: Escherichia coli

<400> SEQUENCE: 43

Met Lys Gln Arg Ile Thr Val Ala Gly Asp Ser Asp Asn Tyr Gln Leu
1               5                   10                  15

Leu Lys Ala Tyr Asp Val Asn Ile Ser Gly Leu Val Ser Thr Pro Met
            20                  25                  30

```
Gln Asn Glu Ala Arg Arg Leu Arg Pro Glu Arg Trp Lys Val Ala Asn
            35                  40                  45

Gln Glu Gly Met Ala Glu Val Ala Arg Phe Ile Glu Met Asn Gly Ser
        50                  55                  60

Phe Ala Asp Glu Asn Arg Asp Trp
65                  70

<210> SEQ ID NO 44
<211> LENGTH: 303
<212> TYPE: DNA
<213> ORGANISM: Artificial Sequence
<220> FEATURE:
<223> OTHER INFORMATION: cDNA for ccdB from Escherichia coli

<400> SEQUENCE: 44
atgcagttta aggtttacac ctataaaaga gagagccgtt atcgtctgtt tgtggatgtt      60
cagagtgaca ttattgacac gcccgggcga cggatggtga tccccctggc cagtgcccgc    120
ctgctgtcag acaaagtctc ccgtgagctt tacccggtgg tgcatgtcgg ggatgaaagc    180
tggcgcatga tgaccaccga tatggccagt gtgccggtct ccgttatcgg ggaagaagtg    240
gctgatctca gtcaccgcga aaatgacatc aaaaacgcca ttaacctgat gttctgggga    300
ata                                                                   303

<210> SEQ ID NO 45
<211> LENGTH: 101
<212> TYPE: PRT
<213> ORGANISM: Escherichia coli

<400> SEQUENCE: 45

Met Gln Phe Lys Val Tyr Thr Tyr Lys Arg Glu Ser Arg Tyr Arg Leu
1               5                   10                  15

Phe Val Asp Val Gln Ser Asp Ile Ile Asp Thr Pro Gly Arg Arg Met
            20                  25                  30

Val Ile Pro Leu Ala Ser Ala Arg Leu Leu Ser Asp Lys Val Ser Arg
        35                  40                  45

Glu Leu Tyr Pro Val Val His Val Gly Asp Glu Ser Trp Arg Met Met
    50                  55                  60

Thr Thr Asp Met Ala Ser Val Pro Val Ser Val Ile Gly Glu Glu Val
65                  70                  75                  80

Ala Asp Leu Ser His Arg Glu Asn Asp Ile Lys Asn Ala Ile Asn Leu
                85                  90                  95

Met Phe Trp Gly Ile
            100

<210> SEQ ID NO 46
<211> LENGTH: 2244
<212> TYPE: DNA
<213> ORGANISM: Leptolyngbya sp.

<400> SEQUENCE: 46
atgccccgga ttaaacgtcg ccatttcttg caagctgctg atcgagtct tgctgcgatc      60 ggattgagcc agttggatgt gtttcggcaa gcggaacagt atggcaaagt attagctcag    120
agtagtcagc gtaagcttgc actactcgtt gggatcaatg ctatcccga atctgttggc    180 tcgcttcagg gatgtcttac ggatctggaa atgcagtatg aattattgag atatcgttat    240
ggttttgcga agaatgatat tttagtgctt gccgatcgga ggttatcgtt tcttgactat    300
```

```
gagccggaga agccgacacg ccagaacatt ctaaatgcgt tcagaaaca tttgattgat      360
ccgtctactc cagatagcgt tgttgttttt cattattctg ggcatggttc gctcatccct      420
gatcccctca ttaagacgcc tttgttggat gctgacggga agaagattgt gacacagagt      480
ggaaagcctg cgagtgggac gattgtgccg ctagatcgct atgcgaccaa tgggagacgt      540
tcaggtgaag tgcaagatat tatggggcgc agtttgtttt tgttgatgag atcgctgaag      600
acaaacaatg tgactgcggt tttggatagt tgccattcgg gcggaggaac gcgagggaat      660
gtgaccttc gggctgcgtc tcgtttaacg agtcaggatg ccagtcccag tgagatggag      720
acagagttcc agaagcgatt aatccaggat cggggtttaa agtttgaaga gatcgaagca      780
gagcggcgga aggatgttgc taaaggggtg gcgatcgggt cagctcgata taaccagcag      840
gcagcggata gtacgtttgg caatagtgaa gatggcagtc aatttcatgc gggggcgttt      900
acctatgcat tgactcgcta tctctggcaa caatcggttt cagattcgtt taagacaacc      960
tttgtcaatt tgcagcggag cactcaagtt gttgcgagta acggtgggat tgagcagatc     1020
ccgatcgtgg atggcaatcc gcagcagaat ctggatcaac ccttctactt tttatcggcg     1080
acggctccct atgcggaggc ggtggtgcgg agcgtggagg cgaatgagac aattcgattt     1140
tggttgggcg ggttgtcttc ggtgagtttg gagcggggtg agaagtcgat ttttagcgcg     1200
atcgatggtg ctggaaatga gattggggaa attgagcagg aaggtcgcag agggatggtg     1260
gggacgggca aactgcgcaa gggtgatctg aacgcgatta aaccgggcgt gctattgcgg     1320
gaacaggtgc gagggttgaa gcctgatttt aagttaagaa tcgggttaga tccgtcgttg     1380
gggaaggatc tcgaagccgc gaagcaattg ctgagccagg tgaagaattt cgaggtggtg     1440
gagtcgcaag cattcatgca ctatcgggtg ggacggatga cgcaggagat tcaaactgcg     1500
tctcgctcta ctaatttgcc gaatattggc agtacagggc tgatgacggg ggcactgagt     1560
ccgttgacgg cgacatttag ggagacgagt gaggggattg aggatgcgat cgcgcgtctc     1620
attcagccat tgaagacgtt tttggcgaag gagattctga atgcgatcgg gggcgttgat     1680
gtggcatctg gggttcgacc tgcggggttg agtgtgcggg tagatgcgat taagccaggt     1740
ggacaggtgg gtgcgaatcg ctttaagccg gaaacacctt accaggtgac gattcggaac     1800
aatggtgata atccctcta tgtggcggcg atttcgattg ggtcggcggg tcggctgcgc     1860
ttttgtatc cgccttctga ggcgatggac aatgtttccg aggatagtgc tcggattggg     1920
acgggggagg agaaggttgt gaagggttgg cagactggga aattgccagg acggtggag     1980
gtgatggtga tttcgagtgg gcagcctgtc tatgatgcgc tgaaggcttt gaaggcgatc     2040
gcggcgcgag gaagaggtgt gtcttctagc cgaggtccat ctagtgcgcc tgcgacgggt     2100
gaggatgcgt tggaggcgat gagtgcgctg ctgggggatc tggatcgcaa tactcgcagc     2160
gattctgttc cggtttcccg cgatgtgaaa ggggtggcga ctcgtcagat tagtgtgatt     2220
tcgacgccga ttgaggtggt gaag                                             2244
```

<210> SEQ ID NO 47
<211> LENGTH: 748
<212> TYPE: PRT
<213> ORGANISM: Leptolyngbya sp.

<400> SEQUENCE: 47

```
Met Pro Arg Ile Lys Arg Arg His Phe Leu Gln Ala Ala Gly Ser Ser
1               5                   10                  15

Leu Ala Ala Ile Gly Leu Ser Gln Leu Asp Val Phe Arg Gln Ala Glu
            20                  25                  30
```

```
Gln Tyr Gly Lys Val Leu Ala Gln Ser Ser Gln Arg Lys Leu Ala Leu
         35                  40                  45

Leu Val Gly Ile Asn Gly Tyr Pro Glu Ser Val Gly Ser Leu Gln Gly
 50                  55                  60

Cys Leu Thr Asp Leu Glu Met Gln Tyr Glu Leu Leu Arg Tyr Arg Tyr
 65                  70                  75                  80

Gly Phe Ala Lys Asn Asp Ile Leu Val Leu Ala Asp Arg Arg Leu Ser
                 85                  90                  95

Phe Leu Asp Tyr Glu Pro Glu Lys Pro Thr Arg Gln Asn Ile Leu Asn
             100                 105                 110

Ala Phe Gln Lys His Leu Ile Asp Pro Ser Thr Pro Asp Ser Val Val
             115                 120                 125

Val Phe His Tyr Ser Gly His Gly Ser Leu Ile Pro Asp Pro Leu Ile
         130                 135                 140

Lys Thr Pro Leu Leu Asp Ala Asp Gly Lys Lys Ile Val Thr Gln Ser
145                 150                 155                 160

Gly Lys Pro Ala Ser Gly Thr Ile Val Pro Leu Asp Arg Tyr Ala Thr
                 165                 170                 175

Asn Gly Arg Arg Ser Gly Glu Val Gln Asp Ile Met Gly Arg Ser Leu
             180                 185                 190

Phe Leu Leu Met Arg Ser Leu Lys Thr Asn Asn Val Thr Ala Val Leu
             195                 200                 205

Asp Ser Cys His Ser Gly Gly Gly Thr Arg Gly Asn Val Thr Phe Arg
210                 215                 220

Ala Ala Ser Arg Leu Thr Ser Gln Asp Ala Ser Pro Ser Glu Met Glu
225                 230                 235                 240

Thr Glu Phe Gln Lys Arg Leu Ile Gln Asp Arg Gly Leu Lys Phe Glu
                 245                 250                 255

Glu Ile Glu Ala Glu Arg Arg Lys Asp Val Ala Lys Gly Val Ala Ile
             260                 265                 270

Gly Ser Ala Arg Tyr Asn Gln Gln Ala Ala Asp Ser Thr Phe Gly Asn
             275                 280                 285

Ser Glu Asp Gly Ser Gln Phe His Ala Gly Ala Phe Tyr Ala Leu
             290                 295                 300

Thr Arg Tyr Leu Trp Gln Gln Ser Val Ser Asp Ser Phe Lys Thr Thr
305                 310                 315                 320

Phe Val Asn Leu Gln Arg Ser Thr Gln Val Val Ala Ser Asn Gly Gly
                 325                 330                 335

Ile Glu Gln Ile Pro Ile Val Asp Gly Asn Pro Gln Asn Leu Asp
             340                 345                 350

Gln Pro Phe Tyr Phe Leu Ser Ala Thr Ala Pro Tyr Ala Glu Ala Val
             355                 360                 365

Val Arg Ser Val Glu Ala Asn Glu Thr Ile Arg Phe Trp Leu Gly Gly
370                 375                 380

Leu Ser Ser Val Ser Leu Glu Arg Gly Glu Lys Ser Ile Phe Ser Ala
385                 390                 395                 400

Ile Asp Gly Ala Gly Asn Glu Ile Gly Glu Ile Glu Gln Gly Arg
             405                 410                 415

Arg Gly Met Val Gly Thr Gly Lys Leu Arg Lys Gly Asp Leu Asn Ala
             420                 425                 430

Ile Lys Pro Gly Val Leu Leu Arg Glu Gln Val Arg Gly Leu Lys Pro
             435                 440                 445
```

Asp Phe Lys Leu Arg Ile Gly Leu Asp Pro Ser Leu Gly Lys Asp Leu
    450                 455                 460

Glu Ala Ala Lys Gln Leu Leu Ser Gln Val Lys Asn Phe Glu Val Val
465                 470                 475                 480

Glu Ser Gln Ala Phe Met His Tyr Arg Val Gly Arg Met Thr Gln Glu
                485                 490                 495

Ile Gln Thr Ala Ser Arg Ser Thr Asn Leu Pro Asn Ile Gly Ser Thr
            500                 505                 510

Gly Leu Met Thr Gly Ala Leu Ser Pro Leu Thr Ala Thr Phe Arg Glu
        515                 520                 525

Thr Ser Glu Gly Ile Glu Asp Ala Ile Ala Arg Leu Ile Gln Pro Leu
530                 535                 540

Lys Thr Phe Leu Ala Lys Glu Ile Leu Asn Ala Ile Gly Gly Val Asp
545                 550                 555                 560

Val Ala Ser Gly Val Arg Pro Ala Gly Leu Ser Val Arg Val Asp Ala
                565                 570                 575

Ile Lys Pro Gly Gly Gln Val Gly Ala Asn Arg Phe Lys Pro Glu Thr
            580                 585                 590

Pro Tyr Gln Val Thr Ile Arg Asn Asn Gly Asp Lys Ser Leu Tyr Val
        595                 600                 605

Ala Ala Ile Ser Ile Gly Ser Ala Gly Arg Leu Arg Phe Leu Tyr Pro
610                 615                 620

Pro Ser Glu Ala Met Asp Asn Val Ser Glu Asp Ser Ala Arg Ile Gly
625                 630                 635                 640

Thr Gly Glu Glu Lys Val Val Lys Gly Trp Gln Thr Gly Lys Leu Pro
                645                 650                 655

Gly Thr Val Glu Val Met Val Ile Ser Ser Gly Gln Pro Val Tyr Asp
            660                 665                 670

Ala Leu Lys Ala Leu Lys Ala Ile Ala Ala Arg Gly Arg Gly Val Ser
        675                 680                 685

Ser Ser Arg Gly Pro Ser Ser Ala Pro Ala Thr Gly Glu Asp Ala Leu
690                 695                 700

Glu Ala Met Ser Ala Leu Leu Gly Asp Leu Asp Arg Asn Thr Arg Ser
705                 710                 715                 720

Asp Ser Val Pro Val Ser Arg Asp Val Lys Gly Val Ala Thr Arg Gln
                725                 730                 735

Ile Ser Val Ile Ser Thr Pro Ile Glu Val Val Lys
            740                 745

<210> SEQ ID NO 48
<211> LENGTH: 927
<212> TYPE: DNA
<213> ORGANISM: Anabena sp.

<400> SEQUENCE: 48
atgaacgcac tctttagcca aggtcatgcc tgtattgttg gggttggatg tgatttaccc    60
aacaccgtag atgatgctgt cggtcttgcc aatatcctca agaccagga acgctgcgct   120 tattcatctg aacaggtaca tttattgact aaagaacagg caaaccgaga gggaatcctt   180
gcagctttag accaattagc tcaatcaact acacctgatt ctacggtaat tgtctatttt   240
tctggacatg gttatcaggt cagtagtccc ataggtgaag cgtattactt aatgcctttt   300
ggctatgatc aaaccaaact acataaaaca gcgattagtg gtgcagaatt tatcaccaag   360
ctacaggcga tttctgctaa aaagctgtta gtcttactgg attgttgcca tgctggtggc   420

-continued

```
ttaggagata catcaaagtt agggtatgaa gcacaaaaag cacccctttcc gccagaggct    480 caagctttat ttaatcaagg gaaaggacga gttgcgatcg cttcctccca agctgatgaa    540
aaatctttcg caggtaaacc ctacagtgct tttacactgg ccttaattga agctttagca    600
ggtaaaggaa cttcgcaaaa agatggttat gtgcgggttg cagatttagc catgtatgcg    660
cgtgaagtcg taccaagaag aacaggcgat cgccagcatc ccattttaaa tttcgagcag    720
gctgataact ttattctggc atactacgca ggtggtgaaa ctgagccgaa aggattaccc    780
tttgaaggtg aaccagaaat tgaacctgaa cctggagctt ttaatcaacc aagtaccaat    840
aattcggtga ttcaagttgt gactcagaaa aattcaaaat acaacatcaa tactggtatg    900
ggtaatacag tgattaacga cagcaat                                        927
```

<210> SEQ ID NO 49
<211> LENGTH: 309
<212> TYPE: PRT
<213> ORGANISM: Anabena sp.

<400> SEQUENCE: 49

```
Met Asn Ala Leu Phe Ser Gln Gly His Ala Cys Ile Val Gly Val Gly
1               5                   10                  15

Cys Asp Leu Pro Asn Thr Val Asp Asp Ala Val Gly Leu Ala Asn Ile
                20                  25                  30

Leu Lys Asp Gln Glu Arg Cys Ala Tyr Ser Ser Glu Gln Val His Leu
            35                  40                  45

Leu Thr Lys Glu Gln Ala Asn Arg Glu Gly Ile Leu Ala Ala Leu Asp
        50                  55                  60

Gln Leu Ala Gln Ser Thr Thr Pro Asp Ser Thr Val Ile Val Tyr Phe
65                  70                  75                  80

Ser Gly His Gly Tyr Gln Val Ser Pro Ile Gly Glu Ala Tyr Tyr
                85                  90                  95

Leu Met Pro Phe Gly Tyr Asp Gln Thr Lys Leu His Lys Thr Ala Ile
            100                 105                 110

Ser Gly Ala Glu Phe Ile Thr Lys Leu Gln Ala Ile Ser Ala Lys Lys
        115                 120                 125

Leu Leu Val Leu Leu Asp Cys Cys His Ala Gly Gly Leu Gly Asp Thr
    130                 135                 140

Ser Lys Leu Gly Tyr Glu Ala Gln Lys Ala Pro Leu Pro Pro Glu Ala
145                 150                 155                 160

Gln Ala Leu Phe Asn Gln Gly Lys Gly Arg Val Ala Ile Ala Ser Ser
                165                 170                 175

Gln Ala Asp Glu Lys Ser Phe Ala Gly Lys Pro Tyr Ser Ala Phe Thr
            180                 185                 190

Leu Ala Leu Ile Glu Ala Leu Ala Gly Lys Gly Thr Ser Gln Lys Asp
        195                 200                 205

Gly Tyr Val Arg Val Ala Asp Leu Ala Met Tyr Ala Arg Glu Val Val
    210                 215                 220

Pro Arg Arg Thr Gly Asp Arg Gln His Pro Ile Leu Asn Phe Glu Gln
225                 230                 235                 240

Ala Asp Asn Phe Ile Leu Ala Tyr Tyr Ala Gly Gly Glu Thr Glu Pro
                245                 250                 255

Lys Gly Leu Pro Phe Glu Gly Glu Pro Glu Ile Glu Pro Glu Pro Gly
            260                 265                 270

Ala Phe Asn Gln Pro Ser Thr Asn Asn Ser Val Ile Gln Val Val Thr
        275                 280                 285
```

Gln Lys Asn Ser Lys Tyr Asn Ile Asn Thr Gly Met Gly Asn Thr Val
    290                 295                 300

Ile Asn Asp Ser Asn
305

<210> SEQ ID NO 50
<211> LENGTH: 2205
<212> TYPE: DNA
<213> ORGANISM: Synechocystis PCC6803

<400> SEQUENCE: 50

| | | | | | |
|---|---|---|---|---|---|
| atgacctttg | accgacggac | atttttacgt | agcggcatgg | ccctgggcct | tggttcctgg | 60 |
| gcctgggcat | ggtccggcag | aaatatgggc | aatccctcg | catccaacac | caatcaaaag | 120 |
| tgggccctac | tgttggcggc | ggggcaaggt | aatggagcca | atggcgatcg | ccggggattg | 180 |
| atgggatgca | ccaccgatag | gcaattgctg | ggggaagttt | aacggggcg | ttacggtttt | 240 |
| gatcaagcca | agattgccgg | gttagacccc | caaggtatta | ccctgtcagc | cctggaaatt | 300 |
| ttatttgatg | agcatctacg | gcaacaggtg | cagaaaggcg | acccagtggt | ggtggccttt | 360 |
| agtggttatg | gcagttataa | ccaccagca | gccatgaccc | caacccgac | ctgggagcag | 420 |
| gctctacccc | atttgggact | atttctagac | ggggaaggag | aggataactt | tctacccctc | 480 |
| actaccctaa | tcaattggtt | gcaatctctc | aaaactaagc | aggtctatct | tgtgctcgac | 540 |
| tgtggtttta | gcactggggt | ggaggagttt | gagggcaatc | tccggggtcg | tagtggcggt | 600 |
| cggggtgggc | caatcccccc | agaagttaac | cccagcaatc | ccccaaccaa | agcaagtttg | 660 |
| ggcaatatca | ccctaattag | tgccactagc | cctgggcaaa | ctgcggtgga | agttcaactg | 720 |
| ggcaagcagt | cagcgggact | attcactttg | gccctcaccc | aaagtctttg | ggaaaatagc | 780 |
| tccaccagtg | tgatggccag | tctgtgggac | catagccgca | atttactggt | tccccgccta | 840 |
| gggacagaac | aaattcccca | atggcgatcg | ccaaataatt | cccctgattt | cctcgctccc | 900 |
| accaccctaa | ccacgggagg | agagggaatg | gtaactggct | taatcagtgg | caattcccta | 960 |
| caaagtcaaa | ttgtggccct | ggctcccctg | gtgcaaaagc | gggctttggt | gcattcctgt | 1020 |
| tatttaactt | ttccagctac | ggagacgggg | agcgatctta | actccacgga | taattccctc | 1080 |
| tggcaagtgc | aaagtgttaa | aggacaaagc | gccacattaa | cggcgatcac | caaaacttca | 1140 |
| tcgaccaagg | ccgagtcagc | gacatcctca | acggaagcca | atggcgggga | agcaaaaaag | 1200 |
| gaaatgctgg | tgggcagtgc | cctgcgggaa | atataccgag | ctatccctaa | aaacctcgct | 1260 |
| ttaacagtgg | ccctagccca | tgacctggaa | cgcattgagc | gggtggatgc | caccagtgcc | 1320 |
| tttggggcga | tcgccgccgt | ggaaacagtg | attaatgccg | ggaaggtag | tgcagactgt | 1380 |
| gtgtttggca | gactgaagc | ccatcgctat | agcctctta | ccgaggggg | aaacccttg | 1440 |
| caaccccctga | ctaagtctga | gtccagcggg | gcggtgaaaa | ctgtcattgg | tgccctagac | 1500 |
| ccctgcttga | accgtttgct | ggccttgaaa | tggctgacct | tactggccaa | tggcaatagc | 1560 |
| acccaactgg | gggccggcat | caaactggtg | caacaaacca | gcggcgataa | tcccctgccc | 1620 |
| cgcctaattt | accaatggcg | atcaacccgt | taccectatc | ctccccagga | caacaacccc | 1680 |
| ggcaatgggg | gcaatggcat | acccaatgct | ccccccagct | tcctgcccgc | cgtggccacc | 1740 |
| aaccaagctt | tacagtgtga | attggaaaac | tttagcaatg | aaaccctcta | cggttgtttg | 1800 |
| attgggtga | ataatcgcgg | tctgagtgtg | cggccattc | tccgtccaga | cctaaagtta | 1860 |
| ctacagggca | aagaacaact | gacctggcct | agcccagaag | atccctctg | gattattggt | 1920 |

-continued

```
ggagacaagg cgatcgccca ttggtttta attctttccc gttttccccct ggccggcact    1980 gccacagccc taggacaaca aatcaccggc aacaattcca tcgatccccc cagcctagaa    2040
agccatcccc cccgggtgct gccattgaaa aatttgctcc ctgtggtact agccctggtc    2100
caagacctaa ccgcccatgg ggtgacggtg gccccagtcc ctgacgatat gattttacta    2160
tccaccgccg attggttaag tctgcccatt atgtatcaag tcatt                    2205
```

<210> SEQ ID NO 51
<211> LENGTH: 735
<212> TYPE: PRT
<213> ORGANISM: Synechocystis PCC6803

<400> SEQUENCE: 51

```
Met Thr Phe Asp Arg Arg Thr Phe Leu Arg Ser Gly Met Ala Leu Gly
1               5                   10                  15

Leu Gly Ser Trp Ala Trp Ala Trp Ser Gly Arg Asn Met Gly Gln Ser
            20                  25                  30

Leu Ala Ser Asn Thr Asn Gln Lys Trp Ala Leu Leu Ala Ala Gly
        35                  40                  45

Gln Gly Asn Gly Ala Asn Gly Asp Arg Arg Gly Leu Met Gly Cys Thr
    50                  55                  60

Thr Asp Arg Gln Leu Leu Gly Glu Val Leu Thr Gly Arg Tyr Gly Phe
65                  70                  75                  80

Asp Gln Ala Lys Ile Ala Gly Leu Asp Pro Gln Gly Ile Thr Leu Ser
                85                  90                  95

Ala Leu Glu Ile Leu Phe Asp Glu His Leu Arg Gln Gln Val Gln Lys
            100                 105                 110

Gly Asp Pro Val Val Val Ala Phe Ser Gly Tyr Gly Ser Tyr Asn Pro
        115                 120                 125

Pro Ala Ala Met Thr Pro Asn Pro Thr Trp Glu Gln Ala Leu Pro His
    130                 135                 140

Leu Gly Leu Phe Leu Asp Gly Glu Gly Glu Asp Asn Phe Leu Pro Leu
145                 150                 155                 160

Thr Thr Leu Ile Asn Trp Leu Gln Ser Leu Lys Thr Lys Gln Val Tyr
                165                 170                 175

Leu Val Leu Asp Cys Gly Phe Ser Thr Gly Val Glu Glu Phe Glu Gly
            180                 185                 190

Asn Leu Arg Gly Arg Ser Gly Gly Arg Gly Gly Pro Ile Pro Pro Glu
        195                 200                 205

Val Asn Pro Ser Asn Pro Pro Thr Lys Ala Ser Leu Gly Asn Ile Thr
    210                 215                 220

Leu Ile Ser Ala Thr Ser Pro Gly Gln Thr Ala Val Glu Val Gln Leu
225                 230                 235                 240

Gly Lys Gln Ser Ala Gly Leu Phe Thr Leu Ala Leu Thr Gln Ser Leu
                245                 250                 255

Trp Glu Asn Ser Ser Thr Ser Val Met Ala Ser Leu Trp Asp His Ser
            260                 265                 270

Arg Asn Leu Leu Val Pro Arg Leu Gly Thr Glu Gln Ile Pro Gln Trp
        275                 280                 285

Arg Ser Pro Asn Asn Ser Pro Asp Phe Leu Ala Pro Thr Thr Leu Thr
    290                 295                 300

Thr Gly Gly Glu Gly Met Val Thr Gly Leu Ile Ser Gly Asn Ser Leu
305                 310                 315                 320

Gln Ser Gln Ile Val Ala Leu Ala Pro Leu Val Gln Lys Arg Ala Leu
```

```
                    325                 330                 335
Val His Ser Cys Tyr Leu Thr Phe Pro Ala Thr Glu Thr Gly Ser Asp
            340                 345                 350
Leu Asn Ser Thr Asp Asn Ser Leu Trp Gln Val Gln Ser Val Lys Gly
            355                 360                 365
Gln Ser Ala Thr Leu Thr Ala Ile Thr Lys Thr Ser Ser Thr Lys Ala
            370                 375                 380
Glu Ser Ala Thr Ser Thr Glu Ala Asn Gly Gly Glu Ser Lys Lys
385                 390                 395                 400
Glu Met Leu Val Gly Ser Ala Leu Arg Glu Ile Tyr Arg Ala Ile Pro
                405                 410                 415
Lys Asn Leu Ala Leu Thr Val Ala Leu Ala His Asp Leu Glu Arg Ile
                420                 425                 430
Glu Arg Val Asp Ala Thr Ser Ala Phe Gly Ala Ile Ala Ala Val Glu
                435                 440                 445
Thr Val Ile Asn Ala Gly Glu Gly Ser Ala Asp Cys Val Phe Gly Arg
                450                 455                 460
Leu Glu Ala His Arg Tyr Ser Leu Phe Thr Glu Gly Gly Asn Pro Leu
465                 470                 475                 480
Gln Pro Leu Thr Lys Ser Glu Ser Ser Gly Ala Val Lys Thr Val Ile
                485                 490                 495
Gly Ala Leu Asp Pro Cys Leu Asn Arg Leu Leu Ala Leu Lys Trp Leu
                500                 505                 510
Thr Leu Leu Ala Asn Gly Asn Ser Thr Gln Leu Gly Ala Gly Ile Lys
                515                 520                 525
Leu Val Gln Gln Thr Ser Gly Asp Asn Pro Leu Pro Arg Leu Ile Tyr
530                 535                 540
Gln Trp Arg Ser Thr Arg Tyr Pro Tyr Pro Gln Asp Asn Asn Pro
545                 550                 555                 560
Gly Asn Gly Gly Asn Gly Ile Pro Asn Ala Pro Pro Ser Phe Leu Pro
                565                 570                 575
Ala Val Ala Thr Asn Gln Ala Leu Gln Cys Glu Leu Glu Asn Phe Ser
                580                 585                 590
Asn Glu Thr Leu Tyr Gly Cys Leu Ile Gly Val Asn Asn Arg Gly Leu
                595                 600                 605
Ser Val Ala Ala Ile Leu Arg Pro Asp Leu Lys Leu Leu Gln Gly Lys
                610                 615                 620
Glu Gln Leu Thr Trp Pro Ser Pro Glu Asp Pro Leu Trp Ile Ile Gly
625                 630                 635                 640
Gly Asp Lys Ala Ile Ala His Trp Phe Leu Ile Leu Ser Arg Phe Pro
                645                 650                 655
Leu Ala Gly Thr Ala Thr Ala Leu Gly Gln Gln Ile Thr Gly Asn Asn
                660                 665                 670
Ser Ile Asp Pro Pro Ser Leu Glu Ser His Pro Pro Arg Val Leu Pro
                675                 680                 685
Leu Lys Asn Leu Leu Pro Val Val Leu Ala Leu Val Gln Asp Leu Thr
                690                 695                 700
Ala His Gly Val Thr Val Ala Pro Val Pro Asp Asp Met Ile Leu Leu
705                 710                 715                 720
Ser Thr Ala Asp Trp Leu Ser Leu Pro Ile Met Tyr Gln Val Ile
                725                 730                 735

<210> SEQ ID NO 52
```

```
<211> LENGTH: 228
<212> TYPE: DNA
<213> ORGANISM: Artificial Sequence
<220> FEATURE:
<223> OTHER INFORMATION: Microcystis pemI gene codon-optimized for
      Synechocystis

<400> SEQUENCE: 52
atgttatctt ctctgataat tgaactggaa caaaagttac gagactgttc tcttgaagat      60
aaacaatggt tattggagca gttacatcaa caattaggat tgaataatca aaaaacaact     120
aaacaacgat taatagatag ttggaatgaa gcttatagtg atggattgga cgaatcagaa     180
actttaatgt tagagcgaat acggcatcat caaagccaat tatctgag                  228

<210> SEQ ID NO 53
<211> LENGTH: 354
<212> TYPE: DNA
<213> ORGANISM: Artificial Sequence
<220> FEATURE:
<223> OTHER INFORMATION: Microcystis pemK gene codon-optimized for
      Synechocystis

<400> SEQUENCE: 53
atgacgattt ttcaaggaga gatttattgg attgatttag gagaaccaca aggttctgaa      60
cctgcttatc ttcgtccttg tgttgtggtg caaaatgatg ctctgaatca gtcacaaatt     120
gggacggtta ttgtgtgtcc attaacaacc aatttgagac gagcaaaagc tattggtaat     180
gttttattga atgagggtga agggaattta ccagaatcca gtgttgttaa tgtttcgcag     240
gttttcacgg ttgataagcg tcttttaaca gagtctatcg gaagactttc tcgggaaaaa     300
atcaaattaa ttattcaggg aattaatttg gttattgaac ctcaagaact cgaa           354

<210> SEQ ID NO 54
<211> LENGTH: 587
<212> TYPE: DNA
<213> ORGANISM: Artificial Sequence
<220> FEATURE:
<223> OTHER INFORMATION: Microcystis pemI-pemK operon codon-optimized
      for Synechocystis

<400> SEQUENCE: 54
atgttatctt ctctgataat tgaactggaa caaaagttac gagactgttc tcttgaagat      60
aaacaatggt tattggagca gttacatcaa caattaggat tgaataatca aaaaacaact     120
aaacaacgat taatagatag ttggaatgaa gcttatagtg atggattgga cgaatcagaa     180
actttaatgt tagagcgaat acggcatcat caaagccaat tatctgagta aatatgacga     240
tttttcaagg agagatttat tggattgatt taggagaacc acaaggttct gaacctgctt     300
atcttcgtcc ttgtgttgtg gtgcaaaatg atgctctgaa tcagtcacaa attgggacgg     360
ttattgtgtg tccattaaca accaatttga gacgagcaaa agctattggt aatgttttat     420
tgaatgaggg tgaagggaat ttaccagaat ccagtgttgt taatgtttcg caggttttca     480
cggttgataa gcgtcttttta acagagtcta tcggaagact ttctcgggaa aaaatcaaat     540
taattattca gggaattaat ttggttattg aacctcaaga actcgaa                   587

<210> SEQ ID NO 55
<211> LENGTH: 82
<212> TYPE: DNA
<213> ORGANISM: Artificial Sequence
<220> FEATURE:
<223> OTHER INFORMATION: Tet promoter for plasmid pBR322
```

<400> SEQUENCE: 55

| tcatgtttga cagcttatca tcgataagct ttaatgcggt agtttatcac agttaaattg | 60 |
| ctaacgcagt caggcaccgt gt | 82 |

<210> SEQ ID NO 56
<211> LENGTH: 1000
<212> TYPE: DNA
<213> ORGANISM: Nannochloropsis gaditana

<400> SEQUENCE: 56

| actgaagata ctcaggatat cgtcttaatt ttaccgacca acaaatatac acagcaccaa | 60 |
| cgcatccaca cgtggaggct tccgcatcaa gacatcgctt tacatgtgtg tggaggcttc | 120 |
| cgtcgcgtcg ccggcgtggg gacgtgcttg gtgcgtcccg gtgtcctttt ttcgagccca | 180 |
| gaccgataag aaatatagag aagagtcgag gccgggccgt tgcggtgctg ctcgttgacc | 240 |
| tctggcgggg accgcgggga ttaccaacac cacctaaagc gcttccatgg acggtaattt | 300 |
| gtggtttctt catttacaaa atcttggtat actttctcac ttgtcatttt ttgcggtcca | 360 |
| ctcgcgtggt atggaccatc agcgcacatt tctgggcctt cccggggcgc atgcgcagtt | 420 |
| ggacaggcgc tgattgtatg tctgatgctg ggaagtatgc gggcttttgtt cgattgttca | 480 |
| ggcttgatca cgcgaccaaa ggcttgaaaa cgtacactat acggccccaa ttgaagcctc | 540 |
| ttttcacccct cggagttcct atgtgactct gagaaatgtg cccacccgct aacatagttg | 600 |
| cccgcgttcc ttgcgtgttt agtagcaagg tatttacgag gcggccgtat catatgctgt | 660 |
| aaagcagcat ttcttcacca ctcctacctc ccgatccctt caaaaatgtg cctcttcata | 720 |
| gaaaaggagc tccatgatgc atgtagagtg taaaagtgat actcaacgtg tcgcgcgtga | 780 |
| agtgctgtcc tacgctcctg cagtggacct cagtaggact ggccatgtca tgccatggat | 840 |
| gtttcgcgac atccccgtt atccccgcct atcttttaa gatttgtgcg tgtgagcctc | 900 |
| acaggatgac aatccaggcg cactgcgctc gcaagtgtgg aagcctttgc cttgcattag | 960 |
| acaaggctat gtaaatattg tcggtaccaa agtgacgggc | 1000 |

<210> SEQ ID NO 57
<211> LENGTH: 1000
<212> TYPE: DNA
<213> ORGANISM: Nannochloropsis gaditana

<400> SEQUENCE: 57

| ggttaagtcc ggactcaacc ccggtgaact atctctgaag cggctctggg cggcccgcgt | 60 |
| gcgttgtcaa gcctccagaa accaagcgag gctttgtttg ctatgtacgg gttggaacag | 120 |
| ggttggaggg aaaggtgttt tgaggagggt acgtaatga cggaattgta tcgtttctca | 180 |
| gtgggatgga gggccttcc cagtcagcaa aatagaaccc ttacgactga gtccgacgcc | 240 |
| gcgagcggca ctgtcgagag acgacgcaag caagggagga gaaaaggtgt agactcttcg | 300 |
| cttttgcagg catgcaccaa ctttatttat ggtaccttcc atgcgatgca gcagtgccga | 360 |
| gctggggagg gagctacggc ttacaaaata gggaagtcgc agcccatctg tcacatcccc | 420 |
| cggccgaccc gcgagtatcc cacacaccgc aatccaccat ctacataatc atacgcccgg | 480 |
| gagacacatc cgcaaacatg ccgccgatcg ccgtggcgtg cagtaggtaa cccgaaccct | 540 |
| aaccctagca gggagaccgt gccaaaaaag tcgagccgtt aaaaggtgga ggccccaggc | 600 |
| cggcggggtt tcggacgtgc cgggaggttg gatcctatgc tgcaaaaggt catgcacgca | 660 |
| actctggcgt cctggcgcgc ccccgacgtg tcccgttgcg tatcataagg gcccagtttg | 720 |

| | |
|---|---|
| gaagagacgc gggaaaggaa ttgattttgg cgccagcgat agagacagga gagcggaata | 780 |
| cgaacatctg gatttccgtc ctcaaaatgc cgctccatct tcttgttgta caaaactatc | 840 |
| aacttcgccc gcaacttctt caaaaaaagg ccaaattggt cgattttttt atcttttgac | 900 |
| atacgaaatt tcttctcacc cacgcgtaat cggtttttac agtaaaaatc acctgcaaac | 960 |
| tgcaacttcc atttccccgc ttcaagttcc cgtgagaaaa | 1000 |

<210> SEQ ID NO 58
<211> LENGTH: 1000
<212> TYPE: DNA
<213> ORGANISM: Nannochloropsis gaditana

<400> SEQUENCE: 58

| | |
|---|---|
| gaacgtggac cacctggttc tgggcaccac gcagtacaaa cctcaagaat cgcagaacg | 60 |
| gatgctgaat ctaaaagtga cgaacatgtg ggggatcatc aagtggttgt gcgacaaatt | 120 |
| cctttcgcct gagagcagct tggagtcggg gaagtatgtt ctacttaaag acccgaacaa | 180 |
| gccgaccttg cggatttatg cggtacccctt ggacgcgttc gaaggggatg aagaggacga | 240 |
| ggacgaggac gaggacgaag acgaggagta tgatgacgat ggagcaccag acaagacctc | 300 |
| gggacgggat ggagaggagg aggaagaaga agaggacaca ggggcaaaac atcgtcaatt | 360 |
| ttcggggccg cctcaaacag gaccagtaat ctaagagagg aaggcaagaa agggaggtag | 420 |
| tgcagagccg ggaagggtg aggggagagt tgtagtttgc ttttcttgaa agacaaaaca | 480 |
| caagaacatt gaatatgatc ggtatgcgaa acgaaaattg attttgcgag cctgcacttc | 540 |
| agacgtgaag gcctgtcttt caacctcccg ccgtgagacc atctgggatt tcttttctc | 600 |
| cgaacaagtc actactcaca gagaagaatt taaaattcat gctaataccg caacacaatg | 660 |
| atggtcatcc agaagacatc acacatcccc tggtgcacga aaaggtcctt gaaggatttt | 720 |
| tttgcgagga gagaaaatcc ccgctaaacc gacgggaaac ttcaaatcca acttaatccc | 780 |
| cgaaagtcct acccccccggc accgtctctt tcaagcaaat gttttgcaaa ctcaagctcg | 840 |
| aaggctgatt aattgatgag ttttggtgtg tttggtgtac atgtataccct ttagaacgat | 900 |
| tgaaatctga cataacaaga gcttttgcga tgggaattgt gcaacggcaa attcttgtta | 960 |
| ccctcttttt cactttcccg acattcgcac aggtagcgct | 1000 |

<210> SEQ ID NO 59
<211> LENGTH: 1000
<212> TYPE: DNA
<213> ORGANISM: Nannochloropsis gaditana

<400> SEQUENCE: 59

| | |
|---|---|
| atagatgaag acgatagggt tcaggatgga gatgaggaaa aaaaaaaaag gaaaaatcca | 60 |
| caacatccac aacgaccgtg ctcgctacac aatacgagat tcttactgga gcggagcact | 120 |
| aaaatgtcat gtgtttgatg aaattactgt tcttagttca ctcaaatgcg tccaggctcc | 180 |
| gaactaaccg gcctggagag agaaattcaa aatttcaaat cgtcggtcga tgcctgcggg | 240 |
| cgggccgccc ctgttacttt ctgacacaaa aaacaattgc cgcagtggac cgtgcgaagg | 300 |
| caacattgtt gcaagaacga tgtgtgttga gagcttgttt tgatagagtg ggcggagcgg | 360 |
| gcccatgaag atatataatg ctcgtaatca gtcagacgaa caatatattc tgccgctagt | 420 |
| atccatggca agacgcgacc ccgattgatg tcccatggcc cttttttcctg ttgccttcaa | 480 |
| catttccccc cttcaatgcc cgctcttgca aacgagtctg tcatgtgcct atggacatgt | 540 |

-continued

```
cctgtaaaca cagaaatgag tgacgcacgt tcatagtact tccctcgtag gaggttgcga    600
gagaacaaca cttcagcacc tgtgtattca ccgactcccg caagatggga ggccttccgc    660
tgctgggacc tatccaacca taacacccttt tcctgaactt atttattctt agatcattga   720
tcgtgcacta aggctggtag cagcaaaaca ggccactctt ggagtggtaa aggaaagcgc    780
cagctcaagt ggcacggatc cacagcaagc ggaacactcc ctgcaagaca gttgaaatag    840
ccgcctcgtt ttgtaagagg gtgctcaagc tcctcttttt cacattttct acgcgacctc    900
ggaggtttaa aacgagagaa tatttatttc accgtaaaag ggtacaaagg ggctcttgcg    960
ccctgtctcg ggcacccttc tttgtgctga gacggtacaa                         1000
```

<210> SEQ ID NO 60
<211> LENGTH: 1000
<212> TYPE: DNA
<213> ORGANISM: Nannochloropsis gaditana

<400> SEQUENCE: 60

```
ggggtagaaa agacagaaga ttaactctga ggatggtgag ggacaagaac gtccttatca     60
tcaaacacga aagggaagct atgtcttgag catacgcgac tcttgtttgt cgcctgtaga    120
gcagctcgca ttcctcgaaa atcggtacgg agatacagcg ctttagcact ttaggagcag    180
tacatcaagc gacaggggct cgatagacag aaaggattgc tccctcgtag tcggaacagc    240
accggatgcc atattgctgc tctctagtgg cgtaaacggc tacaacatgc ttgtcagcaa    300
aaaatgtaag gagatagtgc aattagcact atgtaactgt gtgcaaagct gttaatcgga    360
cggtggctgt gggagttgtt ggaagcaccg tacaggtatt tgttccatac aaccgttcaa    420
ataagcgtca ttgtgaggga tttgacccat acggtgcgtc gtacggtttg aagaccctgc    480
gcagtaacag ataatcccat atgaaagcgg tcgtagcagc agctgtagac aaaaacaaag    540
ccatgaaatg gtcaaatgga atccgtgtac attttttagtt catcgtgtct tgcgtttatc    600
ccttgtactt caaccgtagc cgcttaaaaa ttgcagtggc accctgtctc tagggatgca    660
atgcgtgatt tacttaactg ggtaaattac gggcagcttt aaacagacct caaaagcaaa    720
cagcttcact gtctacatgt cgcgtcatat atcctctcta gcgtcccaaa acaagaatt     780 tactctatca tgactttgtc agtctacgct gactgacaga ctgcgggatc aattccacga    840 ctatccccc caaaaatccg aaaagagaat gaatagaagc acatacgggca ccccattttt    900 acccatggaa taggactgtc ctgaccatca atatccttga ggcccttaca ttctataaca    960
tgaagagatt atgtaaaagg gacgttgtca gccaatcggc                         1000
```

<210> SEQ ID NO 61
<211> LENGTH: 1000
<212> TYPE: DNA
<213> ORGANISM: Nannochloropsis gaditana

<400> SEQUENCE: 61

```
ccttcgcggc ttcatcgcta gctaacatgg catccgagag cccctttgcg agaaggaaaa     60
taagacgatt ggcatacagc aattgcggac aagggtagaa acgtttcatg ggcagccaac    120
gaacaagtgc tccataaatt gttaatttag gcattcatgt gcacaggaac agctcgcaat    180
tctctgctct tacccgcaat atgaggtcta gagaacgacc cacgccgtcc agaccgagca    240
gacggctctg gattgtgtac tgtgggggga aaaactctgc accgaaaatg tctacgaaga    300
ccgggtcccg cctataggat tgcttttctg atttatcatg ttgaaagcag gaagtggtca    360
gttttttatt taccgcattg ctaagaaaat tccccccaat aaactccatc acttcctgct    420
```

```
atcgaataaa aagcctacct gttgataaag tattgcgcct caaaattgag ctcatcctcg    480
cagcacgtta agtatgacca gaaagagctg tcctatgact gtcaggtcga tgatgatcgg    540
cctcgaactt tttacccttc gctctcgtgg agctcttaga cagcctcgcc gcacgatgag    600
ggcgttcaat ttgagagacg acaaggagac aggtgatgtg gctgtttcca agacgcgatg    660
aaacctgcag ggtggcagtg cctcatgata tgagacaggg agcgcaacat gtccgggcca    720
gggagaaggt tgaaggccgg gcagacgttt gggcgagggc ccacgccgcc aaccgatccg    780
agccgttgat caacctcccc accgagaaat tccagccgg gccagttgcg taaaaacacg     840
ttcgagggag cattcgtaga acatttccct tcttagcttt tccatgaatg aagcataagg    900
atcaggatta agatgtcaag gtgaaaaacc aagcaaaaaa cgtggtcagc cgtctacgtc    960
caccattgta cctttttagca aacaatacag agcacgagaa                         1000
```

<210> SEQ ID NO 62
<211> LENGTH: 1000
<212> TYPE: DNA
<213> ORGANISM: Nannochloropsis gaditana

<400> SEQUENCE: 62

```
catgcagcac agccttgcag ctgaatatgg acgacatgaa aacagaccgt actttgacaa    60
gcttcctcta atgcttttac gtagcttgtc cagtgtattt tgtcttttc gttcctagaa     120 gtatgtttct tatcatggtg ctccccatga gaggttgcga gacagattag ttttatacga   180
cacaggtgta cattgcctct gcgagatgcc tagcccgtac tgtgaattca aaattgtcct   240
gagatatcca ctctttacat gacacaatct gatagccgtg ttcgccgcaa gtcaaccttt    300
gcctccgtac gcccgcaagg cggggctcgg aactccgaga agattgtga cgtcacactg     360 ttcgtcaact gccggcgccg acgtggacct gcggccatag gatctccttc atctcgagcc   420
cgaaagtcat aaagggtgac ggggacgggg cggcttgcgg cttctggttt ttcttatgtg   480
catatgtggt gtacatgctg tccagtgcag gcatattagc tccttgcatt tttacgcgtg   540
gcgaactttt atgacaggaa acctagcgtc accgcatgag cactcggtgt tccaagtgga    600
tgaagttata attatgccat ggcactgcat atcggcagga tatgtaaagg gtgctccatt    660
aaagacatga agacaatgac ttccagcagt attgctcact tttccttcc aacatactc     720 ctcctgcagg caggccacct ccctggcttc tccctgaagg cctgacctga cacccccttt   780
tggcacgttt caccccaagc cctgcacctc cagacaccgt cagtgtgtta aaaccctgct    840
gttgtcgtgg caggctcgcc tacgccgtgg tcgtcgtctg tggcttgaaa gccttcgcca    900
ttttaaagaa gtgtttggca ataatttacg ctttagactt cgttgtcacg acaatacta    960 gcaccacatc gcgacacctc ccacatacaa tccttgtgac                         1000
```

<210> SEQ ID NO 63
<211> LENGTH: 1000
<212> TYPE: DNA
<213> ORGANISM: Nannochloropsis gaditana

<400> SEQUENCE: 63

```
gcatgcacaa aagtttggac atcatccgga aggtcagtaa gctctacagc tgtgtcttcg    60
tgttgcccat tgacttcagt tgcgagcagc aacaggcggt gtgtatcgcc gccatcttca   120
ggctttacga tcccttcac gtgccggagt cgaagcagat gtggttgtaa ttgtttgacc    180
gcggaattgc aatatttcgc aggaagacgc aaggctgcca cacgtaaagt tcgcctaaaa   240
```

```
gcgctaggat ccagcgacac ctcttcatgt gcatcaggat gggagacagc atcagaggtg    300
tctgacctcg cagggatggt accagtggga ctcatgctgc acaggtcgct gtcctcagtc    360
tgcggatgga attagaaaca aattattgac ctcgtcctat atgaaaagaa tccattgaca    420
ccgttttgcc caaaaaatgc gacggaaagt cgcctccggg gctttgtagg cctccatggc    480
cgggcgggga gacggcgagt ggctgcattt tatgggcgg caagcagcga gggccgttgg     540
aggagggagg aggttaaaag ttagcctttg agacccggaa acagtgatcc agaatggtga    600
ttgagcaatt atgaagcttg atatggattg attaaaacca atttgacaat gcggtggtaa    660
taagtctggt ggaaatgcag gtaattttta gatcttggcc tagcaaacgc atggcgtcac    720
aagttgatct tccaagggcc atgtgttctt cgtttatctc cctctggttc aggttcacgc    780
tctttcttca gcgtacgagt ggcatgtgtt tctttttttg ccggttaaat atgtttcaaa    840
aaccgtcgac aacagtaata acgcatactc tagcgcgagt gagcaattgt tgcgtgataa    900
ttcttactga atctgcagtc ctcactgccg ggtcgtgaca tgtcccttcc ttctcaatga    960
aaagcaccca gcgacctcga gtcaaacaaa caccaccacc                        1000
```

<210> SEQ ID NO 64
<211> LENGTH: 1000
<212> TYPE: DNA
<213> ORGANISM: Nannochloropsis gaditana

<400> SEQUENCE: 64

```
atcctttaaa tatatagcgg tggtcacgtt acgtcaggat gagtcgagtg tggggtttga     60 gtttttgcg gttccttgct atatgttgag aagatggata aaatagagaa attccgcgaa    120
aggaggtgaa atggaagaaa gttatcggta cgcgagagcc aattatcgga aaagcctctg    180
tgcaattaaa tacatgtgcg cagtttaatt caatattcgg gtattgaaag attgctctgt    240
tcactcttta ggaaaattga ttgaaatttt tcttgtcttg ggggggggag ggagggctgg    300
cttttatcac cgtcgttgtg aggtacgctc ctgaaaaaaa catcctaagc attttcatgt    360
ccaaatatca ctttcgaaaa cgatcaagtg ctattcccca tttaaaagat attttttggaa   420 aatgatttct ccttttttgga cattaaatcc cgtatttttgg tggctgtgaa agtaattttt   480
tcttatgcgg ggggttcggg cttttttgttt tcaggatgct tcaacggcac acgtccgtcc   540
acgcgctgtt tattgaaatc gcaggcacac gcacacacat tgtgttttgt acctgacca    600 ccaacacata tgtttgctat acgacggaaa attttttttag cgtgcggtat gattttgtgg   660
tcatcgtgct cgtttggagg tatttctttt caagcgtgtt gcgaatgctc atcagaaatg    720
catttgttcc tgtggcgtgc ctggcgcgtg caaatttctc agattgaagc cctttctggt    780
ccggaaaggt atggtagaag tagacttttt catatcaacc cataaaaaca ttgtatttcg    840
tttcagtttg caacttttat gctatgccat ttttaatata ttcgacagtg tcccactcat    900 atgccccttct cttttttttcct cattcttcac acactttatt ccccatgata tctctcattc   960
tttagacatc tctttcaagt accttctcaa atccaaaccc                         1000
```

<210> SEQ ID NO 65
<211> LENGTH: 1000
<212> TYPE: DNA
<213> ORGANISM: Nannochloropsis gaditana

<400> SEQUENCE: 65

```
aatacagcat ccattgtcat acatcaagga cccagtttgc ttgcggccat gcttcttcgc     60 aggaaaattcg caggactgga ttatttccgc tttggaagtg ttcgctcttt aatgttcggc   120
```

-continued

```
caagtgaatc ttggcccgac ggctacttac gcccctccaa acaatcgaat ctcgtccaag      180
gaaactttaa tcttgtccat gcggtcggac aatgccatgc attaaatgaa ttgaatcgta      240
atcatgtggt gtagacagtt acattttgga ggagggaatc gaatcatgat tgatgcttga      300
atgtgctgaa aggctccctg tatggcgttg attatctccg acaagcgtg gaaagatgtt       360
gcagaagtca tggattaaga tttaagccct cctaaacgtt gtcgtccgaa ggaagtgatc      420
atcgtcgaca aggactttgc aaggatcggg gaaataaatt tacccttcca tgatatgcaa      480
tcccgtcgcc tcgtattgtc ttacggtcat gagttcaggc accagttgtt gagcggttcg      540
ttgcttctag tgaccagggt gtgacgaatt tgcgtcgtaa tagcatcgtc cgccatgttt      600
gagtgtgaca aacgtgactg acttgacagc ttgcgtggcc tggggaggct gggcgtcga      660
gcacagggaa tagagagact cgttgatgct ggaggggggg ttgaggttga cttgtattca      720
ccaccactca taccctatgc gtggttgcct taaagtcttg aaaggtacat cgcatacacg      780
caaaatagat tttgatcgcc tcgcacatgt cctctttcat ccattttgt tgggttctag       840
gaggcaacgg cttgggcgcc acagctccat tattccctcc accccgagac ttgcgcttct      900
gtatcaaaca gttgcgccgt gctctggctg ccagaggttt caagttacat acattctcag     960
gttctgaaac cgctgcagcc tcttggaggg ataTaggagg                           1000
```

<210> SEQ ID NO 66
<211> LENGTH: 249
<212> TYPE: DNA
<213> ORGANISM: Escherichia coli

<400> SEQUENCE: 66

```
atgatccaca gtagcgtaaa gcgttgggga aattcaccgg cggtgcggat cccggctacg       60
ttaatgcagg cgctcaatct gaatattgat gatgaagtga agattgacct ggtggatggc      120
aaattaatta ttgagccagt gcgtaaagag cccgtattta cgcttgctga actggtcaac      180
gacatcacgc cggaaaacct ccacgagaat atcgactggg gagagccgaa agataaggaa      240
gtctggtaa                                                              249
```

<210> SEQ ID NO 67
<211> LENGTH: 82
<212> TYPE: PRT
<213> ORGANISM: Escherichia coli

<400> SEQUENCE: 67

```
Met Ile His Ser Ser Val Lys Arg Trp Gly Asn Ser Pro Ala Val Arg
1               5                   10                  15

Ile Pro Ala Thr Leu Met Gln Ala Leu Asn Leu Asn Ile Asp Asp Glu
            20                  25                  30

Val Lys Ile Asp Leu Val Asp Gly Lys Leu Ile Ile Glu Pro Val Arg
        35                  40                  45

Lys Glu Pro Val Phe Thr Leu Ala Glu Leu Val Asn Asp Ile Thr Pro
    50                  55                  60

Glu Asn Leu His Glu Asn Ile Asp Trp Gly Glu Pro Lys Asp Lys Glu
65                  70                  75                  80

Val Trp
```

<210> SEQ ID NO 68
<211> LENGTH: 336
<212> TYPE: DNA
<213> ORGANISM: Escherichia coli

<400> SEQUENCE: 68

```
atggtaagcc gatacgtacc cgatatgggc gatctgattt gggttgattt tgacccgaca      60
aaaggtagcg agcaagctgg acatcgtcca gctgttgtcc tgagtccttt catgtacaac     120
aacaaaacag gtatgtgtct gtgtgttcct tgtacaacgc aatcaaaagg atatccgttc     180
gaagttgttt tatccggtca ggaacgtgat ggcgtagcgt tagctgatca ggtaaaaagt     240
atcgcctggc gggcaagagg agcaacgaag aaaggaacag ttgccccaga ggaattacaa     300
ctcattaaag ccaaaattaa cgtactgatt gggtag                               336
```

<210> SEQ ID NO 69
<211> LENGTH: 336
<212> TYPE: DNA
<213> ORGANISM: Artificial Sequence
<220> FEATURE:
<223> OTHER INFORMATION: mazF toxin, sequence altered for toxin
    resistance

<400> SEQUENCE: 69

```
atggtaagcc gatacgtacc cgatatgggc gatctgattt gggttgattt tgacccgacc      60
aaaggtagcg agcaagctgg gcatcgtcca gctgttgtcc tgagtccttt catgtataat     120
aataaaaccg gtatgtgtct gtgtgttcct tgtaccacgc aatcaaaagg atatccgttc     180
gaagttgttt tatccggtca ggaacgtgat ggcgtagcgt tagctgatca ggtaaaaagt     240
atcgcctggc gggcaagagg agcaacgaag aaaggaaccg ttgccccaga ggaattgcaa     300
ctcattaaag ccaaaattaa cgtactgatt gggtag                               336
```

<210> SEQ ID NO 70
<211> LENGTH: 111
<212> TYPE: PRT
<213> ORGANISM: Escherichia coli

<400> SEQUENCE: 70

```
Met Val Ser Arg Tyr Val Pro Asp Met Gly Asp Leu Ile Trp Val Asp
1               5                   10                  15
Phe Asp Pro Thr Lys Gly Ser Glu Gln Ala Gly His Arg Pro Ala Val
            20                  25                  30
Val Leu Ser Pro Phe Met Tyr Asn Asn Lys Thr Gly Met Cys Leu Cys
        35                  40                  45
Val Pro Cys Thr Thr Gln Ser Lys Gly Tyr Pro Phe Glu Val Val Leu
    50                  55                  60
Ser Gly Gln Glu Arg Asp Gly Val Ala Leu Ala Asp Gln Val Lys Ser
65                  70                  75                  80
Ile Ala Trp Arg Ala Arg Gly Ala Thr Lys Lys Gly Thr Val Ala Pro
                85                  90                  95
Glu Glu Leu Gln Leu Ile Lys Ala Lys Ile Asn Val Leu Ile Gly
            100                 105                 110
```

<210> SEQ ID NO 71
<211> LENGTH: 258
<212> TYPE: DNA
<213> ORGANISM: Escherichia coli

<400> SEQUENCE: 71

```
atgcatacca cccgactgaa gagggttggc ggctcagtta tgctgaccgt cccaccggca      60
ctgctgaatg cgctgtctct gggcacagat aatgaagttg catggtcat tgataatggc     120
```
cggctgattg ttgagccgta cagacgcccg caatattcac tggctgagct actggcacag    180
tgtgatccga atgctgaaat atcagctgaa gaacgagaat ggctggatgc accggcgact    240
ggtcaggagg aaatctga                                                  258

<210> SEQ ID NO 72
<211> LENGTH: 85
<212> TYPE: PRT
<213> ORGANISM: Escherichia coli

<400> SEQUENCE: 72

Met His Thr Thr Arg Leu Lys Arg Val Gly Gly Ser Val Met Leu Thr
1               5                   10                  15

Val Pro Pro Ala Leu Leu Asn Ala Leu Ser Leu Gly Thr Asp Asn Glu
            20                  25                  30

Val Gly Met Val Ile Asp Asn Gly Arg Leu Ile Val Glu Pro Tyr Arg
        35                  40                  45

Arg Pro Gln Tyr Ser Leu Ala Glu Leu Leu Ala Gln Cys Asp Pro Asn
    50                  55                  60

Ala Glu Ile Ser Ala Glu Glu Arg Glu Trp Leu Asp Ala Pro Ala Thr
65                  70                  75                  80

Gly Gln Glu Glu Ile
                85

<210> SEQ ID NO 73
<211> LENGTH: 402
<212> TYPE: DNA
<213> ORGANISM: Escherichia coli

<400> SEQUENCE: 73
atgctgaaat atcagctgaa gaacgagaat ggctggatgc accggcgact ggtcaggagg     60
aaatctgaca tggaaagagg ggaaatctgg cttgtctcgc ttgatcctac cgcaggtcat    120
gagcagcagg gaacgcggcc ggtgctgatt gtcacaccgg cggcctttaa tcgcgtgacc    180
cgcctgcctg ttgttgtgcc cgtaaccagc ggaggcaatt ttgcccgcac tgccggcttt    240
gcggtgtcgt tggatggtgt tggcatacgt accacaggtg ttgtacgttg cgatcaaccc    300
cggacaattg atatgaaagc acggggcgga aaacgactcg aacgggttcc ggagactatc    360
atgaacgaag ttcttggccg cctgtccact attctgactt ga                      402

<210> SEQ ID NO 74
<211> LENGTH: 402
<212> TYPE: DNA
<213> ORGANISM: Artificial Sequence
<220> FEATURE:
<223> OTHER INFORMATION: pemK toxin, sequence altered for pemK toxin
      resistance

<400> SEQUENCE: 74
atgctgaaat accagctgaa gaacgagaat ggctggatgc accggcgact ggtcaggagg     60
aaatctgaca tggaaagagg ggaaatctgg cttgtctcgc ttgatcccac cgcaggtcat    120
gagcagcagg gaacgcggcc ggtgctgatt gtcacaccgg cggccttcaa tcgcgtgacc    180
cgcctgcctg ttgttgtgcc cgtgaccagc ggaggcaatt tgcccgcac tgccggcttt     240 gcggtgtcgt tggatggtgt tggcatccgc accacaggtg ttgtgcgttg cgatcaaccc    300
cggacaattg acatgaaagc acggggcgga aaacgactcg aacgggttcc ggagaccatc    360
atgaacgaag ttcttggccg cctgtccact attctgactt ga                      402

<210> SEQ ID NO 75
<211> LENGTH: 133
<212> TYPE: PRT
<213> ORGANISM: Escherichia coli

<400> SEQUENCE: 75

Met Leu Lys Tyr Gln Leu Lys Asn Glu Asn Gly Trp Met His Arg Arg
1               5                   10                  15

Leu Val Arg Arg Lys Ser Asp Met Glu Arg Gly Glu Ile Trp Leu Val
            20                  25                  30

Ser Leu Asp Pro Thr Ala Gly His Glu Gln Gln Gly Thr Arg Pro Val
        35                  40                  45

Leu Ile Val Thr Pro Ala Ala Phe Asn Arg Val Thr Arg Leu Pro Val
    50                  55                  60

Val Val Pro Val Thr Ser Gly Gly Asn Phe Ala Arg Thr Ala Gly Phe
65                  70                  75                  80

Ala Val Ser Leu Asp Gly Val Gly Ile Arg Thr Thr Gly Val Val Arg
                85                  90                  95

Cys Asp Gln Pro Arg Thr Ile Asp Met Lys Ala Arg Gly Gly Lys Arg
            100                 105                 110

Leu Glu Arg Val Pro Glu Thr Ile Met Asn Glu Val Leu Gly Arg Leu
        115                 120                 125

Ser Thr Ile Leu Thr
        130

<210> SEQ ID NO 76
<211> LENGTH: 261
<212> TYPE: DNA
<213> ORGANISM: Escherichia coli

<400> SEQUENCE: 76
atggctgcta acgcgtttgt tcgcgcccga atcgatgaag atctgaagaa tcaggcagcg      60
gacgtactgg ccgggatggg gctgaccatc tctgacctgg ttcgcataac cctcacaaag     120
gtcgcgcgtg aaaaggcatt gccgtttgat ttacgcgagc ctaatcaatt aaccattcaa     180
tcaatcaaaa acagcgaagc tggcattgat gttcataagg ccaaagacgc cgatgattta     240
tttgataaat taggaattta a                                               261

<210> SEQ ID NO 77
<211> LENGTH: 86
<212> TYPE: PRT
<213> ORGANISM: Escherichia coli

<400> SEQUENCE: 77

Met Ala Ala Asn Ala Phe Val Arg Ala Arg Ile Asp Glu Asp Leu Lys
1               5                   10                  15

Asn Gln Ala Ala Asp Val Leu Ala Gly Met Gly Leu Thr Ile Ser Asp
            20                  25                  30

Leu Val Arg Ile Thr Leu Thr Lys Val Ala Arg Glu Lys Ala Leu Pro
        35                  40                  45

Phe Asp Leu Arg Glu Pro Asn Gln Leu Thr Ile Gln Ser Ile Lys Asn
    50                  55                  60

Ser Glu Ala Gly Ile Asp Val His Lys Ala Lys Asp Ala Asp Leu
65                  70                  75                  80

Phe Asp Lys Leu Gly Ile
                85

<210> SEQ ID NO 78
<211> LENGTH: 279
<212> TYPE: DNA
<213> ORGANISM: Escherichia coli

<400> SEQUENCE: 78

```
atgattcaaa gggatattga atactcggga caatattcaa aggatgtaaa acttgcacaa      60
aagcgtcata aggatatgaa taaattgaaa tatcttatga cgcttcttat caataatact     120
ttaccgcttc cagctgttta taaagaccac ccgctgcaag gttcatggaa aggttatcgc     180
gatgctcatg tcgaaccgga ctggatcctg atttacaaac ttaccgataa acttttacga     240
tttgagagaa ctggaactca cgcggcgctc tttgggtaa                            279
```

<210> SEQ ID NO 79
<211> LENGTH: 279
<212> TYPE: DNA
<213> ORGANISM: Artificial Sequence
<220> FEATURE:
<223> OTHER INFORMATION: YafQ toxin, insensitive to YafQ and MazF toxins

<400> SEQUENCE: 79

```
atgattcaaa gggatattga atactcgggc caatattcaa aggatgtaaa acttgctcaa      60
aagcgtcata aggatatgaa taaattgaaa tatcttatga cgcttcttat caataatact     120
ttaccgcttc cagctgttta taaagaccac ccgctgcaag gttcatggaa gggttatcgc     180
gatgctcatg tcgaaccgga ctggatcctg atttataaac ttaccgataa acttttacga     240
tttgagagaa ctggaactca cgcggcgctc tttgggtaa                            279
```

<210> SEQ ID NO 80
<211> LENGTH: 92
<212> TYPE: PRT
<213> ORGANISM: Escherichia coli

<400> SEQUENCE: 80

Met Ile Gln Arg Asp Ile Glu Tyr Ser Gly Gln Tyr Ser Lys Asp Val
1               5                   10                  15

Lys Leu Ala Gln Lys Arg His Lys Asp Met Asn Lys Leu Lys Tyr Leu
            20                  25                  30

Met Thr Leu Leu Ile Asn Asn Thr Leu Pro Leu Pro Ala Val Tyr Lys
        35                  40                  45

Asp His Pro Leu Gln Gly Ser Trp Lys Gly Tyr Arg Asp Ala His Val
    50                  55                  60

Glu Pro Asp Trp Ile Leu Ile Tyr Lys Leu Thr Asp Lys Leu Leu Arg
65                  70                  75                  80

Phe Glu Arg Thr Gly Thr His Ala Ala Leu Phe Gly
                85                  90

REGULATION OF TOXIN AND ANTITOXIN GENES FOR BIOLOGICAL CONTAINMENT

CROSS-REFERENCE TO RELATED APPLICATIONS

This application claims benefit of priority to U.S. Provisional application 61/503,306 filed Jun. 30, 2011 entitled "Regulation of Toxin and Antitoxin Genes for Biological Containment", which is incorporated by reference in its entirety.

REFERENCE TO A SEQUENCE LISTING

This application contains references to amino acid sequences and/or nucleic acid sequences which have been submitted concurrently herewith as the sequence listing text file "60977601_1.txt", file size 76 KiloBytes (KB), created on Jun. 27, 2012. The aforementioned sequence listing is hereby incorporated by reference in its entirety pursuant to 37 C.F.R. §1.52(e)(5).

TECHNICAL FIELD

The present invention relates to the regulation of a toxin and/or antitoxin gene expression in a microorganism, in particular for preventing unintentional or uncontrolled spread of the microorganisms. The present invention also relates to methods of controlling the growth and/or survival of a microorganism, such as a genetically engineered prokaryotic or eukaryotic alga.

BACKGROUND

Genetically modified microorganisms have recently attracted much interest as biofactories for production of foods, bioactive compounds, and biofuels. Spread of the genetically modified microorganisms outside of the intended place of cultivation into natural ecosystems, however, is a major regulatory concern. Some biological containment strategies can result in genetically modified microorganisms self-destructing by expression of heterologous genes encoding lethal proteins. Several bacterial toxins have been considered as good candidates for use in bacterial containment systems, including membrane-destabilizing or pore-forming proteins and enzymes attacking the genetic material of the cell. In many cases, however, mutation of toxin genes introduced into microorganisms results in reduced efficacy of toxin genes over time.

Type II toxin-antitoxin systems are widespread in prokaryotes (Van Melderen and De Bast (2009) *PLoS Genetics* 5: e1000437; Marakova et al (2009) *Biology Direct* 4:19). These toxin genes typically encodes proteins that interfere with transcription (e.g., by inhibiting DNA gyrase) or translation by interfering with ribosome function or by degrading RNA transcripts. Toxins with endoribonucleolytic activity are sometimes referred to as "RNA interferases" and include, for example, the bacterial toxins MazF, pemK, RelE, HicB, HipA, Doc, VapC, yafQ, yhaV, and tasB, among others. Expression of the toxin genes is tightly controlled by antitoxin genes which reside in an operon with the toxin gene. Typically the antitoxin is the first gene of the transcript and overlaps the toxin gene by 1-10 nucleotides, allowing for the antitoxin to be more efficiently translated with respect to the toxin. The antitoxin forms a stable complex with the toxin, resulting in inactivation of the toxin. The antitoxin-toxin complex also binds to the promoter of the TAS, repressing transcription. Thus, under ordinary circumstances, expression of the TAS is shut down—the antitoxin, which is produced in greater abundance, binds to and inactivates the toxin, and prevents further transcription of the toxin operon. The antitoxin protein is labile when not associated with the toxin however, and if the system becomes unbalanced, for example, by increased turnover of the antitoxin, the toxin can persist in the cell free of the antitoxin, where its endoribonucleolytic activity (in cases where the toxin is an "RNA interferase") is able to shut down translation.

The elaborate mechanisms used to limit toxin expression in endogenous systems (see for example Diago Navarro et al. (2009) *FEBS J.* 277: 3097-3117 for a thorough treatment or the parDE TAS regulation) underscore the importance of tightly controlling the expression of an exogenous toxin gene introduced into the cell. The selective pressure to mutate the toxin to an inactive form has limited the potential of toxin genes in biocontainment. Further, in recent years several groups have suggested that native TAS may serve to promote cytostasis rather than cell growth under growth-limiting conditions, and that in many cases at least a portion of a population in which a toxin is activated subsequently recover (see, for example, Cataudella et al. (2012) *Nucl Acids Res*). The ability of cells to survive the expression of an active toxin has also been seen when exogenous genes were expressed in heterologous systems (e.g., Kristofferesen et al (2000) Appl Environ Microbiol 66: 5524-5526), also raising doubts about the practicality of using Type II TASs in biocontainment strategies.

Microorganisms make various metabolic adjustments in response to nutrient depletion, including, for example, transcriptional responses that allow increased uptake of external sources of nutrients as well as scavenging of internal sources. Much of the response to nutrient stress is based on transcriptional regulation of transporters, enzymes, proteins of the translational machinery, etc. Photosynthetic microorganisms that rely on light for chemical energy and carbon fixation, have additional challenges in that the photosynthetic apparatus must be adjusted to prevent excessive light damage to the cell when it may not be possible to maintain photosynthetic electron transport or carbon fixation at optimal levels. The inability to adjust light harvesting and photosystem function can lead to sustained damage to these systems. Not surprisingly, many studies have found that alterations of the photosynthetic apparatus are among the changes seen in transcriptional response to nitrogen (Miller et al (2010) Plant Physiol 154: 1737-1752) phosphate (Yehudai-Resheff et al, (2007) The Plant Cell 19: 1023-1038; Wurch et al (2011) Environ Microbiol 13: 468-481), sulfur (Moseley et al (2009) Genetics 181: 889-905)), iron (Merchant et al. (2006) Biochim Bioophys Acta 1763: 578-594), copper (Castruita et al. (2011) The Plant Cell 23: 1273-1292), and $CO_2$ (Wang et al (2011) Phototsynth Res 109: 115-122) limitation in microalgae and have found that the inability to adjust to nutrient limitation results in death of microalgal cultures (Moseley et al. (2006) Eukaryot. Cell 5: 26-44).

SUMMARY OF THE INVENTION

In some aspects, the invention provides a recombinant prokaryotic or eukaryotic microorganism that includes at least one exogenous nucleic acid molecule encoding a Type II toxin, in which the nucleic acid sequence encoding the Type II toxin is operably linked to a heterologous promoter. The recombinant microorganism can be, for example, a bacterial, archaebacterial, cyanobacterial, fungal, heterokont, or algal species. The recombinant prokaryotic or eukaryotic microorgansim may be a photosynthetic microorganism, such as a cyanobacterium, for example, an *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechocystis, Tolypothrix, Trichodesmium, Tychonema,* or *Xenococcus* species. Alternatively, the microorganism can be a eukaryotic microalga, for example, a species of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachorella, Tetraselmis, Thalassiosira, Viridiella,* or *Volvox.*

The Type II toxin gene may be derived from a eubacterial or archaebacterial species, and optionally can be derived from a cyanobacterial species, for example, any of the aforementioned cyanobacterial species, and can be homologous or heterologous with respect to the recombinant prokaryotic host. The toxin in some additional embodiments can be an endoribonuclease that cleaves specific RNA sequences. In some further embodiments, the nucleotide sequence of the toxin gene can be designed to exclude endonuclease recognition sequences that render the encoded RNA susceptible to cleavage by the toxin.

The exogenous toxin gene can encode, in some alternative embodiments, a toxin of the CcdB toxin family, the RelE toxin family, the MazF toxin family, the ParE toxin family, the PIN toxin family, the Ahal toxin family, the MNT toxin family, the Doc toxin family, the VapC toxin family, the zeta toxin family, the HipA toxin family, or the HigB toxin family. For example, the Type II toxin may be a CcdB, RelE, MazF, ParE, PIN, Ahal, MNT, Doc, VapC, zeta, HipA, HigB, ChpI, StbE, Txe, YafQ, or YoeB toxin, or an ortholog or homolog of any of these toxins, or other Type II toxins.

The heterologous promoter operably linked to the toxin gene in preferred embodiments can be a regulatable promoter, and may be a promoter regulated by a compound that may be present in the cell culture or cell environment, such as, as nonlimiting examples, a sugar, an organic acid, a fatty acid, an amino acid or amino acid analog, a lipid, a hydrocarbon, phosphate, nitrate, ammonium, a metal, a quorum-sensing compound, a lactone, a vitamin, a secreted protein or peptide, or any combination thereof. In some examples, the promoter regulates expression in a prokaryotic microorganism and is selected from the group consisting of a rha promoter, arabinose-inducible promoter (e.g., an L-arabinose-inducible promoter, or an ara or "BAD" promoter), IPTG (isopropyl-β-D-thiogalactopyranoside)-inducible promoter (e.g., a lac, tac, trc, trcE, or trcY promoter), a trp promoter, glnA promoter, cys promoter, secA promoter, psbA promoter, nar promoter, ntc promoter, nir promoter, nr promoter, pho promoter, pst promoter, nrs promoter, tet promoter, metallothionien promoter, ftf promoter, heat shock promoter, cold-inducible promoter, light-inducible promoter, viral promoter, hin promoter, cin promoter, gin promoter, and fimA promoter.

In various examples the toxin gene can be regulated by a promoter induced by nutrient limitation. For example, the promoter regulating the expression of the toxin gene in a prokaryotic microorganism can be a promoter that is responsive to nutrient depletion, such as, for example, a promoter upregulated by nitrogen starvation such as, for example, a nr, nar (nitrate reductase), nir (nitrite reductase), ntc, ntr, or gln promoter; or a promoter upregulated by phosphate starvation, such as, for example, a pho or pst promoter. Additionally, the engineered microorganism can further include a gene encoding a cognate antitoxin where the antitoxin gene is regulated by a promoter that is not induced by the nutrient limitation regulating the toxin. In examples where the engineered microorganism is a eukaryotic microorganism, the promoter operably linked to an exogenous toxin gene can be a promoter that is functional in a eukaryotic cell, and can be, for example, a promoter that is responsive to nutrient depletion, for example, nitrate, phosphate, sulfur, copper, iron, or $CO_2$ depletion. In some examples the toxin promoter comprises at least a portion of SEQ ID NO:56, SEQ ID NO:57, SEQ ID NO:58, SEQ ID NO:59, SEQ ID NO:60, or SEQ ID NO:65. In various examples where the toxin gene is regulated by a promoter induced by nutrient limitation, the engineered microorganism further includes a gene encoding a cognate antitoxin where the antitoxin gene is regulated by a promoter that is not induced by the nutrient limitation regulating the toxin. For example, the antitoxin gene may be regulated by at least a portion of SEQ ID NO:62, SEQ ID NO:63, or SEQ ID NO:64.

Alternatively, the promoter regulating a toxin gene transformed into a host microorganism can be a synthetic promoter, for example, a promoter that includes a sequence that can be recognized and bound by a transcription factor, which can be, for example, an engineered transcription factor, where the sequence is positioned upstream of a minimal promoter that is operable in the host microorganism.

The invention also includes microorganisms engineered for biocontainment that include one or more exogenous nucleic acid molecules or sequences encoding two or more Type II toxins, for example, the engineered microorganism can include two or more exogenous genes where the two or more genes encode different Type II toxins. Two or more toxin-encoding nucleic acid sequences can be on the same or different nucleic acid molecules. The two or more toxin genes may be independently operably linked to copies of the same heterologous promoter or may be operably linked to different heterologous promoters. Optionally, in embodiments where the recombinant microorganism includes two or more different exogenous toxin genes, one or both of the exogenous toxin genes can be sequence-optimized to be resistant to an RNA endonuclease activity of one, two, or more than two of the toxins encoded by the two or more different exogenous toxin genes.

In some examples where the recombinant microorganism is a prokaryotic microorganism, the prokaryotic microorganism that includes an exogenous nucleic acid molecule encoding a Type II toxin can further include an endogenous gene encoding an antitoxin that inactivates the Type II toxin encoded by the exogenous gene, i.e., an antitoxin "cognate to" the toxin encoded by the exogenous gene. In alternate embodiments, a recombinant prokaryotic microorganism that includes an exogenous toxin gene may not include an endogenous antitoxin gene cognate to the toxin gene. Alternatively or in addition to any of these embodiments, the recombinant prokaryotic microorgansim that includes an exogenous nucleic acid molecule encoding a Type II toxin can further include an exogenous nucleic acid molecule encoding a cognate antitoxin. In embodiments in which the recombinant cyanobacterium includes an exogenous nucleic acid sequence encoding an antitoxin, the antitoxin-encoding sequence can be, in alternate embodiments, on the same exogenous nucleic acid molecule that encodes the Type II toxin, or can be on a different exogenous nucleic acid molecule. In any of these embodiments, the prokaryotic microorganism can be a photosynthetic microorganism, and can be, for example a cyanobacterium. In any of these embodiments, the heterologous promoter regulating the toxin gene can be a promoter regulated by the scarcity of a nutrient, e.g., by depletion of nitrogen, phosphorus, sulfur, $CO_2$, iron, copper, etc. from the growth medium of environment.

A prokaryotic host that includes two or more exogenous genes encoding toxins can optionally further include one, two, or more endogenous antitoxin genes cognate to one, two, or more of the toxins. Alternatively or in addition, a prokaryotic host that includes two or more exogenous genes encoding toxins can optionally further include at least one exogenous antitoxin gene cognate to one, two, or more of the toxins.

The present invention also relates to a method of controlling the growth and/or survival of a microorganism, such as a cyanobacterium, the method comprising steps of introducing an exogenous nucleic acid molecule encoding a Type II toxin into a prokaryotic microorganism, in which the exogenous toxin gene is operably linked to a heterologous promoter, in which expression of the toxin gene induces cell death or impairs the growth or viability of the microorganism. Optionally but preferably, the heterologous promoter operably linked to the Type II toxin gene can be regulated by the presence or absence of a nutrient or compound that may be present in the cell culture or cell environment, or by an environmental condition, such as, for example, salinity, pH, temperature, or light intensity. Expression of the Type II toxin gene regulated by a heterologous promoter inhibits the growth or impairs the viability of the cells. In some preferred embodiments, the microorganism can be a photosynthetic microorganism, and expression of the toxin gene regulated by a heterologous promoter can induce chlorosis and/or impair photosynthesis.

In some examples, the microorganism can include an endogenous gene encoding an antitoxin cognate to the toxin encoded by the exogenous nucleic acid molecule. The exogenous antitoxin gene can be operably linked to a heterologous promoter, preferably a regulatable promoter, such as, for example, an inducible promoter or a repressible promoter. The heterologous promoter operably linked to the exogenous antitoxin gene can activate transcription during permissive growth conditions, for example, during contained growth and/or production conditions. Additionally, in these embodiments, the endogenous antitoxin gene of the endogenous TAS of the host microorganism can be inactivated and/or attenuated. For example, in some illustrative examples the host microorganism includes a pemI/pemK TAS, in which the host microorganism is engineered to include an exogenous gene encoding the pemI antitoxin operably linked to a regulatable heterologous promoter, and the endogenous PemI gene is inactivated, for example by homologous recombination. In further illustrative examples the host microorganism includes an axe/txe TAS, in which the host microorganism is engineered to include an exogenous gene encoding the axe antitoxin operably linked to a regulatable heterologous promoter, and the endogenous axe gene is inactivated, for example by homologous recombination. In yet further illustrative examples the host microorganism includes a phd/doc TAS, in which the host microorganism is engineered to include an exogenous gene encoding the phd antitoxin operably linked to a regulatable heterologous promoter, and the endogenous phd gene is inactivated, for example by homologous recombination. Further examples can include, as nonlimiting examples, mazE/mazF TAS, a hicB/hicA TAS, a vapB/vapC TAS, or any other TAS, in which the antitoxin gene (e.g., mazE, hicB, vapB, or other antitoxin gene) is introduced into the cell in operable linkage with a heterologous promoter, and the endogenous antitoxin gene (e.g., mazE, pemI, hicB, vapB, dinJ, or other antitoxin gene) is knocked out or otherwise inactivated, for example by homologous recombination that introduces an insertion or inactivating mutation. In some embodiments, the exogenous antitoxin gene described herein can include, but is not limited to, an antitoxin gene encoding an antitoxin of the CcdA antitoxin family, RelB antitoxin family, MazE antitoxin family, ParD antitoxin family, PIN antitoxin family, MNT antitoxin family, Phd antitoxin family, VapB antitoxin family, zeta antitoxin family, and/or HipB antitoxin family. Additionally or alternately, the antitoxin gene can be selected from the group consisting of cyanobacterial homologs of axe, phd, mazE, hicB, vapB, pemI, relB, parD, kiS, ccdA, yafN, stbD, yoeM, dinJ, PIN, and combinations thereof. The exogenous antitoxin gene can be homologous or heterologous with respect to the host microorganism.

In further embodiments, a recombinant host prokaryotic microorganism can include two or more endogenous TASs, and can include two or more exogenous antitoxin genes operably linked to heterologous promoters, in which the host microorganism contains inactivated endogenous antitoxin genes corresponding to the introduced antitoxin genes that can be regulated by induction, repression, or derepression of operably linked heterologous promoters. The heterologous promoters operably linked to two different antitoxin genes can be different copies of the same promoter, or can be different promoters. In some embodiments, for example, two or more different promoters operably linked to two or more antitoxin genes can be regulated by different compounds of environmental conditions.

In some preferred embodiments, the heterologous promoter that regulates expression of the exogenous antitoxin gene is active in the presence of a compound that can be provided in the growth media that is not typically present in the external environment in sufficient quantity to activate the promoter, or is repressed or inactive under certain environmental conditions that may occur when the organism has escaped from controlled conditions (for example, a range or threshold of nutrient availability or concentration, light intensity, salinity, pH, or temperature).

The present invention also relates to a method of controlling the growth and/or survival of a prokaryotic microorganism, such as a cyanobacterium, the method comprising steps of introducing an exogenous nucleic acid molecule encoding an antitoxin into a prokaryotic host microorganism, in which the exogenous antitoxin gene is operably linked to a heterologous promoter, and the prokaryotic host microorganism includes an endogenous TAS that includes a gene encoding a toxin that is cognate to the antitoxin encoded by the introduced gene. The method further includes inactivating the antitoxin gene of the endogenous TAS. The exogenous antitoxin gene is regulatably expressed under conditions in which growth the host microorganism is desired, for example, by means of a nutrient or regulator molecule included in the growth medium, or by an environmental conditions, such as, for example, salinity, pH, temperature, or light intensity. Preferably, when the host microorganism is outside the containment growth area, the nutrient or regulator molecule is no longer available or the environmental conditions are altered, such that the exogenous antitoxin gene regulated by a heterologous promoter is no longer expressed and the growth or viability of the cells is impaired. In some embodiments, the prokaryotic host can be a cyanobacterium, and reduced expression of the antitoxin gene regulated by a heterologous promoter can impair photosynthesis and/or can result in chlorosis.

In a further aspect, provided herein is a prokaryotic microorganism that comprises an endogenous TAS, in which a heterologous promoter has been inserted upstream of the antitoxin-toxin operon of the TAS. For example, the heterologous promoter can replace the endogenous promoter of the antitoxin-toxin operon. Without limiting the invention to any particular mechanism, replacing the endogenous promoter of the antitoxin-toxin operon can alter the regulation of transcription of the antitoxin-toxin operon from being repressible by an antitoxin-toxin protein complex to being regulated by factors that regulate the heterologous promoter. For example, a compound present in the growth media or external environment, temperature, light intensity, etc. Induction (or derepression) of transcription from the heterologous promoter can thereby result in transcription and translation of a stable toxin that can lead to impaired growth or viability of the host cell.

Further included in the invention are prokaryotic microorganisms such as cyanobacteria that include two or more endogenous TASs, in which a heterologous promoter has been inserted upstream of the antitoxin-toxin operon of at least two of the two or more endogenous TASs. The heterologous promoters operably linked to two different antitoxin-toxin operons can be different copies of the same promoter, or can be different promoters. In some embodiments, for example, two or more different promoters operably linked to two or more TAS operons can be regulated by different compounds and/or environmental conditions.

The present invention also relates to a method of controlling the growth and/or survival of a prokaryotic microorganism, such as a cyanobacterium, the method comprising steps of introducing a heterologous regulatable promoter upstream of an endogenous TAS operon. In these embodiments, expression of the TAS operon can induce cell death or can impair the growth and/or viability of the microbial host. Optionally but preferably, the heterologous promoter can be regulated by a the availability of a nutrient or compound that may be present in the cell culture or cell environment, or by an environmental conditions, such as, for example, salinity, pH, temperature, or light intensity. Preferably, expression of the antitoxin-toxin operon regulated by a heterologous promoter can inhibit the growth or impair the viability of the prokaryotic host cells. In some preferred embodiments, the prokaryotic host microorganism can be a cyanobacterium, and expression of the antitoxin-toxin operon regulated by a heterologous promoter can impair photosynthesis.

In additional aspects, the invention further provides a recombinant prokaryotic microorganism comprising an antitoxin antisense construct, in which the antitoxin gene antisense construct comprises an antisense nucleotide sequence that hybridizes with at least a portion of at least one antitoxin gene of a TAS endogenous to the recombinant prokaryotic microorganism, in which the antisense nucleotide sequence is operably linked to a heterologous promoter. In some preferred embodiments, the antisense construct can be integrated into the genome of the recombinant prokaryotic organism. The prokaryotic microorganism in some embodiments can be a cyanobacterium.

In some embodiments, the antitoxin gene described herein includes, but is not limited to, an antitoxin of CcdA antitoxin family, RelB antitoxin family, MazE antitoxin family, ParD antitoxin family, PIN antitoxin family, MNT antitoxin family, Phd antitoxin family, VapB antitoxin family, zeta antitoxin family, or HipB antitoxin family. Additionally or alternately, the antitoxin gene can be selected from the group consisting of cyanobacterial homologs of axe, phd, mazE, hicB, vapB, pemI, relB, parD, kiS, ccdA, yafN, stbD, yoeM, dinJ, PIN, and combinations thereof.

In further embodiments, the invention can include prokaryotic microorganisms such as cyanobacteria that can include two or more antitoxin antisense constructs including regulatable promoters. The regulatable promoters operably linked to two or more of the different antitoxin antisense sequences can be different copies of the same promoter, or can be different promoters. In some embodiments, for example, two or more different promoters operably linked to two or more antitoxin antisense sequences can be regulated by different compounds and/or environmental conditions.

In an additional aspect, the present invention further provides a vector comprising a promoter sequence operably linked to a nucleic acid sequence encoding an antisense oligonucleotide that hybridizes with at least a portion of an endogenous antitoxin gene of a toxin-antitoxin system in a prokaryotic microorganism. The promoter is preferably an inducible promoter.

The present invention further relates to a method of controlling the growth and/or survival of a prokaryotic microorganism that comprises an endogenous TAS by introducing an exogenous antisense construct into the prokaryotic microorganism, in which expression of the antitoxin antisense construct is regulated by one or more compounds or environmental conditions, such that the prokaryotic microorganism has reduced viability or impaired growth when the culture or environmental conditions promote expression of the antitoxin gene antisense construct. The prokaryotic microorganism in these embodiments includes an endogenous antitoxin gene complementary to at least a portion of the antisense sequence of the antisense construct. Optionally but preferably, the heterologous promoter is regulated by a compound that may be present in the cell culture or cell environment, or by an environmental conditions, such as, for example, salinity, pH, temperature, or light intensity. Preferably, expression of the antisense sequence is regulated by a heterologous promoter that inhibits the growth or impairs the viability of the cells. In some preferred embodiments, the prokaryotic host can be a cyanobacterium, and expression of the antisense construct regulated by a heterologous promoter can impair photosynthesis.

In further aspects, the present invention provides a prokaryotic microorganism comprising an endogenous toxin-antitoxin system (TAS), in which at least one heterologous regulatory element is operably linked to the toxin gene of the endogenous TAS. The endogenous toxin-antitoxin system may be a Type II toxin-antitoxin system, in which at least one heterologous regulatory element is operably linked to the toxin gene of the endogenous Type II TAS operon.

In particular embodiments, the heterologous regulatory element can be inserted into the genome of the prokaryotic microorganism upstream of the toxin gene. Further, the heterologous regulatory element may comprise a promoter that directs expression of the toxin gene. Additionally, the heterologous regulatory element may also in some embodiments include a transcriptional terminator upstream of the promoter. In particular embodiments, insertion of a heterologous regulatory element can be by homologous recombination into the host genome. The heterologous regulatory element may be inserted, for example, by homologous recombination of a nucleic acid construct that can include, in certain exemplary embodiments, a portion of at least the 3' end of the antitoxin gene of an endogenous antitoxin-toxin operon, one or more gene regulatory elements, and a portion of at least a portion of the 5' end of the toxin gene of the endogenous antitoxin-toxin operon.

The promoter introduced into the endogenous TAS operon may be a promoter that is regulated by a compound that may be present or provided in the cell culture or cell environment, such as, as nonlimiting examples, a sugar, an organic acid, a fatty acid, a lipid, a hydrocarbon, phosphate, nitrate, ammonium, sulfur, a metal (e.g., copper, iron, nickel, cadmium), a quorum-sensing compound, a flavonoid, a lactone, a phenolic, a secreted protein or peptide, or any combination thereof. In some examples, the promoter is selected from the group consisting of a rha promoter, arabinose-inducible promoter (e.g., an L-arabinose-inducible promoter, or an ara or "BAD" promoter), IPTG (isopropyl-β-D-thiogalactopyranoside)-inducible promoter (e.g., a lac, tac, trc, trcE, or trcY promoter), trp promoter, glnA promoter, cys promoter, secA promoter, psbA promoter, nar promoter, ntc promoter, nir promoter, nr promoter, pho promoter, pst promoter, nrs promoter, tet promoter, metallothionien promoter, ftf promoter, heat shock promoter, cold-inducible promoter, viral promoter, hin promoter, cin promoter, gin promoter, and fimA promoter. In some examples, the promoter is induced when a compound is depleted from the growth media or environment, for example the promoter may be induced by nitrogen, phosphorus, sulfur, iron, copper, or $CO_2$ limitation.

Additionally, the engineered TAS operon of the prokaryotic microorganism may comprise a second promoter, in which the second promoter is positioned upstream of the first inserted promoter that directs expression of the toxin gene and is positioned downstream of the antitoxin gene. The second and first promoters in these embodiments direct transcription in opposite directions. The second promoter can direct expression of a nucleic acid sequence encoding an antisense oligonucleotide that hybridizes with at least a portion of the antitoxin gene of the endogenous toxin-antitoxin system, where the first promoter can direct expression of the toxin gene of the antitoxin-toxin operon. In some embodiments, the second promoter downstream of the antitoxin gene is optionally regulated by the same compound as the promoter that directs expression of the toxin gene. Additionally or alternately, a bidirectional promoter can be positioned 3' of the antitoxin gene and 5' of the toxin gene in an endogenous antitoxin-toxin operon, where the bidirectional promoter can direct expression of the toxin gene and expression of a nucleic acid sequence encoding an antisense oligonucleotide that hybridizes with at least a portion of the antitoxin gene.

Additionally, in some embodiments, the prokaryotic microorganism can comprise two or more endogenous toxin-antitoxin systems, and at least two of the toxin-antitoxin systems can include a heterologous promoter operably linked to toxin genes of the two or more toxin-antitoxin operons. The at least two toxin-antitoxin systems can comprise the same heterologous promoter or different heterologous promoters operably linked to the toxin genes of the toxin-antitoxin operons.

The present invention relates in some aspects to a method of controlling the growth and/or survival of a prokaryotic microorganism that comprises an endogenous Type II TAS, in which at least one heterologous regulatory element is operably linked to the toxin gene of the endogenous TAS. In particular embodiments, the heterologous regulatory element can be inserted into the genome of the prokaryotic microorganism upstream of the toxin gene. Further, the heterologous regulatory element may comprise a promoter that directs expression of the toxin gene. Additionally, the heterologous regulatory element may also in some embodiments include a transcriptional terminator upstream of the promoter. In particular embodiments, insertion of a heterologous regulatory element can be by homologous recombination into the host genome, as disclosed herein. The methods can comprise a step of introducing at least one heterologous regulatory element into the genome of a prokaryotic microorganism, such that at least one heterologous regulatory element is operably linked to a toxin gene of a TAS operon of the prokaryotic microorganism. In these embodiments, expression of the antitoxin antisense construct can be regulated by one or more compounds or environmental conditions, such that the prokaryotic microorganism has reduced viability or impaired growth when the culture or environmental conditions promote expression of the toxin gene regulated by the heterologous regulatory element. Optionally but preferably, the heterologous regulatory element, which can be or include a promoter, is regulated by a compound that may be present in the cell culture or cell environment, or by an environmental conditions, such as, for example, salinity, pH, temperature, or light intensity. Preferably, expression of the toxin gene inhibits the growth or impairs the viability of the cells. In some preferred embodiments, the prokaryotic host is a cyanobacterium, and expression of the toxin gene regulated by a heterologous promoter can impair photosynthesis.

In some embodiments, the prokaryotic microorganism described in any of the embodiments can be a photosynthetic microorganism. Further, the prokaryotic microorganism may be a cyanobacterial species. In further embodiments, the prokaryotic microorganism described herein is an *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechocystis, Tolypothrix, Trichodesmium, Tychonema,* or *Xenococcus* species.

In additional embodiments, the endogenous toxin-antitoxin system described in any of the embodiments can include, but is not limited to, a TAS of the ccdB toxin family, RelE toxin family, MazF toxin family, ParE toxin family, PIN toxin family, Ahal toxin family, MNT toxin family, Doc toxin family, VapC toxin family, zeta toxin family, HipA toxin family, or HigB toxin family. Additionally or alternately, the toxin gene of the antitoxin-toxin operon can be any of txe, doc, mazF, hicA, vapC, pemK, ccdB, relE, parE, PIN, kiD, yafQ, rv3182, stbE, yoeB, and Z5902 and/or the antitoxin gene of the antitoxin-toxin operon can be any homologs (e.g., orthologs or paralogs) of axe, phd, mazE, hicB, vapB, pemI, relB, parD, kiS, ccdA, yafN, stbD, yoeM, dinJ, and PIN.

The present invention also related to a method of introducing a toxin gene into a microorganism, comprising transforming a vector comprising a toxin gene and a cognate antitoxin gene into the microorganism, in which the toxin is in an integrating portion of the vector, and the antitoxin gene is in a non-integrating portion of the vector. Additionally or alternately, the toxin gene is under control of a regulatable promoter and/or the antitoxin gene is under control of a promoter that is active under culture conditions, for example, under nutrient replete conditions. The antitoxin gene promoter may be, in various examples, repressed when one or more nutrients is limiting or when a compound present in the culture medium is withdrawn. Alternatively, the antitoxin gene promoter may be a constitiutive promoter, for example, a promoter that is not downregulated in response to nutrient depletion or the absence of a compound.

Also provided herein are microorganisms, such as but not limited to eukaryotic or prokaryotic photosynthetic microorganisms that include an exogenous Type II toxin gene and further include an exogenous Type II antitoxin gene. In some examples, the nucleic acid sequence encoding the Type II toxin is operably linked to a promoter activated by depletion of a nutrient from the growth media or environment of the microorganism. Additionally, the microorganism can include a gene encoding an antitoxin cognate to the toxin, where the antitoxin gene is operably linked to a promoter that is not induced by limitation of one or more of nitrogen, phosphate, sulfur, iron, copper, or CO2. In some examples, expression of the Type II toxin gene under conditions of nutrient limitation results in the inability of a photosynthetic microorganism to adjust to nutrient limitation. In some examples, a photosynthetic microorganism that expresses a Type II toxin under nutrient limitation can incur photosynthetic impairment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 is an alignment of the native *E. coli* MazF gene (SEQ. ID No:68) and a sequence-altered version of the MazF gene that excludes the ACA MazF ribonuclease recognition site ("MazE insens, "SEQ ID No:69). Endoribonuclease sites in the native *E. coli* gene are underlined, and the mutated nucleotide is in bold.

FIG. 8 is an alignment of the native *E. coli* pemK gene (SEQ ID No:73) and a sequence-altered version of the pemK gene that excludes the TA(A/C/T) pemK ribonuclease recognition site ("pemK−insens,"SEQ ID No:74). Endoribonuclease sites in the native *E. coli* gene are underlined, and the mutated nucleotide is in bold.

FIG. 9 is an alignment of the native *E. coli* YafQ gene (SEQ ID NO:78) and a sequence-altered version of the YafQ gene that excludes the AAA codon followed by A or G, as well as the ACA MazF ribonuclease recognition site ("MazE, YafQ-insens, "SEQ ID NO:79). Endoribonculease sites in the native *E. coli* gene are underlined, and the mutated nucleotide is in bold.

DETAILED DESCRIPTION

Figure 1:
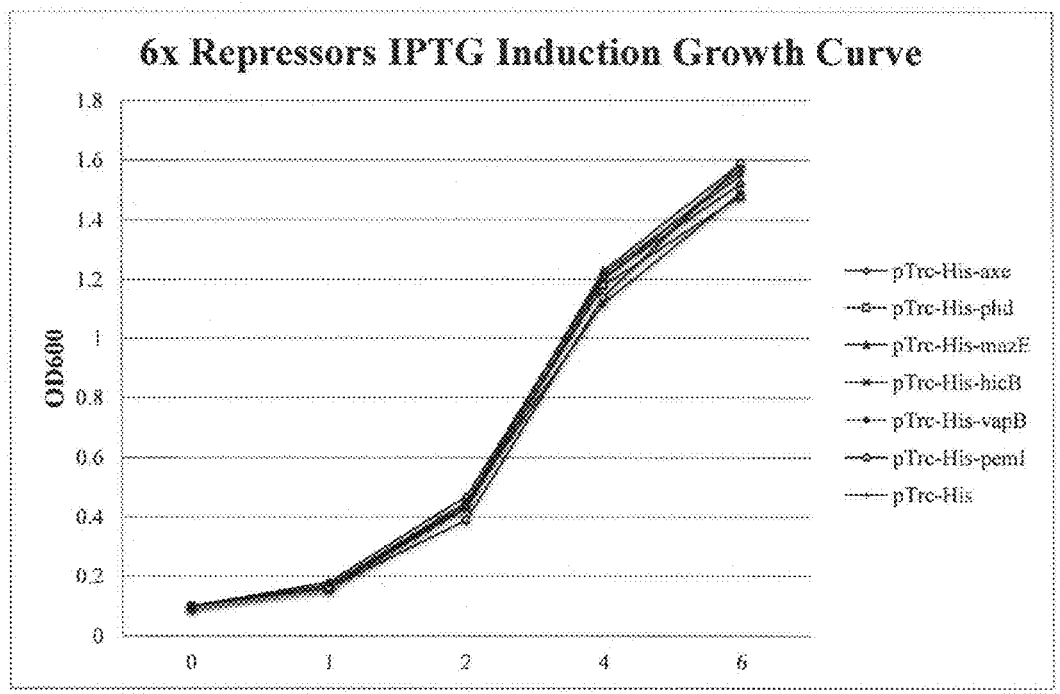
FIG. 1 depicts the time course of *E. coli* culture growth after induction of gene expression of different antitoxin genes with isopropyl-β-D-thio-galactoside (IPTG).

The present invention provides microorganisms, nucleic acid constructs, and methods for biological containment of recombinant microorganisms, such as but not limited to eukaryotic microalgae and cyanobacteria, through expression of Type II toxin genes and/or through inhibition of expression of exogenous or endogenous antitoxin genes. In particular examples, a Type II toxin gene introduced into a microorganism for biocontainment can encode a ribonuclease, and the toxin gene can have a sequence that has been altered with respect to the native Type II toxin gene to eliminate one or more sequences that are recognized (as transcribed into RNA sequences) by the Type II toxin itself. The invention further provides embodiments for biocontainment that can use multiple Type II toxin genes, where the engineered microorganism optionally but preferably also include the cognate antitoxin genes. Also provided are strategies for utilizing endogenous TASs for biocontainment, for example, by altering the expression of the toxin gene and/or the antitoxin gene of an endogenous RAS. It is also within the scope of the invention to use various embodiments of the aspects of the invention in any combination.

Toxin-Antitoxin Systems (TASs)

The toxin component of toxin-antitoxin system (TAS) can include a protein that typically causes cytostasis and/or cell death if expressed above a certain level, whereas the (cognate) antitoxin component can regulate the expression of the toxin, can inactivate the toxin, and/or can counteract the cytostatic/toxic effect of the toxin, thereby preventing cell death. TASs can be classified into two major types on the basis of the nature of the antitoxin. Type I TASs can encompass an antisense RNA antitoxin complementary to the toxin mRNA and that can prevent its translation. On the other hand, Type II TASs employ a protein antitoxin to keep the toxin inactivated, e.g., via a protein-protein interaction. Type II TASs are generally encoded by genes organized in operons, in which a single promoter is typically found upstream of an antitoxin gene, which is followed by a toxin gene that can commonly overlap the antitoxin gene, such that the 5' end of the toxin gene is typically found within ten nucleotides upstream of the 3' end of the antitoxin gene.

The toxin of a Type II TAS may employ various mechanisms in killing the cells. In one aspect, the toxins of Type II TASs considered herein can function as RNAses (also called "RNA interferases") that can act as RNA-based endonucleases, including, but not limited to, colicin E3, VapC, Doc, HigB, RelE, and MazF toxins, as well as combinations thereof. Additionally or alternately, the toxins can function as inhibitors of DNA gyrase that can abrogate cell reproduction, e.g., by blocking DNA replication, including, but not limited to, the CcdB toxin. Further additionally or alternately, the toxins can function as protein kinases that can abrogate reproduction of the microorganism and/or can render the microorganism dormant, e.g., by inhibiting translation through phosphorylation of the elongation factor EF-Tu. Such protein kinases can include, but are not limited to, HipA toxin.

The antitoxin of Type II TAS can be a dual-function, two-domain protein that comprises, consists essentially of, or consists of at least one protein-protein interaction domain and at least one DNA-binding domain. When not complexed with other proteins, antitoxins may have largely disordered structures and can be highly susceptible to proteolysis, and can hence be relatively unstable. Upon interaction with the respective toxin(s) via their protein-protein interaction domain(s), the antitoxin(s) can assume compact structure(s) and can accordingly be stabilized. In many embodiments, the antitoxin binding can inhibit the activity of the cognate toxin, and/or the stable toxin-antitoxin (TA) complex can bind to the operator of the corresponding TAS operon, e.g., via the DNA-binding domain of the antitoxin to (auto)repress its transcription. Thus, in some embodiments, the antitoxin in type II TAS may exert control over the activity of the TAS on at least two levels, by directly inhibiting the toxin and by repressing the expression of both TAS components.

The toxin gene can be a gene encoding any toxin protein, e.g., that can have a lethal activity as described herein and that interacts with a cognate antitoxin such that its lethal activity can be inhibited and/or prevented. For example, the toxin gene of the TAS can encode a polypeptide having lethal activity that is a member of HicA toxin family, PemK toxin family, CcdB toxin family, RelE toxin family, MazF toxin family, ParE toxin family, PIN toxin family, Ahal toxin family, MNT toxin family, Doc toxin family, VapC toxin family, zeta toxin family, HipA toxin family, and HigB toxin family. In further embodiments, the toxin gene can be a homolog (e.g., an ortholog) of txe, doc, mazF, hicA, vapC, pemK, ccdB, relE, parE, PIN, kiD, yafQ, rv3182, stbE, yoeB, and/or Z5902.

Examples of the toxin genes that can be used in the methods and microorganisms herein can include, without limitation, toxin genes of *E. coli*, genes encoding *Cyanothece* sp. Txe protein (Genbank protein accession numbers ADN15973.1; YP_003139280.1; YP_003889248.1; ACV02445.1; YP_003139223.1; YP_003136478.1; YP_002372701.1; YP_002372643.1; ACV02388.1; ACU99642.1; ACK66545.1; ACK66487.1), *Arthrospira maxima* Txe protein (Genbank protein accession numbers ZP_03274874.1; EDZ93600.1), *Microcystis aeruginosa* Txe protein (Genbank protein accession numbers CA088400.1; CA091243.1), *Synechococcus elongatus* MazF protein (Genbank protein accession number YP_173189.1), *Cyanothece* sp. MazF protein (Genbank protein accession numbers ADN14780.1; ADN14211.1; ADN12516.1; ADN12516.1; YP_002381166.1; YP_002484833.1; YP_002484117.1; YP_002483246.1; YP_002373821.1; YP_002373765.1; YP_002373335.1; YP_002364823.1; YP_002364811.1; YP_003888055.1; YP_003887486.1), *Microcystis aeruginosa* HicA protein (Genbank protein accession numbers BAG03061.1; YP_001658253.1), *Cyanothece* sp. HicA protein (Genbank protein accession numbers YP_001806450.1; ACB54384.1; YP_001803995.1; ACB51929.1; ZP_01732465.1; ZP_01729969.1; ZP_01729199.1; ZP_01727862.1; EAZ92576.1), *Nostoc* sp. HicA protein (Genbank protein accession numbers YP_001806450.1; BAB76976.1; NP_489317.1), *Oscillatoria* sp. HicA protein (Genbank protein accession numbers CBN54076.1; ZP_07108930.1), *Acaryochloris marina* HicA protein (Genbank protein accession numbers YP_001517092.1; ABW27776.1), *Crocosphaera watsonii* HicA protein (Genbank protein accession numbers ZP_00515166.1), *Arthrospira platensis* HicA protein (Genbank protein accession number BAI89981.1), *Arthrospira platensis* str. HicA protein (Genbank protein accession number ZP_06382218.1), *Synechocystis* sp. VapC protein (Genbank protein accession numbers BAA17012.1; BAA10330.1; NP_442260.1; NP_440332.1; ZP_07974844.1), *Synechocystis* sp. RelE protein (Genbank protein accession numbers ZP_01085890.1; EAQ74219.1), *Nostoc punctiforme* RelE protein (Genbank protein accession numbers ACC80417.1; ACC83798.1; YP_001865360.1; YP_001868741.1), *Cyanothece* sp. RelE protein (Genbank protein accession numbers YP_002370903.1; YP_002377124.1; YP_003886168.1; YP_003890925.1; ADN18560.1; ACK70256.1; ACK64747.1; ADN12780.1; YP_003900060.1; YP_003900263.1; YP_003900263.1), *Synechocystis* sp. PIN protein (Genbank protein accession numbers ACA99984.1; ACA98072.1; ACB00865.1; ACB00290.1; ZP_01079375.1; ACB01033.1; ACB00960.1; EAQ70500.1), *Nostoc punctiforme* PemK protein (Genbank protein accession number ACC80280.1), *Cyanothece* sp. PemK protein (Genbank protein accession numbers ADN14780.1; ADN14211.1; YP_003136988.1; YP_002381166.1; YP_002484833.1; YP_002484117.1; YP_002483246.1; YP_002373821.1; YP_002373335.1; YP_002364823.1; YP_003888055.1; YP_003887486.1; ACK69644.1; ACV00153.1; ACL46472.1; ACL45756.1; ACL44885.1), and combinations thereof. The foregoing list is exemplary and not limiting. Other examples can include homologs of these toxins, such as their orthologs in other species or strains, as well variants of these toxins, such as variants having at least 60%, for example at least 65%, at least 70%, at least 75%, at least 80%, at least 85%, at least 90%, at least 95%, at least 96%, at least 97%, at least 98%, or at least 99% amino acid sequence identity to an identified Type II toxin and/or to a cognate of an identified antitoxin.

The antitoxin gene can be a gene encoding any antitoxin protein, e.g., that can interact with a toxin gene and can have an antidote activity as described herein, i.e., the antitoxin gene/protein can inhibit, diminish, and/or neutralize the expression and/or the otherwise lethal activity of the cognate toxin gene/protein, e.g., by binding to the toxin protein. For example, an antitoxin gene used in the methods and microorganisms provided herein can encode a polypeptide having antidote activity that is a member of the HicB antitoxin family, PemI antitoxin family, CcdA antitoxin family, RelB antitoxin family, MazE antitoxin family, ParD antitoxin family, RHH antitoxin family, ArsR antitoxin family, HEPN antitoxin family, Phd antitoxin family, VapB antitoxin family, epsilon antitoxin family, HipB antitoxin family, HigA antitoxin family, HTH antitoxin family, MJ1172-like antitoxin family, StbD/axe antitoxin family, and combinations thereof. In further embodiments, the antitoxin gene can be a homolog of axe, phd, mazE, hicB, vapB, pemI, relB, parD, kiS, ccdA, yafN, stbD, yoeM, dinJ, or PIN.

Examples of the antitoxin genes as described herein can include, without limitation, genes encoding antitoxins of *E. coli, Cyanobium* sp. Axe protein (Genbank protein accession numbers ZP_05045974.1; EDY39283.1), *Acaryochloris marina* Axe protein (Genbank protein accession numbers YP_001516924.1; YP_001515235.1; ABW27750.1; ABW27610.1; ABW25921.1; YP_001522298.1; ABW32984.1), *Synechocystis* sp. Phd protein (Genbank protein accession numbers YP_001734097.1; ACA98841.1; ZP_01085949.1; ZP_01470857.1; EAU74652.1; EAQ74278.1; ZP_07974939.1; ZP_07974866.1; ZP_07974840.1; ZP_07974105.1; ZP_07970842.1; ZP_01086419.1; ZP_01086044.1; ZP_01085889.1; ZP_01085677.1; ZP_01085189.1), *Cyanobium* sp. MazE protein (Genbank protein accession numbers ADN14210.1; YP_002482420.1; YP_002373117.1; YP_003887485.1; ACK69643.1; ACK69029.1; ACV01977.1; ACL45755.1; ACL44059.1), *Cyanobium* sp. StbD protein (Genbank protein accession numbers ZP_01730833.1; EAZ89789.1), and combinations thereof. The foregoing list is exemplary and not limiting. Other examples include orthologs of these antitoxins, as well variants of these antitoxins and their orthologs in other species, such as variants having at least 55%, for example at least 60%, at least 65%, at least 70%, at least 75%, at least 80%, at least 85%, at least 90%, at least 95%, at least 96%, at least 97%, at least 98%, or at least 99% amino acid sequence identity to an identified antitoxin and/or to a cognate of an identified Type II toxin.

As discussed above, the antitoxins of the present invention may advantageously interact with the toxins disclosed herein. Toxins and antitoxins that interact with one another such that the toxin can have its activity significantly reduced (e.g., inactivated) by the antitoxin are referred to herein as cognate toxins or antitoxins. Members of certain toxin families may interact with members of certain antitoxin families. For example, an antitoxin of a CcdA antitoxin family, RelB antitoxin family, MazE antitoxin family, ParD antitoxin family, RHH antitoxin family, ArsR antitoxin family, HEPN antitoxin family, Phd antitoxin family, VapB antitoxin family, epsilon antitoxin family, HipB antitoxin family, and/or HigA antitoxin family can interact with a toxin of a CcdB toxin family, RelE toxin family, MazF toxin family, ParE toxin family, PIN toxin family, AhaI toxin family, MNT toxin family, Doc toxin family, VapC toxin family, zeta toxin family, HipA toxin family, and/or HigB toxin family, respectively. Further, an antitoxin of the present invention may interact with toxins of more than one toxin family, and a toxin of the present invention may interact with antitoxins of various antitoxin families. For example, some antitoxins of the Phd antitoxin family may interact with particular toxins that can belong to, for example, MazF, Doc, PIN, and/or RelE toxin families, and some toxins of the RelE toxin family may interact with particular antitoxins of any of the HTH, MJ1172-like, StbD/axe, and RHH antitoxin families. Other type II TASs, and methods for identifying the TAS and its toxin/antitoxins, are described, e.g., by Makarova (2009) Biology Direct 4, 19, and Melderen (2009) PloS Genetics, 5, 3.

The toxin genes, in some embodiments of the present invention, can encompass txe (SEQ ID NO:1; protein SEQ ID NO:2) and doc (SEQ ID NO:3; protein SEQ ID NO:4) derived from Synechococcus, mazF (SEQ ID NO:5, protein SEQ ID NO:6) derived from Anabaena (also called Nostoc), hicA (SEQ ID NO:7, protein SEQ ID NO:8) and vapC (SEQ ID NO:9, protein SEQ ID NO:10) derived from Nostoc, and pemK (SEQ ID NO:11, protein SEQ ID NO:12) derived from *Microcystis aeruginosa*. The antitoxin genes, in some embodiments of the present invention, can encompass axe (SEQ ID NO:13; protein SEQ ID NO:14) and phd (SEQ ID NO:15; protein SEQ ID NO:16) derived from Synechococcus, mazE (SEQ ID NO:17; protein SEQ ID NO:18) derived from Anabaena, hicB (SEQ ID NO:19, protein SEQ ID NO:20) and vapB (SEQ ID NO:21; protein SEQ ID NO:22) derived from Nostoc, and pemI (SEQ ID NO:23, protein SEQ ID NO:24) derived from *Microcystis aeruginosa*. Additional nonlimiting examples from *E. coli* include mazF (SEQ ID NO:70; protein SEQ ID NO:72) or its sequence-altered mazF-insensitive version (SEQ ID NO:69); pemK (SEQ ID NO:73; protein SEQ ID NO:75), or its sequence-altered pemK-insensitive version (SEQ ID NO:74); and YafQ (SEQ ID NO:78; protein SEQ ID NO:80), or its sequence-altered pemK-insensitive version (SEQ ID NO:79).

For example, a gene having a homology, in terms of the amino acid sequence, to a toxin having an endoribonuclease activity to recognize a specific nucleotide sequence and cleave mRNA (e.g., PemK) can be a candidate for the toxin gene to be inserted into the microorganism. For example, such a gene can be derived from the group of cyanobacteria, such as *Synechocystis*. Such genes include those defined herein as belonging to the PemK gene family. Another toxin of the PemK family has been found in *Pyrococcus horikoshii*.

However, genes coding for toxins of other proteic killer systems, and which are therefore functional equivalents of the pemK family toxins, can additionally or alternately be used in accordance with the invention for controlling the growth and/or survival of microorganism. Such genes can include genes coding for the RelE toxin family, for the ParE toxin family, and for the Doc toxin family, as described by Jensen (1995) *Mol. Microbiol.* 17, 211-220.

It will be understood that in this context, the term "functional equivalent" includes variants and/or derivatives of any of the above toxins the sequences of which have been modified by substitution, deletion, or addition of one or more amino acids and the gene product of which has retained at least part of the function of the gene product of the non-modified sequence.

Genes coding for functional equivalents of the PemI antitoxin can be used in accordance with the invention for controlling the growth and/or survival of microorganism. Such genes can include the genes coding for the RelB antitoxin family, CcdA antitoxin family, the ParD antitoxin family, and the Phd antitoxin family.

Since there may be some differences in DNA sequences between the genera and/or strains of cyanobacteria, the toxin and/or antitoxin gene(s) may not necessarily be limited to the genes specified herein, but may include homologs (e.g., orthologs) of these genes or other toxin and/or antitoxin family members, as well as homologous genes encoding variant proteins of the toxin and/or antitoxin family described herein. Particularly, the sequence identity can be at least about 55%, for example at least about 65%, at least about 75%, at least about 85%, at least about 90%, at least about 95%, at least about 98%, at least about 99%, or about 100%.

As used herein a "homolog" of a gene is related to the reference gene by descent from a common ancestral gene. "Ortholog", as used herein, refers to a gene derived from a common ancestral gene, in which the genes have approximately similar function(s); thus "ortholog" can be used to refer to the same gene in a different species.

Homology/Identity at the nucleotide/amino acid sequence level can be determined by BLAST (Basic Local Alignment Search Tool) analysis using the algorithm employed by the programs blastp, blastn, blastx, tblastn, and tblastx (Altschul (1997), Nucleic Acids Res. 25, 3389-3402, and Karlin (1990), Proc. Natl. Acad. Sci. USA 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), Nature Genetics 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), Proc. Natl. Acad. Sci. USA 89, 10915-10919), recommended for query sequences over 85 in length (nucleotide bases or amino acids).

For blastn, designed for comparing nucleotide sequences, the scoring matrix is set by the ratios of M (i.e. the reward score for a pair of matching residues) to N (i.e. the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

In some further embodiments, a nucleotide sequence of the toxin and/or antitoxin gene(s) of the invention may be mutated, e.g., so as to increase biological activity and/or enhance interactions. Such mutations can include, but are not limited to, codon optimization to enhance expression of the wild-type sequence in transgenic cyanobacteria (e.g. Burgess-Brown (2008) Protein Expr. Purif. 59, 94-102) and mutations resulting from site specific mutagenesis to alter the amino acid sequence of the toxin and/or antitoxin gene(s). Such alteration in amino acid sequence can increase the biological activity and/or enhance the specificity of the toxin and/or antitoxin gene(s) in one or more species of prokaryotic microorganism.

In some particular examples, a toxin gene encodes an “RNA interferase” i.e., a protein having riboendonucleolytic activity, and the nucleotide sequence of a toxin gene can be mutated, so as to reduce or eliminate the susceptibility of the toxin transcript itself from being degraded by the toxin protein. Such preferably are performed to maintain the amino acid sequence of the encoded toxin protein, or if amino acid changes are introduced, the amino acid changes do not reduce the activity of the toxin. For example, the MazF toxin of *E. coli* (SEQ ID NO:70) is a ribonuclease that recognizes the sequence ACA in RNA transcripts. The ACA sequence can be entirely eliminated from the toxin coding sequence (altered sequence provided in SEQ ID NO:69), as shown in FIG. 7. Another example is the pemK toxin of *E. coli* (SEQ ID NO:75), a ribonuclease that recognizes the sequence: UA(A/C/U) in RNA transcripts. The UA(A/C/U) sequence can be entirely eliminated from the toxin coding sequence (altered sequence provided in SEQ ID NO:69), as shown in FIG. 8. Yet another example is the YafQ toxin of *E. coli* (SEQ ID NO:80), which cleaves after an AAA codon, when the AAA codon is followed by A or G. A YafQ toxin gene engineered to exclude ACA sequences (MazF recognition) and AAA codons followed by A or G, is provided in FIG. 9. Such sequence alterations can render the toxin RNA transcript insensitive to the endonucleolytic activity of its own encoded toxin, thereby prolonging the toxic effects and reducing the likelihood of persistence through conditions where the toxin is expressed (e.g., nutrient limitation). Directed mutations, such as those removing toxin target sequences, can be done, for example, by polymerase chain reaction, chemical synthesis, or any convenient means.

A given nucleic acid sequence may also be modified, for example, according to standard mutagenesis or artificial evolution or domain swapping methods to produce modified sequences. Accelerated evolution methods are described, e.g., by Stemmer (1994) Nature 370, 389-391, and Stemmer (1994) Proc. Natl. Acad. Sci. USA 91, 10747-10751. Chemical and/or enzymatic alteration of expressed nucleic acids and polypeptides can be performed by standard methods. For example, a sequence can be modified by addition of phosphate groups, methyl groups, lipids, sugars, peptides, organic and/or inorganic compounds, by the inclusion of modified nucleotides or amino acids, by the like, or by combinations thereof. Further the toxin and/or antitoxin gene(s) may be derived from a collection of transcripts, such as a cDNA library, and the sequence of the transcript may be unknown.

The “nucleic acids” or “nucleic acid molecules” of the invention can be DNA or RNA, for example, mRNA. The nucleic acids may be single- or double-stranded molecules, i.e., DNA; RNA; DNA-DNA, DNA-RNA, or RNA-RNA hybrids; protein nucleic acids (PNAs) formed by conjugating bases to an amino acid backbone; or the like. Nucleic acids may additionally or alternately be oligonucleotides, such as antisense oligonucleotides, chimeric DNA-RNA polymers, and ribozymes, as well as modified versions of these nucleic acids wherein the modification may be in the base, the sugar moiety, the phosphate linkage, or in any combination thereof. The nucleic acids may comprise an essential gene or fragment thereof, in which the target cell or cells may be deficient in some manner. This can occur where the gene may be lacking or where the gene may be mutated resulting in under- or over-expression. The nucleic acids may comprise antisense oligonucleotides, e.g., which can be constructed to inhibit expression of a target gene. If desired, the nucleotide sequence of the isolated nucleic acid can include additional non-coding sequences, such as non-coding 3' and 5' sequences (including regulatory sequences, for example).

The invention can also relate to fragments of the isolated nucleic acid molecules described herein, which can encompass a portion of a nucleotide sequence described herein, which can be at least about 20 contiguous nucleotides, for example from about 20 to about 50 contiguous nucleotides or at least about 50 contiguous nucleotides in length. Such fragments may be useful as probes and/or primers. In particular, primers and probes may selectively hybridize to the nucleic acid molecule encoding the polypeptides described herein. For example, fragments which encode polypeptides that retain activity, as described below, can be particularly useful.

The invention can also relate to nucleic acid molecules that can hybridize under high stringency hybridization conditions, such as for selective hybridization, to the nucleotide sequences described herein (e.g., nucleic acid molecules which can specifically hybridize to a nucleotide sequence encoding polypeptides described herein). Hybridization probes can include synthetic oligonucleotides which can bind in a base-specific manner to a complementary strand of nucleic acid. Suitable probes can include polypeptide nucleic acids, as described in Nielsen (1991) Science, 254, 1497-1500.

Such nucleic acid molecules can be detected and/or isolated by specific hybridization, e.g., under relatively high stringency conditions. "Stringency conditions" for hybridization is a term of art that refers to the incubation and wash conditions, e.g., conditions of temperature and buffer concentration, which permit hybridization of a particular nucleic acid to a second nucleic acid; the first nucleic acid may be perfectly complementary, i.e. 100%, to the second, or the first and second may share some degree of complementarity, which is less than perfect, e.g. 60%, 75%, 85%, 95%, or more. For example, certain high stringency conditions can be used to distinguish highly/perfectly complementary nucleic acids from those of less complementarity.

"High stringency conditions", "moderate stringency conditions", and "low stringency conditions" for nucleic acid hybridizations are explained in Current Protocols in Molecular Biology (2011) John Wiley & Sons). The exact conditions which determine the stringency of hybridization depend not only on ionic strength (e.g., ~0.2×SSC or ~0.1×SSC of the wash buffers), temperature (e.g., ~23° C., ~42° C., ~68° C., etc.), and the concentration of destabilizing agents (such as formamide) and/or denaturing agents (such as SDS), but also on factors such as the length of the nucleic acid sequence, base composition, percent mismatch between hybridizing sequences, the frequency of occurrence of subsets of that sequence within other non-identical sequences, and the like. Thus, high, moderate, or low stringency conditions may be determined empirically.

By varying hybridization conditions from a level of stringency at which no hybridization occurs to a level at which hybridization is observed, conditions which can allow a given sequence to hybridize with the most similar sequences in the sample can be determined.

Exemplary conditions are described in Krause (1991) Methods in Enzymology, 200, 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, can allow an increase by about 1% in the maximum extent of mismatching among the sequences that hybridize. Generally, doubling the concentration of SSC can result in an increase in Tm. Using these guidelines, the washing temperature can be determined empirically for high, moderate, or low stringency, depending on the level of mismatch sought. Exemplary high stringency conditions can include, but are not limited to, hybridization in ~50% formamide, ~1M NaCl, ~1% SDS at about 37° C., and a wash in ~0.1× SSC at about 60° C. Example of progressively higher stringency conditions include, after hybridization, washing with ~0.2×SSC and ~0.1% SDS at about room temperature (low stringency conditions); washing with ~0.2×SSC, and ~0.1% SDS at about 42° C. (moderate stringency conditions); and washing with ~0.1×SSC at about ~68° C. (high stringency conditions). Washing can be carried out using only one of these conditions, e.g., at high stringency conditions, or washing may encompass two or more of the stringency conditions, e.g., in order of increasing stringency. Optimal conditions can vary, e.g., depending on the particular hybridization reaction involved, and can typically be determined empirically.

Equivalent conditions can be determined by varying one or more of the parameters given as an example, as known in the art, while maintaining a similar degree of identity/similarity between the target nucleic acid molecule and the primer/probe used. Hybridizable nucleotide sequences can be useful as probes and/or primers for identification of organisms comprising a nucleic acid of the invention and/or to isolate a nucleic acid of the invention, for example.

Heterologous Regulatory Element

The present invention relates in some aspects to a microorganism such as a eukaryotic alga or cyanobacterium comprising an exogenous nucleic acid molecule encoding a Type II toxin in which the toxin gene can be operably linked to a heterologous regulatory element, such as a promoter. Additionally, the microorganism engineered for biocontainment can include an antitoxin gene, that can be and exogenous antitoxin gene or, for example (in the case of a prokaryotic microorganism) an endogenous antitoxin gene, where the antitoxin gene can be operably linked to a heterologous promoter. In additional or alternate aspects, the invention can involve antitoxin antisense constructs, in which the antitoxin antisense sequence can be operably linked to a heterologous regulatory element, such as a promoter.

In further additional or alternate aspects, the present invention relates to a prokaryotic microorganism comprising an endogenous toxin-antitoxin system (TAS) in which at least one heterologous regulatory element can be operably linked to a toxin gene, e.g., of an antitoxin-toxin operon.

Promoters considered for use in regulating toxin or antitoxin genes in eukaryotes can include, without limitation, an inducible promoter such as a GAL1, MET25, Lys7, or Leu promoter, or a nmtl thiamine-repressible promoter, a uracil regulatable promoter (e.g., Watt et al. (2008) PLoS One 3: e1428) for example from a yeast or fungus, a Tet-On or Tet-Off promoter, a CYC6 (copper regulated), NIT1 (ammonia regulated), or CA1 promoter ($CO_2$-regulated) from algae (Ferrante et al. (2008) PLos one 3: e3200), as well as an algal Pnr (nitrogen-regulated) (Poulsen and Kroger (2005) FEBS J. 3413-3423), an algal inorganic phosphate transporter promoter (Wurch et al. (2011) Environ. Microbiol. 113: 468-481), or phosphate-status regulated promoter from algae, e.g, a PNP or PSR promoter (Yehudai-Resheff et al. (2007) The Plant Cell 19: 1023-1038) Also considered for use in regulating antitoxin genes are the Nannochloropsis promoters disclosed in co-pending U.S. patent application Ser. No. 13/486, 930, entitled "Promoters and Terminators for Use in Eukaryotic Cells" filed Jun. 1, 2012. Specifically considered are promoters of the genes know to be regulated under particular conditions, e.g., nutrient status and promoters of their orthologs in other species. For example, a gene of one algal species can be used to identify its ortholog in a second algal species, and the promoter of the gene in the second species can be isolated and tested for its regulation in response, for example, to nutrient availability.

The promoter can be a promoter that is functional in a eukaryotic cell, and can be a promoter that is responsive to the depletion of one or more nutrients from the growth environment. For example, the promoter can be induced when the cells, which may be, for example, eukaryotic algae, reach nitrogen limitation. Examples of promoters that may be inducec by nitrogen limitation include but are not limited to: nitrate reductase promoters (Poulsen and Kroger (2005) FEBS J. 272: 3413-3423), ammonium or ammonia transporter gene promoters (see, for example, Wurch et al. (2011) Environ Microbiol. 13: 468-481); glutamine synthetase transporters (e.g., Miller et al (2010) Plant Physiology 154: 737-52) or other promoters of genes upregulated at the transcriptional level during nitrogen starvation, including those disclosed herein and provided as SEQ ID NO:56, SEQ ID NO:57, SEQ ID NO:58, SEQ ID NO:59, SEQ ID NO:60, and SEQ ID NO:61, or active fragments thereof. The promoter can alternatively or in addition be regulated by phosphate depletion, a PNPase gene promoter (Yehudai-Reseheff et al. (2007) The Plant Cell 19: 1023-1038); an inorganic phosphate transporter gene promoter (Wurch et al. (2011) Environ Microbiol. 13: 468-481) or a phosphate permease gene promoter (e.g., SEQ ID NO:65). Candidate copper depletion-regulated promoters include those of CTR-type copper ion transporter genes (Castruita et al (2011) The Plant Cell 23: 1273-1292), as well as CYC6 and CPX1 algal promoters (Quinn et al. (2000) J. Biol. Chem. 275: 6080-6089). Promoters regulated by iron deficiency may include, for example, the FOX1 gene or the FTR1 gene (La Fontaine et al. (2002) Eukaryotic Cell 1: 736-757).

A promoter used to regulate a toxin or antitoxin gene in a eukaryote can also be a synthetic promoter, for example, a promoter that includes a DNA binding domain that can be recognized and bound by an engineered transcription factor positioned upstream of a minimal promoter that is operable in the host microorganism. The microorganism can include an exogenous gene encoding a synthetic transcription factor that binds the synthetic promoter. The synthetic transcription factor can include, in addition to a DNA binding domain that recognizes the synthetic promoter, an activation domain (e.g., VP16, CREB, GAL10, GCN4) and a regulatory domain, where the regulatory domain may bind one or more compounds that can be added to the culture medium to induce or repress transcription (Weber and Fussenegger (2011) Curr Opinion in Chem. Biol. 15: 414-420).

In prokaryotic microorganisms, regulatory sequences can be used to alter gene expression of endogenous TASs. As used herein, an "endogenous" TAS of a microorganism refers to a TAS that is native to the microorganism, whereas an "exogenous" gene, for example, refers to a gene that was introduced into the microorganism (and/or its progenitor) by human intervention. "Homologous" means from the same species, whereas "heterologous" refers to a nucleic acid molecule or protein from a different species. A "heterologous" promoter or gene regulatory element, however, refers to a promoter or regulatory element operably linked to a gene to which the promoter or regulatory element is not operably linked in nature. "Operable linkage" is a functional linkage between two nucleic acid sequences, such as the regulatory element and the linked sequence, which is typically a sequence that encodes a protein and/or functional RNA (e.g., an antisense RNA or dsRNA). Therefore, a promoter is in operable linkage with a toxin gene if it can mediate transcription of the toxin gene. In particular, in some embodiments, a heterologous regulatory element described herein can be inserted into the genome of the prokaryotic microorganism upstream of a toxin gene. In some further embodiments, an inserted heterologous regulatory element can additionally or alternately located downstream of the antitoxin gene.

A regulatory element may be, for example, a promoter, an enhancer, and/or a transcriptional terminator. In particular, according to some embodiments of the present invention, a regulatory element operably linked to the toxin gene described herein may comprise a promoter that can direct expression of the toxin gene.

To insert a heterologous regulatory element upstream of the toxin gene of an endogenous TAS operon, e.g., between the antitoxin gene and the toxin gene which in many instances have a short (e.g., one to ten nucleotide) sequence overlap, a homologous recombination construct can be designed that can include, in tandem, the 3' end of the antitoxin gene, the heterologous regulatory element that can include a promoter, and the 5' end of the toxin gene, where the antitoxin/toxin gene overlap can in effect be repeated on either side of the heterologous regulatory element sequence, so that, in the integration construct, the regulatory region (e.g., promoter) can be between separated complete antitoxin and toxin genes, which can then be reflected in the organization of the engineered TAS operon in the host genome. This structure can then be present in the host genome following homologous recombination. Further, a terminator can optionally be inserted 3' of the antitoxin gene (and 5' of the heterologous promoter operably linked to the toxin gene). Accordingly, in some embodiments, the regulatory element comprising a promoter described above can further comprise a transcriptional terminator upstream of the promoter, such that the transcriptional terminator may be operably linked to an antitoxin gene upstream of the toxin gene. The terminator can advantageously inhibit/prevent inappropriate transcription of the toxin gene. For example, one of the suitable terminators can be the rpoCt transcription terminator isolated from the plasmid pHBA 102rpoCt (Squires (1981) Nucleic Acid Res. 9, 6827-6839). More examples of possible terminators include, but are not limited to, psbA, psaAB, rbc, secA, T7 coat protein, rrnB, and the like, and combinations thereof.

In accordance with the invention, the promoter described herein may be an inducible promoter or a regulatable promoter, i.e., a promoter that mediates transcription of an operably linked gene in response to a particular stimulus, e.g., by induction, repression, and/or derepression. Unless otherwise indicated, the terms "induction", "induced", "inducing", and the like as used herein are also understood to include "derepression", "derepressed", "derepressing", and the like. The activity of the inducible promoter can be regulated by one or more promoter-regulating factors. These factors either may include factors which by their presence can ensure expression of the gene coding for a toxin and/or antitoxin protein or may, alternately, include factors which can suppress the expression of the gene so that their absence causes the polypeptide to be expressed.

Various factors may affect/regulate the activity of the promoter. Thus, the expression of the gene encoding a toxin and/or antitoxin protein may be determined by the cell culture, by cell environmental conditions, and/or by the physiological state of the cells. The term "physiological state of the cells" denotes factors such as cell density and the growth phase of cells.

In accordance with the invention, a promoter in some embodiments can be regulated by promoter regulating factors, such as the presence or absence of a chemical substance or compound in the cell culture or external environment, i.e., may be present outside the contained culture conditions. In some embodiments, the promoter described herein can be regulated by the physical conditions in the environment, such as the prevailing temperature and/or other physical factors (e.g., the intensity of the light in the environment). For example, in various containment systems contemplated herein, the gene coding for the toxin protein and/or an antitoxin antisense construct can be expressed when a certain chemical substance/compound, present in a first cell culture/environment in which the cell is propagated, is absent from a second environment in which growth of the cell is undesirable, and/or when a factor required for the growth and/or survival of the cell is no longer present and/or when the factor is one which, when it is depleted/exhausted from an environment of the cell, results in an active toxin and/or an antitoxin antisense construct being expressed. The promoter regulating the transcription of the gene coding for the cytotoxic polypeptide and/or antoxin antisense sequence may additionally or alternately become activated in a second environment of the cell, e.g., by a chemical substance/compound which is not present in a first environment of the cell, but which is present in the second environment in sufficient quantities to activate the promoter. Further additionally or alternately, the promoter may be activated by a shift in temperature, such as a shift from a higher temperature in a first environment, e.g., a fermentation vessel, to a lower temperature prevailing in an outside second environment, and/or by a shift in light intensity, in that the promoter may be activated in the presence of light of sufficient intensity, but may remain inactive under standard cultivation conditions in which the light is less intense and/or in which the cells are not sufficiently (continuously) exposed to the light of sufficient intensity.

In embodiments in which more than one toxin gene expression construct, engineered endogenous TAS operon, and/or antitoxin antisense construct is/are used, multiple promoters (at least one of which is and/or all of which are heterologous) can be employed, in which the promoters can be induced/regulated by different compounds of conditions. In this way, backup systems for controlling cell proliferation can be designed into the microorganism. For example, a first endogenous toxin gene of a TAS operon may be operably linked to a promoter induced by the absence of a culture nutrient, a second exogenous toxin gene may be operably linked to a heterologous promoter induced by the presence of a metal and/or organic compound, and an antitoxin gene antisense construct may be regulated by a promoter responsive to high light intensity. Various combinations of heterologous promoters, endogenous and exogenous toxin genes, and antitoxin antisense constructs can thus be envisioned.

In case of chemically regulatable promoters, the chemical substance or compound, the presence or absence of which can determine the activation of the promoter, can be suitably selected from carbon and/or nitrogen sources, metabolites, amino acids, nucleosides, purine and/or pyrimidine bases, metal ions, or the like, or combinations thereof. In particular, the chemical substance/compound described herein can be a sugar, an organic acid, a fatty acid, a lipid, a hydrocarbon, phosphate, nitrate, ammonium, a metal, a quorum-sensing compound, a synthesized/secreted protein and/or peptide, or any combination thereof. When the chemical substance or compound is one which, when present, suppresses promoter activity, it can preferably comprise or be a substance that rarely occurs naturally in such concentrations that the promoter activity would be suppressed when the cell is released to the natural environment. One example of such a promoter is the trp promoter which is repressed in the presence of tryptophan in the environment of the cell, but which is derepressed in the absence of sufficient amounts of tryptophan in the environment. A containment system according to the invention using the trp promoter or another promoter being regulated in the same manner, might therefore comprise an amount of tryptophan in a first environment, such as a fermentation vessel, sufficient to repress the promoter in such an environment, the promoter, however, being derepressed when the cell is released from the first environment to a second environment, e.g., the outer environment, which usually contains very low amounts of tryptophan or no tryptophan at all.

Other useful promoters isolated from bacterial operons include L-arabinose inducible promoters, including that contained in the plasmid pBAD (Guzman (1995) J. Bacteriol. 177, 4121-30). Without L-arabinose added to the growth medium, the pBAD promoter is typically completely turned off. However, in the presence of L-arabinose, strong transcription can be induced. This particular promoter is repressible by the addition of glucose to the growth medium. Thus, by the addition of glucose, transcription from pBAD can be rapidly and efficiently inhibited and/or turned off. The glucose repression effect can be epistatic to the inducer effect by L-arabinose. Hence, if cells with a pBAD-carrying plasmid are grown in a medium containing both L-arabinose and glucose, the promoter is typically not induced. However, if cell growth depletes the medium for glucose, then the promoter can generally be induced upon sufficient depletion. Therefore, such a plasmid may be suitable for conditionally turning on and off the expression of a gene, in particular a toxin-encoding gene as described herein. In some species, it may be necessary to introduce the araC gene into the host microorganism for regulated expression from the pBAD promoter. In some species, it may be desirable to introduce an L-arabinose transporter gene into the host microorganism to enable regulated expression from the pBAD promoter.

The invention can employ methods for containing microbial cells in which the cells including a toxin gene and/or antisense construct under the control of a promoter can be suppressible by a first kind of chemical compound and inducible by a second kind of chemical compound, whereby, when the first kind of compound is depleted from the medium, the promoter can be induced by the second kind of compound.

Another example of a regulatable promoter, the activation of which can be determined by a chemical substance/compound, is the lac promoter which is inducible, e.g., by isopropyl-β-D-thiogalactopyranoside (IPTG). Additional exampes of regulatable promoters can include, but are not limited to, a tet promoter (e.g., U.S. Pat. No. 5,851,796), a trp promoter, a hybrid promoter that includes either or both of portions of a tet, trp, or lac promoter. The promoter sequences can be from any organism, provided that it is functional in the host organism. Regulatable promoters can use one or more portions/domains of the aforementioned promoters and/or other regulatable promoters fused to at least a portion of a different promoter that can operate in the host organism, e.g., to confer inducibility on a promoter that can operate in the host species.

A variety of promoters that function in a prokaryotic microorganism can be utilized, including, but not limited to, the lac, tac, and trc promoters, as well as derivatives such as but not limited to the trcE and trcY promoters that are inducible by the addition of isopropyl β-D-1-thiogalactopyranoside (IPTG), promoters that are naturally associated with transposon- and/or bacterial chromosome-borne antibiotic resistance genes (e.g., neomycin phosphotransferase, chloramphenicol acetyltransferase, spectinomycin adenyltransferase, or the like, or combinations thereof), promoters associated with various heterologous bacterial and native cyanobacterial genes, promoters from viruses and phages, synthetic promoters, or the like, or combinations thereof. Examples of such promoters can include, but are not limited to, promoters isolated from cyanobacteria such as the following: secA (secretion; controlled at least in part by the redox state of the cell), rbc (Rubisco operon), psaAB (PS I reaction center proteins; light regulated), NtcA, glnA, or glnB promoter, and psbA (Dl protein of PSII; light-inducible). Other examples can include promoters regulated by nitrogen compounds, such as, for example, nar, ntc, nir, or nrt promoters. Further examples can include pho and/or pst promoters regulated by phosphate, and an nrs promoter responsive to nickel. Promoters for use in cyanobacteria can additionally or alternately be modified from naturally-occurring promoters, and can include combinations of naturally-occurring promoters, including, but not limited to, those disclosed herein. Still further examples can include prokaryotic promoters from a range of species, including eubacterial and cyanobacterial species, such as, for example, a Pm promoter, an ara promoter, a rha promoter, a nir promoter, a nar promoter, a pho promoter, a tet promoter, a cys promoter, a metallothionien promoter, an ftf promoter, a gin promoter, a heat shock promoter, a cold-inducible promoter, a viral promoter, or the like, or a combination thereof. The foregoing lists are exemplary and not limiting.

Further, as mentioned above, the regulatable promoter may be regulated by the temperature prevailing in the environment of a cell containing the gene coding for the toxin and/or antoxin proteins and a regulatable promoter regulating the expression of the gene. In such a case, the regulation of the promoter can advantageously be obtained by the presence in the cell of a gene coding for a temperature sensitive repressor for the promoter. As one typical example, the λ promoters including those mentioned above may be regulated by a temperature sensitive λcI repressor that can also be expressed in the host cell.

The present invention in some embodiments relates to a prokaryotic microorganism containing a heterologous regulatory element operably linked to a toxin gene of an endogenous TAS, where the regulatory element comprises a first promoter directing expression of the toxin gene and a second promoter directing expression of a nucleic acid sequence encoding an antisense oligonucleotide that hybridizes with a portion of the antitoxin gene of the endogenous TAS. In some embodiments, this second promoter can be located downstream of the antitoxin gene. In various embodiments, the second promoter of the present invention can be regulated by the same or a different compound as the promoter that directs expression of the toxin gene. For example, one promoter can be regulated by the presence of an inducer, such as a metal, while another promoter can be regulated by lack of a nutrient, such as phosphate or ammonia.

The present invention can further relate to a prokaryotic microorganism containing a heterologous regulatory element operably linked to a toxin gene of an endogenous TAS, where the regulatory element comprises a bidirectional promoter that can direct expression of the toxin gene and expression of a nucleic acid sequence encoding an antisense oligonucleotide that can hybridize with a portion of the antitoxin gene of the endogenous TAS. By utilizing the bidirectional promoter, the toxin can be tightly regulated, and simultaneously the antisense oligonucleotide can be expressed, thus regulating the expression of the antitoxin gene.

As used herein, the term "bidirectional promoter" refers to a promoter capable of directing transcription in both the forward and reverse orientations. Bidirectional promoters can direct the transcription of two transcripts placed in either orientation (i.e., downstream or upstream) of the promoter simultaneously (e.g., the "sense" and "antisense" strands of a gene). In other words, a bidirectional promoter can direct transcription from either strand of the promoter region, such as for, example, the fepD-ybdA promoter of E. coli, which, in the presence of the protein encoded by the fur gene, can be regulated by iron (J. Bacteriol. 183: 2059-2070 (2001)). The bidirectional promoter can be a naturally occurring bidirectional promoter or a naturally occurring unidirectional and/or polar promoter that can be converted into a bidirectional promoter, e.g., by the method shown in Xie (2001) Nature Biotechnology, 19, 677-679.

Since there may be differences in promoter sequences between the genera and/or strains of prokaryotic microorganisms such as, for example cyanobacterial species, promoters are not limited to the sequences of particular promoters specified herein, but may include promoters which, in various species including a host species of the invention, can be operably linked to a gene encoding the same protein as regulated by an exemplary promoter described herein.

Antisense Oligonucleotides

The present invention relates to a nucleic acid sequence encoding an antisense oligonucleotide hybridizing with an antitoxin gene of an endogenous TAS. In accordance with the invention, the expression of the nucleic acid sequence encoding an antisense oligonucleotide that can hybridize with at least a portion of the antitoxin gene can regulate the expression of the antitoxin gene. In particular, the expression of the nucleic acid sequence encoding an antisense oligonucleotide that can hybridize with at least a portion of the antitoxin gene can inhibit and/or prevent expression of the antitoxin protein.

In one embodiment, an antisense RNA refers to a nucleic acid that has substantial or complete identity to a target gene. The sequence of the antisense RNA can correspond to the full length target gene, or to a subsequence thereof.

The nucleic acid sequence encoding an antisense oligonucleotide according to some embodiments of the present invention can hybridize with an antitoxin gene of an endogenous TAS as described herein, including, but not limited to, the antitoxin genes encoding a polypeptide having antidote activity that is a member of HicB antitoxin family, PemI antitoxin family, CcdA antitoxin family, RelB antitoxin family, MazE antitoxin family, ParD antitoxin family, RHH antitoxin family, ArsR antitoxin family, HEPN antitoxin family, Phd antitoxin family, VapB antitoxin family, epsilon antitoxin family, HipB antitoxin family, HigA antitoxin family, HTH antitoxin family, MJ1172-like antitoxin family, or StbD/axe antitoxin family. Additionally or alternately, the nucleic acid sequence encoding an antisense oligonucleotide according to the present invention can generally hybridize with an antitoxin gene that is a homolog (e.g., an analog) of axe, phd, mazE, hicB, vapB, pemI, relB, parD, kiS, ccdA, yafN, stbD, yoeM, or PIN.

As used herein, an "antisense oligonucleotide" refers particularly to a nucleic acid, e.g., ribonucleotide, sequence of at least a portion of the non-coding strand of a double stranded DNA molecule of a gene that encodes a protein, or to a sequence substantially homologous to at least a portion of the non-coding strand. As used herein, an antisense sequence can be complementary to the sequence of the coding strand of at least a portion of a double stranded DNA molecule encoding a protein. It is not required that the antisense sequence be complementary to the coding portion of the coding strand of the DNA molecule, or even complementary solely to the coding portion of the coding strand of the DNA molecule. In some embodiments, the antisense sequence may be complementary wholly or in part to noncoding sequences specified on the transcribed strand of a DNA molecule encoding a protein, for example, a 5' untranslated region (UTR) and/or intron. "Complementary," as used herein, refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids can be complementary to each other when a substantial number (e.g. at least about 50%, at least about 60%, at least about 70%, at least about 80%, at least about 85%, at least about 90%, at least about 95%, at least about 98%, at least about 99%, or about 100%) of corresponding positions in each of the molecule, are occupied by nucleotides which normally base pair with each other. Antisense oligonucleotides are preferably at least 85% complementary to the target nucleic acid sequence.

Multiple TASs

A prokaryotic microorganism in some embodiments of the present invention may contain two or more endogenous TAS. For example, genomes of *Nitrosomonas europeae, Sinorhizobium meliloti*, and *Mycobacterium bovis* may contain more than 50 putative TAS while some others contain less than three putative TAS, such as *Rickettsia prowazeki, Campylobacter jejuni*, or *Bacillus subtilis*. Further, genomes of some cyanobacterial species may contain various numbers of endogenous TAS pairs as analyzed by Makarova (2009) Biology Direct 4, 19 (Table 1 below).

TABLE 1

Total number of protein coding genes, toxin genes, antitoxin genes, and toxin-antitoxin systems in genomes of various cyanobacterial species.

| Species | No. proteins | Toxin & antitoxin genes detected | No. TAS pairs |
|---|---|---|---|
| *Cyanothece* sp. ATCC 51142 | 5304 | 306 | 50 |
| *Microcystis aeruginosa* NIES-843 | 6312 | 524 | 113 |
| *Synechococcus elongatus* PCC 6301 | 2527 | 56 | 9 |
| *Synechococcus elongatus* PCC 7942 | 2662 | 68 | 13 |
| *Synechococcus* sp. CC9311 | 2892 | 27 | 3 |
| *Synechococcus* sp. JA-2-3B'a(2-13) | 2862 | 50 | 1 |
| *Synechococcus* sp. JA-3-3Ab | 2760 | 47 | 1 |
| *Synechococcus* sp. PCC 7002 | 3186 | 137 | 29 |
| *Synechococcus* sp. WH 7803 | 2533 | 18 | 1 |
| *Synechococcus* sp. WH 8102 | 2519 | 42 | 11 |
| *Synechococcus* sp. PCC 6803 | 3569 | 175 | 30 |
| *Thermosynechococcus elongatus* BP-1 | 2476 | 20 | 1 |
| *Gloeobacter violaceus* PCC 7421 | 4430 | 304 | 56 |
| *Anabaena variabilis* ATCC 29413 | 5661 | 204 | 29 |
| *Nostoc punctiforme* PCC 73102 | 6690 | 266 | 28 |
| *Nostoc* sp. PCC 7120 | 6130 | 269 | 38 |
| *Trichodesmium erythraeum* IMS101 | 4451 | 60 | 6 |
| *Acaryochloris marina* MBIC11017 | 8383 | 235 | 32 |

Without limiting the invention to any particular mechanism, the inventors contemplate that the combination of two or more engineered TASs can reduce the risk of a strain becoming resistant to the effects of a toxin, for example, by spread of a mutation that results in a strain no longer responding to the lethal effect of the toxic gene/protein. For example, even when one TAS in a microorganism incurs a mutation, the other non-mutated TAS can still respond to the lethal effect of the toxic gene/protein, thus offering little if any selective advantage in survival to the singly mutated microorganism. Further, in some embodiments the combination of two or more TASs can increase the efficiency of a biological containment based on the combination of different cellular targets modulated by the two or more TASs in containment. In some embodiments, at least two of the toxin-antitoxin systems in an engineered prokaryotic microorganism can comprise the same or different (e.g., heterologous) promoters operably linked to the toxin genes and/or antitoxin antisense constructs of the TASs. In some embodiments, at least two of the engineered toxin and/or antitoxin genes in a prokaryotic microorganism described above can be operably linked to different heterologous promoters that can be regulated by different compounds and/or environmental conditions.

Multiple exogenous Type II toxin genes can also be introduced into eukaryotic or prokaryotic microorganisms. The exogenous Type II genes can be operably linked to the same promoter (e.g., different copies of the same promoter), or can be operably linked to different promoters that can be regulated by the saem or different conditions. For example, a first Type II toxin gene may be operably linked to a promoter that is repressed by the presence of a compound present in the culture medium, while a second Type II toxin gene may be operably linked to a promoter activated by nutrient depletion. Alternatively or in addition, two or more Type II antitoxin genes can be operably linked to different promoters regulated by depletion of the same or different nutrients. One, two, or more of the multiple exogenous Type II toxin genes of an engineered microorganism can be sequence-modified to exclude sequences that are targeted by one, two, or more of the Type II toxins encoded by the multiple toxin genes.

Vectors

"Expression vector" or "expression construct" refers to a nucleic acid that has been generated via human intervention, including by recombinant means and/or direct chemical synthesis, with a series of specified nucleic acid "expression control elements" that can permit transcription and/or translation of a particular nucleic acid in a host cell. The expression vector can be a plasmid, a part of a plasmid, a viral construct, a nucleic acid fragment, or the like, or a combination thereof. Typically, the expression vector can include a nucleic acid to be transcribed operably linked to a promoter in an expression cassette. In some embodiments, the present invention can involve prokaryotic microorganisms transformed with the heterologous regulatory element as described herein.

In various embodiments, the present invention relates to vectors that include a promoter sequence operably linked to a nucleic acid sequence encoding a toxin, and/or to an antisense oligonucleotide that can hybridize with a portion of an endogenous antitoxin gene of a toxin-antitoxin system. The vectors can be integration vectors, for example, having homology regions for integration into the host chromosome, and/or can be autonomously replicating vectors, such as episomes. In further embodiments, the vectors can include nucleic acid sequences for integration into the host genome that can include, in the following order, at least the 3' portion of an antitoxin gene of a TAS system/operon endogenous to the host organism, a heterolgous regulatory element, and at least the 5' portion of a toxin gene of the TAS system/operon.

In some embodiments of the invention, a gene encoding a toxin gene and/or an antitoxin gene/antisense construct can be cloned into an expression vector for transformation into a microorganism.

In accordance with the invention, a gene coding for a toxin of a TAS can be provided in the microorganism at a location where it can be expressed effectively. Thus, in some useful embodiments the gene can be present on the chromosome of the cells, whereas in other embodiments it can preferably be located on an extrachromosomal element such as a plasmid and/or episome. The microorganisms according to the invention may, in some specific embodiments, not contain a gene coding for an antitoxin capable of counteracting the cell toxic effect of the toxin or the functional equivalent hereof.

In other useful embodiments, the microorganism can comprise a gene coding for an antitoxin that can bind toxins of the toxin family of the introduced/engineered endogenous toxin gene (and/or the functional equivalent thereof), resulting in the lethal effect of the toxin being at least partially counteracted.

The invention also encompasses a vector for introducing a toxin gene into a microorganism in which the vector includes a toxin gene and a (cognate) antitoxin gene, where the toxin gene is in an integrating portion of the vector and the antitoxin gene is in a non-integrating portion of the vector. These toxin and antitoxin genes in some embodiments can be derived from a cyanobacterial species described herein. The vector can further include a regulatable promoter such as described herein that can control expression of the toxin gene. Alternately, if the vector does not contain a promoter in operable linkage with the toxin gene, the gene can be transformed into the cells such that it becomes operably linked to an endogenous promoter by homologous recombination, site specific integration, and/or vector integration. The vector can additionally or alternately include a constitutive promoter to control the antitoxin gene.

Transformation vectors can additionally or alternately include a selectable marker, such as but not limited to a drug resistance gene, an herbicide resistance gene, a metabolic enzyme and/or factor required for survival of the host (for example, an auxotrophic marker), or the like, or a combination thereof. Transformed cells can be optionally selected based upon the ability to grow in the presence of the antibiotic and/or other selectable marker under conditions in which cells lacking the resistance cassette and/or auxotrophic marker could not grow. Further additionally or alternatively, a non-selectable marker may be present on a vector, such as a gene encoding a fluorescent protein or enzyme that can generate a detectable reaction product.

A vector can additionally or alternately be an integration vector including one or more sequences that promote integration of a gene of interest (i.e., the exogenous gene to be transformed into the host microorganism) and/or the gene expression cassette into the genome of the host microorganism. For example, an integration vector used to transform cyanobacteria can include at least one sequence of at least 50, for example at least 100, at least 200, at least 300, at least 400, at least 500, or at least 600 nucleotides with homology to a sequence in the genome of the host organism to allow integration of the transgene and/or expression cassette into the genome of the host microorganism to occur via homologous recombination. In some examples, the transgene and/or expression cassette can be flanked by a sequence homologous to a region of the host chromosome, e.g., to promote integration of the gene of interest into the host chromosome. Alternatively or in addition, an integration vector can include one or more sequences that promote, site-specific recombination and/or random integration such as, but not limited to, (sequences recognized by) a recombinase, integrase, and/or transposase.

For optimal expression of a recombinant protein, in many instances it can be beneficial to employ coding sequences that produce mRNA with codons preferentially used by the host cell to be transformed. Thus, for an enhanced expression of transgenes, the codon usage of the transgene can be matched with the specific codon bias of the organism in which the transgene is desired to be expressed. For example, methods of recoding genes for expression in microalgae are described in U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic mRNA when this need is met. In some embodiments, only a portion of the codons can be changed to reflect a preferred codon usage of a host microorganism, and in some embodiments, one or more codons can be changed to codons that are not necessarily the most preferred codon of the host microorganism encoding a particular amino acid. Additional information for codon optimization is available, e.g. at the codon usage database of GenBank.

Accordingly, the present invention can provide, in some embodiments, recombinant microorganisms transformed with an isolated nucleic acid molecule as described herein including a nucleic acid sequence that is codon-optimized for expression in the recombinant microorganism.

Vectors can be introduced into microorganisms such as microalgae and cyanobacteria via conventional transformation and/or transfection techniques. Transformation and transfection, conjugation and transduction, as used in the present context, are intended to comprise a multiplicity of methods known to those skilled in the art for the introduction of foreign nucleic acid (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Examples of suitable methods for the transformation and/or transfection of host cells, e.g., can be found in Molecular Cloning—A Laboratory Manual (2010), Cold Spring Harbor Laboratory Press.

For example, microorganisms including cyanobacteria and microalgae can be transformed by any suitable methods, including, as nonlimiting examples, natural DNA uptake (Zang (2007) J. Microbiol. 45, 241-245), conjugation, transduction, glass bead transformation (Feng (2009) Mol. Biol. Rep. 36, 1433-9), silicon carbide whisker transformation (Dunahay (1997) Methods Mol. Biol. 62, 503-9), biolistics (Kroth (2007) Methods Mol. Biol. 390, 257-267), electroporation (Ludwig (2008) Appl. Microbiol. Biotechnol. 78, 729-35), laser-mediated transformation (WO2009/140701), incubation with DNA in the presence of or after pre-treatment with any of poly(amidoamine) dendrimers (Pasupathy (2008) Biotechnol. J. 3, 1078-82), polyethylene glycol (Ohnuma (2008) Plant Cell Physiol. 49, 117-120), cationic lipids (Muradawa (2008) J. Biosci. Bioeng. 105, 77-80), dextran, calcium phosphate, and/or calcium chloride (Mendez-Alvarez (1994) J. Bacteriol. 176, 7395-7397), optionally after treatment of the cells with cell wall-degrading enzymes (Perrone (1998) Mol. Biol. Cell 9, 3351-3365), or the like, or combinations thereof. *Agrobacterium*-mediated transformation can additionally or alternatively be performed on algal cells, for example after removing or wounding the algal cell wall (Kumar (2004) Plant Sci. 166, 731-738).

Recombinant Microorganism

The recombinant microorganisms of the present invention, in some embodiments, can be transformed with exogenous genes by the introduction of appropriate vectors described herein. In particular, the present invention in some embodiments can relate to a recombinant microorganism comprising an exogenous nucleic acid molecule including a nucleic acid sequence encoding a toxin gene operably linked to a heterologous promoter. In some embodiments, the toxin gene can be an "RNA interferase" or endonuclease that can cleave RNA at or near particular recognition sequences, and the sequence of the toxin gene can be designed (codon-optimized) such that the toxin gene does not include sequences that, when transcribed into RNA, are susceptible to degradation by the toxin. For example, in embodiments that employ a pemK gene, the sequence of the gene can be codon-modified to minimize and/or eliminate UAH sequences, where H can be C, A, or U. In certain embodiments, a mazF gene can be employed, and the sequence ACA can be avoided by use of alternative codons. In further embodiments, an axe gene can be introduced into the host microorganism, and the sequence AUG can be avoided by use of alternative codons. In yet further embodiments, a ChpI gene can be introduced into the host microorganism, and any of the sequences ACA, ACG, and ACU can be avoided, where alternative codons can be used to reduce the occurrence of these sequences in the gene. These examples are meant to be illustrative and not limiting.

A prokaryotic microorganism including an exogenous nucleic acid molecule encoding a toxin can preferably include an endogenous antitoxin gene, e.g., in which the antitoxin resulting from expression of the antitoxin gene can be cognate to the toxin resulting from expression of the toxin gene.

In some embodiments, the heterologous promoter operably linked to the exogenous toxin gene can be regulated by a compound, for example, a compound that can be present in the media or the environment, or can be regulated by an environmental condition. The present invention can also relate to a recombinant microorganism comprising an exogenous promoter operably linked to a nucleic acid sequence encoding an antisense oligonucleotide that can hybridize with at least a portion of an endogenous or exogenous antitoxin gene of the microorganism. In yet further embodiments, the invention can encompass a prokaryotic microorganism including an engineered TAS system and/or operon, e.g., in which an endogenous TAS system/operon can be modified through homologous recombination to include a heterologous regulatory element between the toxin and antitoxin genes. The heterologous regulatory element can be a promoter, such as a regulatable promoter, and can further include either or both of a transcriptional terminator and/or a second promoter upstream of the first promoter. A second promoter provided in the engineered operon can direct transcription in a direction opposite to that of the first promoter, and can optionally direct transcription of a sequence complementary to that of the antitoxin gene of the TAS system and/or operon. In yet other embodiments, particularly where the TAS operon contains both toxin and antitoxin genes, the heterologous regulatory element can a bidirectional promoter directing transcription of both the toxin gene and an antitoxin antisense sequence.

In some embodiments of the invention, a prokaryotic microorganism can have multiple endogenous TASs and, for instance, can be transformed with one or more exogenous nucleic acid molecules encoding a toxin operably linked to a heterologous promoter and/or one or more antitoxin antisense constructs, where the microorganism can include an endogenous gene encoding the antitoxin. Alternately or in addition, a prokaryotic microorganism can have multiple engineered endogenous TAS operons, in which a heterologous regulatory element has been inserted between the antitoxin and toxin genes of (each of) the respective operon(s), as described herein.

The invention in one aspect describes a prokaryotic microorganism, such as a cyanobacterium, comprising an exogenous nucleic acid molecule that includes a toxin gene in which at least one heterologous regulatory element is operably linked to the toxin gene. Optionally, the toxin gene may encode a ribonuclease, and in some embodiments the toxin gene can be sequence-optimized such that one or more sequences recognized by the toxin are replaced with sequences that are not targets of the endoribonuclease. The microorganism may in some embodiments further include an endogenous antitoxin gene, in which the antitoxin produced by the endogenous antitoxin gene can interact with (and typically can inactivate) the toxin produced by the introduced toxin gene. In these embodiments, biological containment of the transgenic cyanobacterium can be achieved by inducing and/or allowing transcription from the heterologous regulatory element, such that the toxin gene can be expressed.

The present invention in another aspect describes a prokaryotic microorganism including an endogenous TAS operon, in which the endogenous promoter of the TAS operon can be replaced with a heterologous, and preferably regulatable, promoter. For example, the promoter can be an inducible or derepressible promoter, such as, for example, any disclosed herein.

In still further embodiments the invention provides a recombinant prokaryotic microorganism including an exogenous nucleic acid molecule encoding an antitoxin operably linked to a heterologous promoter, in which the recombinant prokaryotic microorganism can include a TAS containing a gene encoding a toxin that is cognate to the antitoxin encoded by the exogenous nucleic acid molecule. In preferred embodiments, the heterologous promoter can be regulatable, for example, inducible and/or repressible. Additionally or alternately, the endogenous antitoxin gene of the TAS can be attenuated and/or inactivated, e.g., by homologous recombination.

In yet further aspects, provided herein is a recombinant prokaryotic microorganism that can include a prokaryotic microorganism comprising an antisense construct including an antisense sequence having homology to at least a portion of an antitoxin gene endogenous to the host. Regulated expression of the antisense sequence can result in lowered expression of the endogenous antitoxin, e.g., by allowing expression of an endogenous cognate toxin.

In yet other aspects, the invention provides a prokaryotic microorganism comprising an endogenous toxin-antitoxin system (TAS) in which at least one heterologous regulatory element is operably linked to the toxin gene of the endogenous TAS as described herein. The heterologous regulatory element can be a regulatable promoter, in some embodiments inserted between the antitoxin and toxin genes of a TAS operon. In such embodiments, a terminator may be provided upstream of the inserted heterologous promoter. In additional or alternative embodiments, a second heterologous promoter can be provided upstream of the first promoter, where the second promoter can direct transcription in an orientation opposite to that of the first promoter, and can thus direct transcription of an antitoxin antisense sequence. Further additionally or alternately, a bidirectional promoter can be inserted between the antitoxin and toxin genes of a TAS operon, in which the bidirectional promoter can direct expression of the toxin gene and an antisense sequence complementary to at least a portion of the antisense gene.

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences) and, often, the regulatory sequences required for their expression. Genes can be obtained from a variety of sources, including cloning from a source of interest or synthesizing from known or predicted sequence information and may include sequences designed to have desired parameters.

A "recombinant" or "engineered" nucleic acid molecule is a nucleic acid molecule that has been synthesized and/or altered through human manipulation. As non-limiting examples, a recombinant nucleic acid molecule: (1) can include conjoined nucleotide sequences that are not conjoined in nature, (2) may have been engineered using molecular cloning techniques such that it lacks one or more nucleotides with respect to the naturally occurring nucleic acid molecule sequence, or (3) may have been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms recombinant, engineered, and genetically engineered collectively refer to organisms that have been manipulated by introduction of a heterologous or recombinant nucleic acid sequence into the organism, and includes gene knockouts, targeted mutations and gene replacement, promoter replacement, deletion, or insertion, as well as introduction of transgenes and synthesized genes into the organism. The heterologous and/or recombinant nucleic acid molecule can be integrated into the recombinant/genetically engineered organism's genome or in other instances are not integrated into the recombinant/genetically engineered organism's genome.

The term "recombinant protein" as used herein refers to a protein produced by genetic engineering.

An "expression cassette" as used herein refers to a gene encoding a protein or functional RNA (e.g. tRNA, microRNA, ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc.

When referring to a gene regulatory sequence or to an auxiliary nucleic acid sequence used for maintaining or manipulating a gene sequence (e.g., a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome, or episome. Thus, a promoter operably linked to a gene to which it is not operably linked to in its natural state (i.e., in the genome of a non-genetically engineered organism) is referred to herein as a "heterologous promoter", even though the promoter may be derived from the same species (or, in some cases, the same organism) as the gene to which it is linked.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. (A descendent of a cell that was transformed with a nucleic acid molecule is also referred to as "transformed" if it has inherited the exogenous nucleic acid molecule.) The exogenous gene may be from a different species or synthesized (and so "heterologous"), or from the same species (and so "homologous"), relative to the cell being transformed. An "endogenous" nucleic acid molecule, gene, and/or protein represents the organism's own nucleic acid molecule, gene, and/or protein as it occurs in, or is naturally produced by, the organism.

The term "heterologous" is used broadly in this aspect to indicate that the nucleic acid molecules disclosed herein that are introduced into a prokaryotic microorganism can be synthesized or derived from an organism other than cyanobacteria. A heterologous regulatory element described herein may have an equivalent in the transformed host, i.e., one which normally performs the same or a similar function, or the exogenous heterologous regulatory element may not have an endogenous homologue in the host strain.

Nucleic acid molecules heterologous to a prokaryotic host strain may be nucleic acid molecules not naturally-occurring in cells of that type, variety, or species. In some embodiments, the heterologous regulatory element may comprise a coding sequence of, and/or derived from, an organism other than a prokaryotic microorganism.

Recombinant microorganisms or host cells of the invention may be of prokaryotic or eukaryotic origin, including, without limitation, fungi, heterokonts, algae, eubacteria, archaebacteria, green nonsulfur bacteria, purple nonsulfur bacteria, or cyanobacteria. Recombinant host cells can be, but are not limited to, photosynthetic organisms. Photosynthetic organisms include higher plants (i.e., vascular plants), bryophytes, algae, and photosynthetic bacteria. The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "picoplankton" (Prasinophyceae and Eustigmatophyceae). Also included in the term algae are members of the taxonomic classes Dinophyceae, Cryptophyceae, Euglenophyceae, Glaucophyceae, and Prymnesiophyceae. Microalgae are unicellular or colonial algae that can be seen as single organisms only with the aid of a microscope. Microalgae include both eukaryotic and prokaryotic algae (e.g., cyanobacteria). For example, considered herein are eukaryotic microalgae such as *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachorella, Tetraselmis, Thalassiosira, Viridiella,* or *Volvox* species.

A microorganism according to some additional embodiments of the present invention can be a prokaryotic microorganism, including without limitation, a *eubacterium*, archaebacterium, cyanobacterium, or the like. In particular, the microorganism that includes a heterologous regulatory element operably linked to a toxin gene of an endogenous toxic-antitoxic system can be any prokaryotic microorganism. As used herein, the term "prokaryotic microorganism" refers to a group of microorganisms that usually lack a cell nucleus or any other membrane-bound organelles. In some embodiments, the prokaryotic microorganisms can include, without limitation, a *eubacterium*, archaebacterium, green nonsulfur bacterium, or purple nonsulfur bacterium or cyanobacterium. According to some embodiments of the present invention, the host microorganism can be a photosynthetic microorganism. In further embodiments, the microorganism can include, but is not limited to, the following genera of cyanobacteria: *Acaryochloris, Agmenellum, Anabaena, Anabaenopsis, Anacystis, Aphanizomenon, Arthrospira, Asterocapsa, Borzia, Calothrix, Chamaesiphon, Chroococcus, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospir-*

*ulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema,* and *Xenococcus.*

A number of cyanobacterial species are known and have been manipulated using molecular biological techniques, including the unicellular cyanobacteria *Synechocystis* sp. PCC6803 and Synechococcus elongates PCC7942, whose genomes have been completely sequenced.

Methods of Controlling the Survival of a Microorganism

The invention can include, in further aspects, a method of controlling the growth of a prokaryotic microorganism, by performing the steps of introducing into the prokaryotic microorganism an exogenous nucleic acid molecule that encodes a Type II toxin, in which the toxin gene can be operably linked to a heterologous promoter, and culturing the microorganism under conditions in which the heterologous promoter is not induced, where exposure of the microorganism to conditions under which the promoter is induced can result in decreased viability and/or impaired growth of the microorganism. The toxin gene can be sequence-modified to render the toxin RNA transcript insensitive to the encoded toxin endonuclease activity. The microorganism can be, for example, a eukaryote or prokaryote and can be a photosynthetic microorganism.

Where the microorganism is a prokaryotic microorganism, the prokaryotic microorganism in preferred embodiments of the methods can include an endogenous gene that encodes an antitoxin cognate to the toxin encoded by the introduced exogenous gene. In these methods, the prokaryotic microorganism can be cultured under permissible conditions in which the microorganism can grow, whereas, when one or more growth conditions is altered, for example, by escape of the microorganism into the environment, expression of the toxin from the heterologous promoter can be induced, and growth/viability of the microorganism can be impaired/reduced. In some preferred embodiments, the prokaryotic host is a cyanobacterium, and expression of the toxin gene regulated by a heterologous promoter can impair photosynthesis. In this way, growth of the microorganism can be restricted to particular growth conditions that may include, as nonlimiting examples, the presence of a particular compound in the media, the absence of a particular compound from the media, a range of temperature, pH, or salinity, a degree of light intensity and/or duration, or a combination thereof.

The present invention can also relate to a method of controlling the growth of a prokaryotic microorganism that comprises an endogenous TAS, by introducing an antisense construct into the prokaryotic microorganism, in which the antisense construct can include a sequence complementary to at least a portion of the noncoding strand of an antitoxin gene of the endogenous TAS, and expression of the antitoxin antisense construct can be regulated by one or more compounds and/or environmental conditions, such that the prokaryotic microorganism can have reduced viability and/or impaired growth when the culture/environmental conditions can promote expression of the antitoxin gene antisense construct. Optionally but preferably, the heterologous promoter can be regulated by a compound that may be present in (or absent from) the cell culture or cell environment, and/or by one or more environmental conditions, for example, salinity, pH, temperature, light intensity, and/or light duration.

In embodiments in which expression of the antitoxin antisense construct reduces viability and/or impairs growth of the engineered microorganism, expression of the antitoxin antisense construct can result in downregulation of the antitoxin gene, where downregulation of the antitoxin gene can result in increased expression and/or activity of the corresponding (cognate) toxin. The term "downregulation," as it refers to genes inhibited by the subject antisense method, refers to a diminishment in the level of expression of a gene(s) in the presence of one or more antisense construct(s), when compared to the level in the absence of such antisense RNA construct(s). The term "downregulation" is used herein to indicate that the target gene expression is lowered by 1-100%. For example, the expression may be reduced by at least about 10%, at least about 20%, at least about 30%, at least about 40%, at least about 50%, at least about 60%, at least about 70%, at least about 80%, at least about 90%, at least about 95%, or at least about 99%.

The present invention can also relate to a method of controlling the growth and/or survival of a prokaryotic microorganism that includes an endogenous Type II TAS, in which at least one heterologous regulatory element can be operably linked to the toxin gene of the endogenous TAS. In particular embodiments, the heterologous regulatory element can be inserted into the genome of the prokaryotic microorganism upstream of the toxin gene of the operon. Further, the heterologous regulatory element may include a promoter that directs expression of the toxin gene. Additionally, the heterologous regulatory element may in some embodiments include a transcriptional terminator upstream of the promoter. In particular embodiments, insertion of a heterologous regulatory element can be by homologous recombination into the host genome. The methods can comprise a step of introducing at least one heterologous regulatory element into the genome of a prokaryotic microorganism, such that at least one of the heterologous regulatory elements can be operably linked to a toxin gene of a TAS system/operon in the prokaryotic microorganism. In certain of these embodiments, expression of the antitoxin antisense construct can be regulated by one or more compounds and/or environmental conditions, such that the prokaryotic microorganism can have reduced viability and/or impaired growth when the culture or environmental conditions promote expression of the toxin gene regulated by the heterologous regulatory element. Optionally but preferably, the heterologous regulatory element, which can be or include a promoter, can be regulated by a compound that may be present in the cell culture or cell environment, and/or by an environmental conditions, such as, for example, salinity, pH, temperature, light intensity, and/or light duration. Preferably, expression of the toxin gene can inhibit the growth and/or impair the viability of the organism. In some preferred embodiments, the prokaryotic host is a cyanobacterium, and expression of the toxin gene regulated by a heterologous promoter can impair photosynthesis.

In some embodiments of the methods, the microorganism can include more than one engineered TAS, as described hereinabove, that is, more than one of any of: a) an exogenous gene encoding a (Type II) toxin operably linked to a heterologous promoter, which in some particular embodiments can be a toxin gene that has been codon-optimized for toxin resistance, b) an antitoxin antisense construct, and c) an endogenous TAS system/operon engineered to include a heterologous promoter operably linked to the toxin gene of the TAS system/operon. A prokaryotic microorganism can be engineered to include any combination of a), b), and/or c). In these embodiments, the prokaryotic host strain can preferably be cultured under contained conditions, in which none of the engineered constructs are expressed.

In these embodiments, the engineered constructs can optionally be regulated by different promoters responsive to different compounds and/or different conditions. For example, an exogenous toxin gene can be operably linked to a promoter that responds to high light intensity, whereas an exogenous construct that includes an antitoxin antisense sequence can be responsive to low ammonium levels. A heterologous regulatory element operably linked to a toxin gene of an endogenous TAS system/operon can, as an illustrative example, be response to a compound in the culture medium, for example, nickel. These illustrations are meant to be exemplary and not limiting. Where the organism finds itself outside the confined growth area, one, two, or more toxin systems may be activated by induction of a promoter operably linked to a toxin gene and/or an antitoxin antisense construct.

In these methods, the engineered prokaryotic microorganism can be cultured under growth-permissible conditions in which its growth is not impaired by the activity of a toxin, whereas when one or more growth conditions is altered, for example by escape of the microorganism into an external environment, growth of the microorganism can be impaired by the activity of a toxin. In this way, growth of the microorganism can be restricted to particular growth conditions that may include, as nonlimiting examples, the presence of a particular compound from the media, the absence of a particular compound from the media, temperature, pH, light intensity, and/or light duration.

In some embodiments, the methods provided herein include controlling the growth and/or survival of a photosynthetic prokaryotic microorganism, such as a cyanobacterium. Additionally, the prokaryotic photosynthetic microorganism can exhibit impaired photosynthesis and/or chlorosis when the microorganism is exposed to conditions under which expression at least one of the one or more exogenous (Type II) toxin genes is induced or derepressed.

In the methods provided herein, expression of a toxin gene and/or expression of an antitoxin antisense sequence can result in growth inhibition and/or impaired viability of the engineered prokaryotic microorganism. In some preferred embodiments, the prokaryotic host is a photosynthetic microorganism, such as a cyanobacterium, and expression of a toxin gene and/or antitoxin antisense construct regulated by a heterologous promoter (including expression by means of a heterologous regulatory element in an engineered TAS operon) can result in chlorosis and/or impaired photosynthesis in the engineered photosynthetic prokaryote.

Impaired photosynthesis can be assessed by various methods, including, without limitation, oxygen evolution, CO2 fixation, and/or fluorescence measurements. For example, fluorescence measurements can provide a ratio of variable to maximal fluorescence ("Fv/Fm") that can be used to assess photosynthetic health or impairment, where a reduction in Fv/Fm with respect to a control cell or culture can be indicative of photosynthetic impairment.

A photosynthetic prokaryote used in the methods of the invention can be a cyanobacterium, and can be, for example, an *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechocystis, Tolypothrix, Trichodesmium, Tychonema*, or *Xenococcus* species.

Another aspect of the invention includes methods for producing a product in a prokaryotic microorganism, in which the production microorganism is genetically engineered for biocontainment, e.g., for growth restricted to a contained and/or proscribed culture environment. In these methods, the culture can be provided with nutrients for growth and/or for production of a product, such as one or more biomolecules, and the culture and environmental conditions can be permissive for growth of the organism. The engineered microorganism can include one or more exogenous nucleic acid molecules that encode one or more polypeptides for the making of a product, such as a biomolecule. In some embodiments, the prokaryotic microorganism can be engineered to produce a lipid, hydrocarbon, fatty acid, and/or fatty acid derivative, as disclosed, for example, in International Publication Nos. WO 2007/136762, WO 2008/119082, WO 2009/009391, WO 2009/076559, WO 2010/044960, WO 2010/118410, WO 2010/126891, WO 2011/008535, and WO 2011/019858.

The invention can further include methods for producing a product in a transgenic microorganism including a biocontainment system as described herein, in which the methods include culturing a transgenic microorganism containing at least one exogenous nucleic acid molecule encoding a Type II toxin gene operably linked to a heterologous promoter, at least one antitoxin antisense construct, and/or at least one engineered TAS system/operon, under conditions in which the transgenic microorganism produces at least one product, and isolating the product from the microorganism or the culture medium.

The microorganism having a Type II toxin-based biological control system may be unaffected or minimally affected by the presence of the toxin-based biological control system under containment culture and environmental conditions, but can exhibit impaired growth and/or health under noncontainment culture and/or environmental conditions. In some preferred embodiments, the transgenic microorganism having a toxin-based biological control system does not divide and/or is not viable under noncontainment culture and/or environmental conditions. In some preferred embodiments, the host microorganism used for synthesizing a product is a eukaryotic microalga or a cyanobacterium, and can exhibit chlorosis and/or impaired photosynthetic function under noncontainment culture and/or environmental conditions.

Optionally, the methods can include providing a compound in the culture medium, in which the presence of the compound can prevent, inhibit, and/or reduce the expression of the toxin gene and/or of an antitoxin antisense construct. Alternately or in addition, the methods can optionally include not providing a compound in the medium, in which the absence of the compound can prevent, inhibit, and/or reduce the expression of the toxin gene and/or of an antitoxin antisense construct. Further additionally or alternately, the methods can optionally include providing culture conditions under which the expression of the toxin gene and/or of an antitoxin antisense construct can be reduced and/or eliminated. In such embodiments, which can be used in combination, particularly but not exclusively where the transgenic microorganism includes more than one toxin construct and/or more than one antitoxin antisense construct, a microorganism growing under contained culture conditions can grow and/or produce a product, but under non-controlled conditions, one or more toxin genes and/or one or more antitoxin antisense constructs would likely be expressed, and the cells would thus likely die.

In accordance with the present invention, the culture methods described further herein can include inducing transcription from the heterologous promoter to express the toxin gene and/or inducing transcription of the nucleic acid sequence encoding an antisense oligonucleotide that can hybridize with at least a portion of an endogenous antitoxin gene, under conditions where proliferation of the microorganism can be undesirable. Inducing transcription can include adding a nutrient/compound to the culture medium, removing one or more components from the culture medium, increasing or decreasing light and/or temperature, and/or other manipulations that can promote expression of the gene of interest. Such manipulations can largely depend on the nature of the heterologous promoter as described previously.

Culturing refers to the intentional fostering of growth (e.g., increases in cell size, cellular contents, and/or cellular activity) and/or propagation (e.g., increases in cell numbers such as via mitosis) of one or more cellular microorganisms by use of selected and/or controlled conditions. The combination of both growth and propagation may be termed proliferation. Nonlimiting examples of selected and/or controlled conditions can include the use of a defined medium (with known characteristics such as pH, ionic strength, and/or carbon source), specified temperature, oxygen tension, carbon dioxide levels, growth in a bioreactor, or the like, or combinations thereof. In some embodiments, the microorganism can be grown heterotrophically, using a reduced carbon source, or mixotrophically, using both light and a reduced carbon source. Additionally or alternately, the microorganism can be cultured phototrophically. When growing phototrophically, the microorganism can advantageously use light as an energy source. An inorganic carbon source, such as $CO_2$ or bicarbonate, can be used for synthesis of biomolecules by the microorganism. "Inorganic carbon", as used herein, includes carbon-containing compounds or molecules that cannot be used as a sustainable energy source by an organism. Typically "inorganic carbon" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by organisms. If an organic carbon molecule or compound is provided in the culture medium of a microorganism grown phototrophically, it generally cannot be taken up and/or metabolized by the cell for energy and/or typically is not present in an amount sufficient to provide sustainable energy for the growth of the cell culture.

Microorganisms that can be useful in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of products of interest can vary. In some cases, certain strains of microorganisms may be unable to grow in a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of strains of microorganisms. For example, various fresh water and salt water media can include those described in Barsanti (2005) Algae: Anatomy, Biochemistry & Biotechnology, CRC Press for media and methods for culturing algae. Algal media recipes can also be found at the websites of various algal culture collections, including, as nonlimiting examples, the UTEX Culture Collection of Algae (sbs.utexas.edu/utex/media.aspx); Culture Collection of Algae and Protozoa (ccap.ac.uk/media/pdfrecipes); and Katedra Botaniky (botany.natur.cuni.cz/algo/caup-media.html).

In some embodiments of the present invention, the recombinant microorganisms can be cultured in a bioreactor. "Bioreactor" refers to an enclosure or partial enclosure in which cells are cultured, optionally in suspension and, when suspended, preferably in an aqueous liquid. The bioreactor can be used to culture (microalgal) cells through the various phases of their physiological cycle. Bioreactors can offer many advantages for use in heterotrophic growth and propagation methods. To produce biomass for use in food, microorganisms are preferably fermented in large quantities in liquid, such as in suspension cultures as an example. Bioreactors such as steel fermentors can accommodate very large culture volumes (40,000+ liter capacity bioreactors can be used in various embodiments of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen, and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

Cells can additionally or alternately be cultured in a bioreactor equipped with an artificial light source, i.e., a "photobioreactor", which can have one or more walls transparent enough to light, including sunlight, to enable, facilitate, and/or maintain acceptable microorganism growth.

Further additionally or alternatively, genetically engineered photosynthetic microorganisms may be grown in ponds, canals, trenches, raceways, channels, or the like, or combinations thereof. As with standard bioreactors, a source of inorganic carbon (such as, but not limited to, $CO_2$, bicarbonate, carbonate salts, and the like), including, but not limited to, air, $CO_2$-enriched air, flue gas, or the like, or combinations thereof, can be supplied to the culture. When supplying flue gas and/or other sources of inorganic that may contain CO in addition to $CO_2$, it may be necessary to pre-treat such sources such that the CO level introduced into the (photo)bioreactor do not constitute a dangerous and/or lethal dose vis-á-vis the growth and/or survival of the microorganisms.

The invention can also encompass methods of introducing a toxin gene into a microorganism by transforming a vector comprising a toxin gene and a corresponding (cognate) antitoxin gene into the microorganism, where the toxin gene can be in an integrating portion of the vector, and the antitoxin gene can be in a non-integrating portion of the vector. In particular, these toxin and antitoxin genes in some embodiments can be derived from a cyanobacterial species as described herein. The vector can further include a regulatable promoter that can control the toxin gene and/or a constitutive promoter that can control the antitoxin gene. As used herein, a "constitutive promoter" refers to an unregulated promoter that can allow continuous transcription of its (cognate) gene.

It will be understood that in this context the term "functional equivalent" can include variants and/or derivatives of any of the toxins/antitoxins described herein, the sequences of which may have been modified by substitution, deletion, and/or addition of one or more amino acids, and the gene product of which may have retained at least part of the function of the gene product of the non-modified sequence.

Production of Lipids and Hydrocarbons

A recombinant microorganism including an engineered toxin, antitoxin, or toxin-antitoxin system/operon as disclosed herein can be engineered for the synthesis of lipids and/or hydrocarbons, for example, for production of biofuels. The engineered microorganism can be, in particular embodiments, a photosynthetic microorganism, such as a cyanobacterial species. In some embodiments, a host microorganism having an engineered biocontainment system based on a toxin-antitoxin system can include an exogenous thioesterase and/or lipase gene for the production of free fatty acids and/or fatty acid derivatives (such as, for example, a fatty alcohol, a wax ester, an alkane, and/or an alkene). When one or more fatty acids are produced (whether in the form of acids or acid salts), at least some (e.g., a majority, or more than 50 wt %, and in some preferred embodiments at least 95 wt % or at least 99 wt %) of the fatty acids can advantageously have an acyl chain length from 8 to 24 carbons.

An exogenous thioesterase expressed in the host microorganism can be, for example, an acyl-ACP thioesterase (such as, for example, any disclosed in U.S. Pat. Nos. 5,455,167, 5,654,495, or 5,455,167, or U.S. Patent Application Publication Nos. 20090298143 or 20110020883, each of which is incorporated herein by reference in its entirety), an acyl-CoA thioesterase (e.g., a gene encoding the TesA or TesB thioesterase of *E. coli*, or a variant thereof, for example, an acyl-CoA thioesterase such as, but not limited to, a variant as disclosed in PCT Publication No. WO 2010/075483, incorporated by reference herein in its entirety), and/or a hydroxylbenzoyl thioesterase.

Additionally or alternately to providing an expression system for one or more appropriate recombinant genes, such as thioesterase and/or lipase genes, further modifications may be made in the microorganism that has been engineered for biocontainment as described herein. For example, in some embodiments, a genetically engineered microorganism containing a recombinant toxin gene, antitoxin gene, and/or antitoxin antisense construct, and/or an endogenous toxin-antitoxin system/operon engineered to include at least one operably linked heterologous promoter, can include one or more nucleic acid molecules encoding an acyl-CoA reductase, carboxylic acid reductase, and/or acyl-ACP reductase. Further additionally or alternately, the genetically engineered photosynthetic microorganism can produce a fatty alcohol and can include at least one nucleic acid molecule encoding an acyl-CoA reductase, carboxylic acid reductase, and/or acyl-ACP reductase, and/or a fatty aldehyde reductase. Still further additionally or alternately, the genetically engineered photosynthetic microorganism of the described invention can produce a wax ester and can include one or more nucleic acid molecules encoding an acyl-CoA reductase, carboxylic acid reductase, and/or acyl-ACP reductase, and a wax synthase. Wax esters include an A chain and a B (acyl) chain linked through an ester bond, one or both of which can be derived from a fatty acid and/or fatty acid derivative generated by a transcription factor domain protein. Wax esters produced by a transgenic microorganism including a nucleic acid molecule encoding a transcription factor domain protein can therefore have A chain lengths, for example, from 8 to 24 carbons and B chain lengths, for example, from 8 to 24 carbons. Additionally or alternately, the wax esters synthesized by the photosynthetic host microorganism can have A+B chain lengths from 16 to 48 carbons, for example, from 16 to 36 carbons, from 16 to 32 carbons, or from 24 to 32 carbons.

In further additional or alternate embodiments, the photosynthetic microorganism that includes an engineered toxin-antitoxin system/operon as disclosed herein can produce an alkane and/or alkene and can include at least one nucleic acid molecule encoding a fatty acid decarboxylase and/or an exogenous fatty aldehyde decarbonylase, optionally also including at least one nucleic acid molecule encoding an acyl-CoA reductase, carboxylic acid reductase, and/or acyl-ACP reductase. Alkanes and alkenes produced by a photosynthetic microorganism including a nucleic acid molecule encoding a transcription factor domain protein can have chain lengths of 7, 9, 11, 13, 15, 17, 19, 21, and/or 23 carbons, e.g., chain lengths of 7, 9, 11, 13, 15, and/or 17 carbons, chain lengths of 7, 9, 11, 13, and/or 15 carbons, or chain lengths of 11, 13, and/or 15 carbons.

Additionally, a genetically engineered microorganism that produces a fatty alcohol, fatty aldehyde, wax ester, alkane, and/or alkene may optionally include a nucleic acid molecule encoding an acyl-CoA synthetase.

A genetically engineered microorganism that includes at least a toxin gene for biocontainment can also be a microorganism, such as but not limited to a microalga, engineered for lipid biosynthesis, and/or can include, for example, an exogenous gene encoding an acetyl-CoA carboxylase, a malonyl type 1 fatty acid synthase, a type 2 fatty acid synthase subunit, a beta ketoacyl-ACP synthase, a malonyl-CoA-malonyl-ACP acyltransferase, an acyl-ACP thioesterase, an acyl-CoA thioesterase, a 4-hydroxybenzoyl thioesterase, an alcohol forming acyl reductase, a wax synthase, an aldehyde decarbonylase, a fatty acid decarboxylase, a lipase, a glyceraldehyde 3 phosphate dehydrogenase, an acyl-CoA synthetase, a phospholipid diacylglycerol acyltransferase, a glycerol 3 phosphate acyltransferase, a lysophosphatidic acid acyltransferase, a phosphatidic acid phosphatase, a diacyl glycerol acyltransferase, or a dehydrogenase. For example, the microorganism can be engineered to produce triglycerides.

Additionally or alternately, the present invention can include one or more of the following embodiments.

Embodiment 1. A recombinant microorganism that includes an exogenous Type II toxin gene that encodes an endoribonuclease operably linked to a heterologous promoter, wherein the sequence of the toxin gene has been modified to eliminate target sites of the encoded endoribonuclease in the Type II toxin transcript RNA.

Embodiment 2. The recombinant microorganism of embodiment 1, wherein the heterologous promoter is regulatable, preferably by one or more of light, temperature, pH, or the presence or absence of one or more nutrients or compounds in the culture medium or environment of the microorganism, optionally wherein the heterologous promoter is a synthetic promoter.

Embodiment 3. The recombinant microorganism of embodiment 1, wherein the heterologous promoter is regulated by the absence or presence of a nutrient in the medium, optionally wherein the nutrient is nitrogen, phosphorus, sulfur, iron, copper, or $CO_2$.

Embodiment 4. The recombinant microorganism of any of the previous embodiments wherein the recombinant microorganism is a photosynthetic microorganism, for example, a eukaryotic microalgal, optionally of a *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella,*

*Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachorella, Tetraselmis, Thalassiosira, Viridiella,* or *Volvox* species, or a cyanobacterium, optionally of a *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechocystis, Tolypothrix, Trichodesmium, Tychonema,* or *Xenococcus* species.

Embodiment 5. The recombinant microorganism of any of the previous embodiments wherein the recombinant microorganism further includes an exogenous or endogenous antitoxin gene operably linked to a heterologous promoter, optionally wherein the heterologous promoter operably linked to the antitoxin gene is regulated differently from the heterologous promoter operably linked to the toxin gene, optionally wherein the heterologous promoter operably linked to the antitoxin gene is active under nutrient replete conditions and the heterologous promoter operably linked to the toxin gene is active under depletion of one or more nutrients such as nitrogen, phosphorus, sulfur, iron, copper, or $CO_2$.

Embodiment 6. The recombinant microorganism of embodiment 4 or 5 wherein the recombinant microorganism is a eukaryotic alga and the heterologous promoter operably linked to the toxin gene is a nucleic acid sequence comprising at least 100 contiguous base pairs of SEQ ID NO:56, SEQ ID NO:57, SEQ ID NO:58, SEQ ID NO:59, SEQ ID NO:60, SEQ ID NO:61, or SEQ ID NO:65.

Embodiment 7. The recombinant microorganism of embodiment 6 wherein the recombinant microorganism is a eukaryotic alga and the heterologous promoter operably linked to the toxin gene is a constitutive promoter and/or a nucleic acid sequence comprising at least 100 contiguous base pairs of SEQ ID NO:62, SEQ ID NO:63, or SEQ ID NO:64.

Embodiment 8. An isolated or recombinant nucleic acid molecule comprising a sequence comprising at least 100 contiguous base pairs of SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64 or SEQ ID NO:65, wherein the nucleic acid molecule has promoter activity, optionally wherein the nucleic acid molecule has promoter activity that is regulated at least in part by the level of a nutrient, preferably nitrogen or phosphate.

Embodiment 9. The recombinant microorganism of any of the previous embodiments wherein the recombinant microorganism includes two or more exogenous toxin genes encoding different Type II toxins operably linked to a heterologous promoter, optionally wherein the toxin genes are operably linked to promoters regulated by the presence or absence of different nutrients or compounds.

Embodiment 10. The recombinant microorganism embodiment 9, wherein the recombinant microorganism includes at least one exogenous Type II toxin gene engineered to be insensitive to at least two of the toxins encoded by the two or more exogenous toxin genes.

Embodiment 11. A prokaryotic microorganism comprising an endogenous toxin-antitoxin system, e.g., a Type II TAS, wherein at least one heterologous regulatory element is operably linked to a toxin gene of the endogenous toxin-antitoxin system.

Embodiment 12. A recombinant prokaryotic microorganism genetically engineered for biocontainment, wherein the prokaryotic microorganism comprises an endogenous Type II toxin-antitoxin system operon operably linked to a heterologous regulatable promoter.

Embodiment 13. A method of controlling the growth and/or survival of a prokaryotic microorganism, the method comprising steps of inserting a heterologous promoter upstream of either a) an antitoxin-toxin operon, or b) a toxin gene of an endogenous toxin-antitoxin system/operon of the microorganism, and inducing transcription from the heterologous promoter or providing conditions in which transcription from the heterologous promoter is activated, derepressed, and/or induced, to express either the toxin-antitoxin operon or the toxin gene, wherein expression of the antitoxin-toxin operon or the toxin gene results in impaired growth or survival (such as cell death) of the prokaryotic microorganism.

Embodiment 14. A recombinant prokaryotic microorganism genetically engineered for biocontainment, wherein the prokaryotic microorganism comprises an exogenous Type II toxin gene (that can be heterologous or homologous to the prokaryotic microorganism) operably linked to a regulatable promoter, e.g., that directs expression of the toxin gene, wherein optionally: (a) the exogenous Type II toxin gene encodes an endoribonuclease and the sequence of the exogenous Type II toxin gene is sequence-optimized to exclude one or more target sequences recognized by the endoribonuclease; or (b) the prokaryotic microorganism comprises a toxin-antitoxin system (e.g., an endogenous TAS) that encodes an antitoxin cognate to a toxin resulting from the expression of the Type II toxin gene.

Embodiment 15. A recombinant prokaryotic microorganism genetically engineered for biocontainment, wherein the prokaryotic microorganism comprises an endogenous Type II toxin-antitoxin system and further comprises an exogenous nucleic acid molecule comprising a sequence encoding an antitoxin cognate to the toxin encoded by the endogenous TAS, wherein the sequence encoding the antitoxin is operably linked to a regulatable promoter.

Embodiment 16. A recombinant prokaryotic microorganism comprising an antitoxin antisense construct, wherein the antitoxin antisense construct comprises an antisense nucleotide sequence that hybridizes with at least one antitoxin gene of the recombinant prokaryotic microorganism, wherein the antisense nucleotide sequence is operably linked to an exogenous promoter, wherein the antisense construct is integrated into the genome of the recombinant prokaryotic organism.

Embodiment 17. A method of controlling the growth and/or survival of a prokaryotic microorganism, the method comprising steps of transforming the prokaryotic microorganism with a) an exogenous toxin gene operably linked to a regulatable promoter; b) an exogenous nucleic acid molecule encoding an antitoxin cognate to a toxin endogenous to the microorganism operably linked to a regulatable promoter; or c) an exogenous nucleic acid molecule encoding an antisense sequence to an antitoxin endogenous to the microorganism operably linked to a regulatable promoter; and inducing transcription from the heterologous promoter or providing conditions in which transcription from the heterologous promoter is activated, derepressed, or induced, to express the antitoxin-toxin operon and/or the toxin gene, wherein expression of the antitoxin-toxin operon and/or the toxin gene results in impaired growth or survival of the prokaryotic microorganism.

Embodiment 18. A vector comprising a promoter sequence operably linked to a nucleic acid sequence encoding a small inhibitory RNA or an antisense oligonucleotide that hybridizes with at least a portion of an antitoxin gene of an endogenous toxin-antitoxin system in a microorganism.

Embodiment 19. A method of introducing a toxin gene into a microorganism, comprising transforming a vector comprising a toxin gene and a cognate antitoxin gene into the microorganism, wherein the toxin gene is in an integrating portion of the vector, and the antitoxin gene is in a non-integrating portion of the vector, and optionally wherein one or more of the following are satisfied: the microorganism is a cyanobacterial species; the toxin and antitoxin genes are derived from a cyanobacterial species; the toxin gene is under control of a regulatable promoter; the antitoxin gene is under control of a constitutive promoter; the toxin gene is a PemK family toxin gene; and the antitoxin gene is a PemI family antitoxin gene.

Embodiment 20. The microorganism, vector, or method according to any one of the previous embodiments, wherein one or more of the following are satisfied: the microorganism or cyanobacterium is a photosynthetic microorganism; the microorganism or cyanobacterium is a species of *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechocystis, Tolypothrix, Trichodesmium, Tychonema,* or *Xenococcus*; the regulatory element or promoter is regulated by the presence or absence of a compound in the cell culture, media, and/or cell environment, such compound optionally including a sugar, an organic acid, a fatty acid, a lipid, a hydrocarbon, phosphate, nitrate, ammonium, a metal, a quorum-sensing compound, a secreted protein and/or peptide, or any combination thereof; the regulatory element or promoter is responsive to light, temperature, pH, metabolic state, or a combination thereof; and the regulatory element or promoter is selected from the group consisting of trp promoter, arabinose (e.g., L-arabinose) inducible promoter, IPTG (isopropyl-β-D-thiogalactopyranoside) inducible promoter, lac promoter, tac promoter, trc promoter, trcE promoter, trcY promoter, secA promoter, glnA promoter, psbA promoter, nar promoter, ntc promoter, nir promoter, nr promoter, pho promoter, pst promoter, nrs promoter, ara promoter, rha promoter, tet promoter, cys promoter, metallothionien promoter, ftf promoter, hear shock promoter, cold-inducible promoter, viral promoter, hin promotoer, cin promoter, gin promoter, fimA promoter, a variant or hybrid thereof, and a combination thereof.

Embodiment 21. The microorganism, vector, or method according to any one of the previous embodiments, wherein one or more of the following is satisfied: the antitoxin gene encodes a Type II antitoxin; the antitoxin gene encodes an antitoxin of CcdA antitoxin family, CcdB antitoxin family, RelB antitoxin family, MazE antitoxin family, ParD antitoxin family, PIN antitoxin family, MNT antitoxin family, RHH antitoxin family, ArsR antitoxin family, HEPN antitoxin family, Phd antitoxin family, VapB antitoxin family, epsilon antitoxin family, zeta antitoxin family, HipB antitoxin family, or HigA antitoxin family; the antitoxin gene is selected from the group consisting of cyanobacterial homologs of axe, phd, mazE, hicB, vapB, pemI, relB, parD, kiS, ccdA, yafN, stbD, yoeM, PIN, and combinations thereof; the toxin gene encodes a Type II toxin; the toxin gene encodes a toxin of CcdB toxin family, RelE toxin family, MazF toxin family, ParE toxin family, PIN toxin family, AhaI toxin family, MNT toxin family, Doc toxin family, VapC toxin family, zeta toxin family, HipA toxin family, or HigB toxin family; the toxin gene is selected from the group consisting of homologs of txe, doc, mazF, hicA, vapC, pemK, ccdB, relE, parE, PIN, kiD, yafQ, rv3182, stbE, yoeB, Z5902, and combinations thereof; and the toxin-antitoxin system or operon, if present, is a Type II toxin-antitoxin system or operon.

Embodiment 22. The microorganism or method according to any one of embodiments 11, 13-14, and 20-21, wherein one or more of the following are satisfied: the regulatory element or promoter is inserted into or is present in the genome of the prokaryotic microorganism upstream of the toxin gene; the regulatory element or the microorganism or cyanobacterium comprises a transcriptional terminator located or inserted upstream of the promoter; a second promoter is present downstream of the antitoxin gene that directs expression of a nucleic acid sequence encoding an antisense oligonucleotide that hybridizes with at least a portion of the antitoxin gene of the endogenous toxin-antitoxin system, wherein the second promoter downstream of the antitoxin gene is optionally regulated by the same compound as the promoter that directs expression of the toxin gene or is optionally regulated by a different compound as the promoter that directs expression of the toxin gene; and the promoter is a bidirectional promoter that directs expression of the toxin gene and expression of a nucleic acid sequence encoding an antisense oligonucleotide that hybridizes with a portion of the antitoxin gene of the toxin-antitoxin system.

Embodiment 23. The microorganism, vector, or method according to any one of embodiments 14-17 and 19-21, wherein one or more of the following are satisfied: the microorganism comprises a second promoter operably linked to, e.g., upstream of, a toxin gene (where applicable, of the toxin-antitoxin system and/or operon), which second promoter is optionally regulated by the same compound as the first promoter or is optionally regulated by a different compound than the first promoter; and the first promoter is a bidirectional promoter that directs expression of the antisense oligonucleotide and a toxin gene of a/the toxin-antitoxin system.

Embodiment 24. The microorganism or method of any one of embodiments 11-17 and 19-22, wherein the microorganism comprises two or more toxin-antitoxin systems and/or operons (at least one of which, or two or more of which, can be endogenous) where at least two of the toxin- antitoxin systems optionally include a heterologous promoter operably linked to toxin genes of the toxin-antitoxin systems and/or operons, and the at least two of the toxin-antitoxin systems and/or operons comprising the same or different promoters operably linked to the toxin genes of the at least two toxin-antitoxin systems and/or operons.

Embodiment 25. The microorganism, cyanobacterium, vector, or method according to any one of embodiments 11-17 and 19-24, wherein expression of the toxin gene (and/or a toxin gene of the toxin-antitoxin system) results in impaired photosynthetic function of the microorganism or cyanobacterium.

Embodiment 26. The microorganism according to any one of embodiments 14, 17, 19-21, and 23-25, wherein the microorganism either comprises or does not comprise an endogenous gene encoding an antitoxin cognate to a toxin encoded by the exogenous toxin gene, and wherein the microorganism optionally does not comprise an exogenous gene encoding an antitoxin cognate to a toxin encoded by the exogenous toxin gene.

Embodiment 27. The microorganism, vector, or method according to any one of the previous embodiments, wherein the toxin and/or antitoxin gene is derived from an *Acaryochloris*, *Anabaena*, *Chlorobium*, *Cyanothece*, *Gloeobacter*, *Microcystis*, *Nostoc*, *Prochlorococcus*, *Rhodopseudomonas*, *Synechococcus*, *Synechocystis*, *Thermosynochocystis*, or *Trichodesmium* species.

Without further description, it is believed that one of ordinary skill in the art can, using the preceding description and the following illustrative examples, make and utilize the present invention and practice the claimed methods. The following working examples, therefore, specifically point out representative embodiments of the present invention, some preferred, and are not to be construed as limiting in any way the remainder of the disclosure.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and/or alterations can be employed without departing from the scope of the presently disclosed subject matter.

Example 1

Expression of Antitoxin Genes in Prokaryotic Microorganism

TAS operons were identified in cyanobacterial species by identifying gene pairs in which two genes were oriented in tandem and in very close proximity, in which at least one of the genes was annotated as a toxin or antitoxin ("guilt by association"). For example, the open reading frame annotated as the vapC toxin in the genome of Anabaena PCC 7120 is found at the same locus as another ORF immediately upstream and overlapping the vapC start codon by 8 base pairs (operon configuration diagram available at genome.kazusa.or.jp/cyanobase). This was inferred to be a TAS operon because the association of genes was close and the small ORF size (300-400 bp) correlates with previously characterized toxins and antitoxins.

In addition to identification of TAS components within the Anabaena genome, analyses were carried out on the genome of the cyanobacterium Synechococcus PCC 7942. BLAST searches identified a putative TAS operon having axe/txe components. The txe ORF (Synpcc_7942_1207) is annotated as such, whereas the upstream gene (Synpcc_7942_1208) is putatively annotated as a "prevent-host-death protein". Sequence similarities to *E. coli* and cyanobacterial axe proteins suggest this ORF is indeed the axe antitoxin. The Synechococcus PCC 7942 axe gene is found in an axe/txe operon, with the predicted axe gene overlapping the txe start codon by 7 base pairs. As seen in other TAS operons, the small size of the two ORFS (511 bp) correlates with the expected size of a TAS operon. (This region of the genome also includes at least one additional antitoxin-toxin operon, including Synpcc_7942_1204 (annotated as "prevent-host-death protein") and Synpcc_7942_1203 (annotated as "hypothetical protein") that belong to the VapC, PIN toxin family.)

These genomic sequences were used to design primers to clone the operons, in addition to other toxin and antitoxin genes of three predicted TAS operons from Synechoccocus PCC 7942 and Anabaena PCC 7120. Upstream forward (UF) and internal reverse (IR) primers were designed to clone these cyanobacterial toxin and antitoxin genes (Table 2)

TABLE 2

Primers used to clone TAS components from *Synechococcus* PCC 7942 and *Anabaena* PCC 7120

| | |
|---|---|
| UF primer PCC7942-axe | atgaaagttgtttccttcagtgacgcca (SEQ ID NO: 25) |
| IR primer PCC7942-axe | ttacgcatctaatagatttcgctcgactg (SEQ ID NO: 26) |
| UF primer PCC7942-txe | atgcgtaagctggcttggacaaac (SEQ ID NO: 27) |
| IR primer PCC7942-txe | ttaatcgctgtagtggtagcgaca (SEQ ID NO: 28) |
| UF primer PCC7942-phd | gtgcgggtgaacctgaattttgaaag (SEQ ID NO: 29) |
| IR primer PCC7942-phd | tcatgcccgccgcccagtatca (SEQ ID NO: 30) |
| UF primer PCC7942-doc | atgagctttgtgttggatgtctcactg (SEQ ID NO: 31) |
| IR primer PCC7942-doc | ttaggtcggcagtaacgtaactcc (SEQ ID NO: 32) |
| UF primer PCC7120-mazE | atgacaacagttgtagctaaatggggaaac (SEQ ID NO: 33) |
| IR primer PCC7120-mazE | ctaccaagcttcattccccacag (SEQ ID NO: 34) |
| UF primer PCC7120-mazF | gtgaagccgccttactttcccaata (SEQ ID NO: 35) |
| IR primer PCC7120-mazF | ctataaaattaatgtttcgagttttgcttgtacttct (SEQ ID NO: 36) |

DNA fragments corresponding to the antitoxins axe (SEQ ID NO:13; protein sequence SEQ ID NO:14), phd (SEQ ID NO:15; protein sequence SEQ ID NO:16), mazE (SEQ ID NO:17; protein sequence SEQ ID NO:18), hicB (SEQ ID NO:19; protein sequence SEQ ID NO:20), vapB (SEQ ID NO:21; protein sequence SEQ ID NO:22), and pemI (SEQ ID NO:23; protein sequence SEQ ID NO:24) (also referred to as "repressors") were subcloned into the IPTG-inducible pTrc-His vector (Invitrogen, Carlsbad, Calif.) and transformed into TOP10F cells (Invitrogen). Single colonies were used to inoculate liquid LB cultures and grown overnight at 30° C. in the presence of 50 µg/mL carbenicillin. The next morning, the OD600 of the cultures was measured and the cells reinoculated into duplicate cultures (7 total, including pTrc-His vector only cultures). The cultures were grown to an OD600 of 0.3 (roughly 2.5 hours) and IPTG was added to a final concentration of 1 mM. The cultures were allowed to incubate and OD600 measured at one, two, four, and six hours after induction. The results are shown in FIG. 1, which demonstrates that addition of IPTG to cells harboring TAS components did not have a negative impact on cell growth over the time course. The antitoxins could not be detected by polyacrylamide gel analysis and staining at any point in the time course; however, this was likely due to the high turnover of antitoxins when not bound to their cognate toxins, as mediated by the Lon protease. This assumption was supported by RT-PCR data showing transcription of the antitoxin genes in *E. coli*.

Example 2

Inhibition of Cell Growth in *E. coli* by Induced Expression of pemK Endoribonuclease Two *E. coli* clones carrying the toxin gene (encoding FLAG-tagged pemK; SEQ ID NO:37) and two clones carrying the antitoxin gene (encoding FLAG-tagged pemI; SEQ ID NO:38), along with a clone with an empty vector control (pBAD vector), were inoculated into 20 mL of LB-Kan (50 ug/mL) and grown overnight at 30° C. The cell line used was TOP10 *E. coli* (Invitrogen; Carlsbad, Calif.). The following day, OD600 measurements of the cultures were recorded and cultures diluted to OD600 of 0.1 in 20 mL of fresh LB-Kan 50 in triplicate (15 tubes total). Arabinose was added to a final volume of 0.2% at time zero. The cultures were incubated at 30° C. with OD600 readings recorded over a 5-hour time period.

Figure 2:
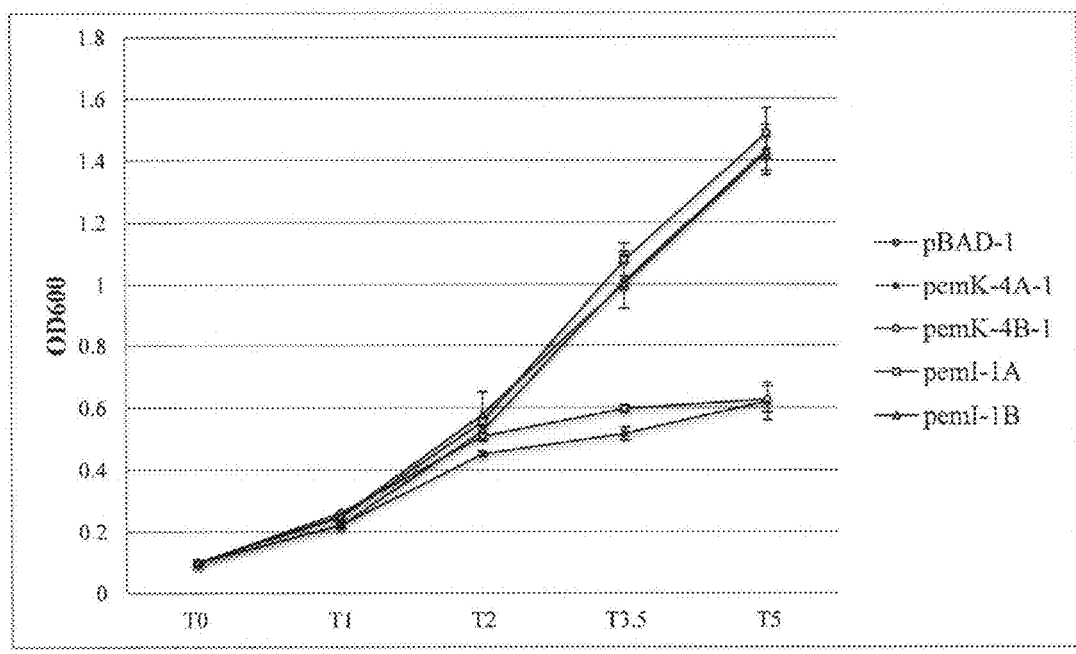
FIG. 2 depicts the time course of *E. coli* culture growth after induction of pemK endoribonuclease gene expression or pemI expression with L-arabinose.

As seen in FIG. 2, arabinose-induced expression of both clones of the pemK toxin caused a defect in bacterial growth beginning at roughly 2-3.5 hrs after addition, whereas the pBAD and pemI clones showed no effects on cell growth. These results suggest that the cDNA of MAE58160 (pemK) is indeed a toxin and antagonizes cell growth, whereas MAE58150 (pemI) does not show any discernable effects on bacterial growth in the course of this assay.

Example 3

Western Blot Analysis of pemIK Protein Expression in TOP10 Cells

During the course of the experiment described above, 1 mL samples of each clone (6 total, including lacZ negative control) were collected at time 0 and 4 hours post-addition of arabinose to verify that the toxin and antitoxin proteins were expressed in the cells. The cells were harvested by centrifugation at 14,000 rpm for 5 minutes. The supernatant was then removed and the cell pellets frozen at −20° C. overnight. The following day, 100 ul of 5% SDS sample buffer was added to the time zero samples, whereas 150 µl of sample buffer was added to the 5 hour samples. The pellets were resuspended by repeated pipetting and then heated for 5 minutes at 95° C. After heating, the samples were allowed to cool to room temperature, then vortexed briskly for 30 seconds to break up genomic DNA. Insolubles were pelleted from samples by centrifugation at 14,000 rpm for 1 min. 5 µl of each sample was loaded on a 4-12% Bis-Tris gradient gel (Invitrogen) and proteins separated by electrophoresis. Proteins were then transferred to PVDF membrane and the membrane blocked with 5% BSA in PBS for 1 hr at room temperature. The blot was then subjected to anti-FLAG primary antibody (Sigma; St. Louis, Mo.) at a dilution of 1:2000 overnight at 4° C. The membrane was washed with PBS for 1 hour (4 washes) the following morning, and then subjected to AP-conjugated anti-mouse secondary antibody solution (Invitrogen) for 1 hr at room temperature. The membrane was again washed for 1 hr total with 1×PBS (4 washes). The membrane was exposed by addition of NBT/BCIP reagent (Invitrogen; Carlsbad, Calif.) for 5 minutes, and then washed repeatedly with water.

No anti-FLAG immunoreactivity was observed at time 0, immediately before the addition of arabinose, whereas after 4 hrs, in both pemI and pemK clones anti-FLAG-reactive bands were seen at approximately the predicted molecular weights for the antitoxin (9 kDa) and toxin (13 kDa). These results support the data that expression of pemK protein was indeed responsible for the growth defect observed, and that while the pemI protein was expressed, did not have deleterious effects on bacterial growth.

Example 4

Expression of the PemK Toxin

DNA Fragments Used in this Study:

A 1.2 kb region of the araC-pBAD transcription factor/promoter sequence (SEQ ID NO:39; renamed "pARA") was cloned by colony PCR from the *E. coli* strain ER2508 (genomic region 70,048 to 71,265). The two RS-1 homology arms (RS-1 "up" (SEQ ID NO:40); and RS-1 "down" (SEQ ID NO:41)) from the *Synechocystis* genome were generated by PCR amplification from the KF01 plasmid. The cDNAs for ccdA (SEQ ID NO:42; protein sequence SEQ ID NO:43) and ccdB (SEQ ID NO:44; protein sequence SEQ ID NO:45) of *E. coli* were generated by PCR amplification of synthetic DNAs (using ultramer and minigene assembly, respectively).

The cDNA for the three cyanobacterial metacaspases were generated by PCR amplification of predicted ORFs from genomic DNA preps from a proprietary *Leptolyngbya* strain ("metacaspase 1"; SEQ ID NO:46; protein SEQ ID NO:47); *Anabaena* sp. ("metacaspase 2"; SEQ ID NO:48; protein SEQ ID NO:49), and *Synechocysits* sp. PCC 6803 ("metacaspase 3"; SEQ ID NO:50; protein SEQ ID NO:51). FLAG-tagged versions of the pemI gene (SEQ ID NO:52), pemK gene (SEQ ID NO:53), and an operon encoding the pemIK antitoxin and toxin genes (SEQ ID NO:54) were generated by PCR amplification from synthetic genes codon-optimized for expression in *Synechocystis* PCC 6803. The cDNAs for the GFP and YFP control ORFs were generated by PCR amplification from TurboGFP and TurboYFP plasmids purchased from Evrogen (Moscow, Russia).

Figure 3:
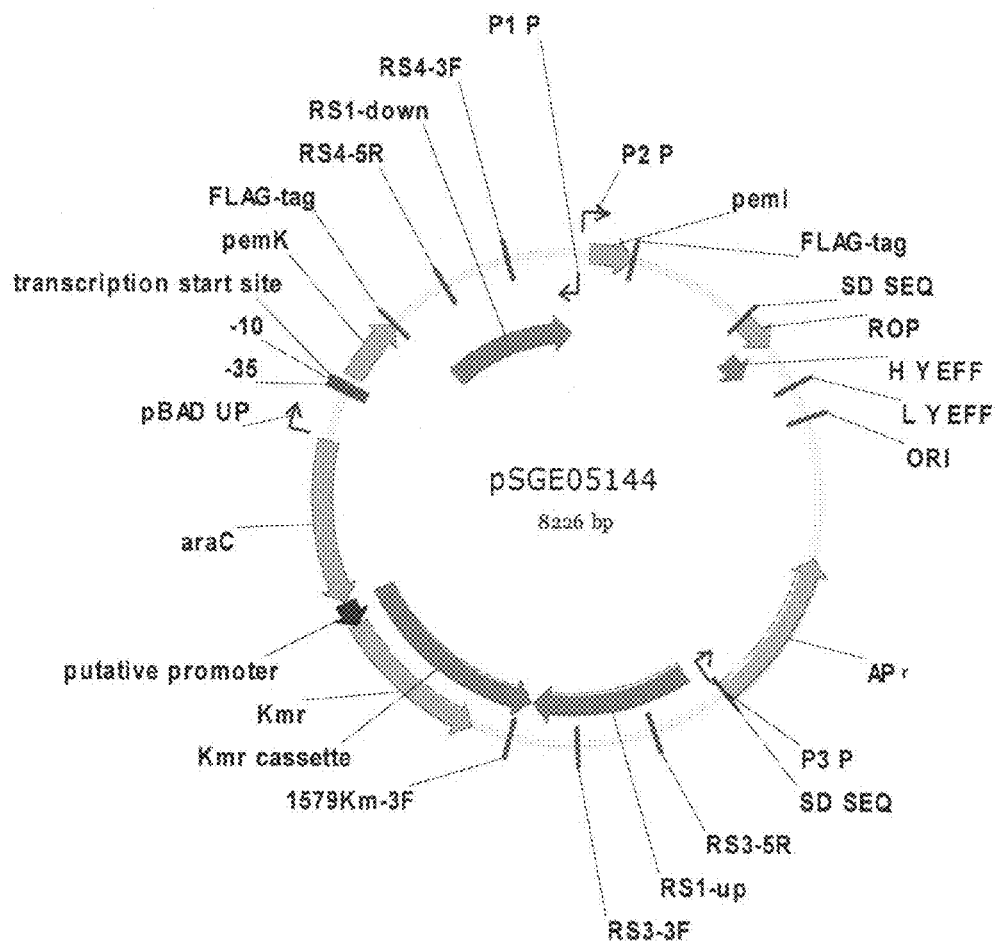
FIG. 3 depicts a vector map of an RS-1 integration vector harboring pARA-pemK and pemI expression cassettes. In this depiction, the pemK toxin gene is in the integrating portion of the vector while the pemI antitoxin gene is in the non-integrating portion of the vector.

Construction of Plasmids:

A vector was designed using the pBR322 backbone joined with two arms comprised of RS-1 homology sequences to the *Synechocystis* PCC 6803 genome. The plasmid was assembled so that the homology arms flanked sequences containing a kanamycin resistance cassette driven by its native promoter (950 bp) and the araC-pARA promoter region (1.2 kb; SEQ ID NO:39) driving expression of the toxin transgene. The corresponding antitoxin gene was provided in the non-integrating portion of the vector. It replaced the tetracycline resistance gene of pBR322, and became linked to the same promoter used to drive the tetracycline resistance gene in pBR322 (SEQ ID NO:55). (See FIG. 3 for a representative plasmid map.) The pemI gene is regulated by the tet promoter. In this scheme, the pemI ORF is used as a cloning tool for amplification of the pemK gene in *E. coli*, and integration into the *Synechocystis* genome only incorporates only the pARA-pemK cassette located between the RS-1 homology arms.

Generation of *Synechocystis* Strains:

Transgenic *Synechocystis* strains were generated by natural transformation protocol. Briefly, log-phase cultures (OD730=0.8) grown in BG-11 medium were harvested and concentrated 10-fold. The cell suspensions (300 uL) were mixed with 800 ug of plasmid DNA and incubated in low light for 5 hrs at 30° C. in the presence on 1% CO2. The cell suspensions were then spread onto a filter on top of a nonselective BG-11 agar plate and allowed to recover overnight at 30° C. in low light. The next day, the filters were transferred to a fresh BG-11 plate containing 20 µg/mL kanamycin, then incubated for an additional 9 days at 30° C. with 1% CO2. After 10 days, colonies were picked from filters and patched onto fresh BG-11 plates with 20 ug/mL kanamycin and allowed to incubate until sufficient biomass accumulated to carry out screening. Clones were identified and selected based on the presence of a gene-specific PCR signal obtained by colony PCR screening using the RedTaq JumpStart mixture (Sigma). Positive clones were used to start liquid BG-11 cultures in the presence of 20 µg/mL kanamycin.

24-Well Plate Assay for Induced Cell Death in *Synechocystis*:

In order to demonstrate inducible cell death and/or growth defects in cyanobacteria, the *Synechocystis* strains transformed with the components of two toxin-antitoxin systems from cyanobacteria and bacteria were assayed for a growth defect phenotype upon the L-arabinose-induced expression of putative cell death genes in a multiwell plate assay.

TABLE 3

List of *Synechocystis* PCC 6803 GMO strains transformed with integration vectors at the RS-1 site with the pARA promoter driving control fluorescent proteins, toxins, or toxin-antitoxin pairs.

| Strain ID | Plasmid ID | Plasmid Description |
|---|---|---|
| PH-SGI-E-0601 | pSGE05152 | pARA-GFP |
| PH-SGI-E-0599 | pSGE05144 | pARA-pemK-FLAG + pTet-pemI |
| PH-SGI-E-0600 | pSGE05151 | pARA-pemK-FLAG (*Microcystis aeruginosa*) |
| PH-SGI-E-0602 | pSGE05153 | pARA-metacaspase 1-FLAG (*Leptolyngbya*) |
| PH-SGI-E-0603 | pSGE05154 | pARA-metacaspase 2-FLAG (*Anabaena*) |
| PH-SGI-E-0604 | pSGE05155 | pARA-metacaspase 3-FLAG (*Synechocystis*) |
| PH-SGI-E-0606 | pSGE05157 | pARA-pemIK (*Microcystis aeruginosa*) |
| PH-SGI-E-0605 | pSGE05156 | pARA-YFP |
| PH-SGI-E-0598 | pSGE05081 | pARA-ccdB-FLAG (*E. coli*) |
| PH-SGI-E-0607 | pSGE05158 | pARA-ccdB-FLAG + pTet-ccdA |

The optical densities of the cultures were measured and the cultures diluted to OD730 of 0.1 in BG-11+H2O, BG-11+1% L-arabinose, or BG-11+2% L-arabinose. All of the cultures tested were incubated in the presence of 20 ug/mL kanamycin and final volume was 1 mL. Cultures were incubated at 30° C. with 1% CO2 with 180 uE of light and shaken at 150 rpm.

Six days after addition of vehicle or L-arabinose, the cultures were inspected by eye and color reduction (chlorosis), indicative of an abnormal reduction in chlorophyll, was scored as indicative of cell death or a growth defect. As expected, strains harboring the pARA-GFP or pARA-YFP expression cassette (PH-SGI-E-0602, PH-SGI-E-0605) did not appear to be negatively affected by addition of L-arabinose or expression of the fluorescent protein. Additionally, the three strains transformed with the three putative cyanobacterial metacaspase genes (PH-SGI-E-0603, plasmid pSGE05153; PH-SGI-E-0603, plasmid pSGE05154; and PH-SGI-E-0604, plasmid pSGEO5155) did not display growth defects in the presence of L-arabinose when scored by eye for chlorosis. However, strains of *Synechocystis* PCC 6803 transformed with either the pemK toxin alone (PH-SGI-E-0600, plasmid pSGEO5151), or with the separated pemK and pemI genes regulated by different promoters (PH-SGI-E-0599, plasmid pSGEO5144), or with the antitoxin-toxin gene pairing of the pemIK operon (PH-SGI-E-0606, plasmid pSGE05157) displayed a phenotype of a lighter green color when scored by eye, with the pemIK operon demonstrating the most dramatic reduction in color. Surprisingly, neither of the strains harboring the ccdB toxin alone or the ccdB+ccdA toxin-antitoxin pair in a similar configuration as plasmid pSGEO5144 (pemK+pemI) displayed any growth defects when L-arabinose was added, even up to 2%. Although expression of ccdB is lethal to *E. coli*, this toxin does not affect the growth of *Synechocystis*.

In addition to the chlorosis observed in the plate, analysis of the samples by microscope on day six revealed a morphological defect in the strain harboring the pARA-pemIK cassette (PH-SGI-E-0606/pSGE05157) that was present in the induced (2% L-arabinose) culture and not observed in the uninduced PH-SGI-E-0606/pSGE05157 samples or the pARA-GFP control strain (PH-SGI-E-0601/pSGE05152) with either treatment. The phenotype observed consisted of a mixed population of cells, with a majority possessing an increase in cell size and an accumulation of cells displaying clusters of three to four cells, whereas the uninduced samples displayed a homogenous distribution of cell size and number. These morphological defects were not observed in any of the control (GFP/YFP), metacaspase, or the ccdB-expressing cells lines, even in the presence of 2% L-arabinose.

Time Course of pemK-Induced Cell Death in *Synechocystis*:

Based on the earlier data described above suggesting expression of the pemK toxin from Microcystis results in the appearance of chlorosis and a presumed growth defect, we chose to carry out a more detailed and quantitative experiment, this time comparing only pemK-containing *Synechocystis* strains (PH-SGI-E-0599/0600/0606) to the fluorescent protein control strain PH-SGI-E-0601 (pARA-GFP). Scaled-up cultures (50 mL) were generated in BG-11 with 20 µg/mL of kanamycin by incubating at 30° C. with 1% CO2, 180 uE of light and shaken at 150 rpm.

TABLE 4

List of *Synechocystis* PCC 6803 GMO strains transformed with integration vectors at the RS-1 site with the pARA promoter driving control fluorescent proteins, toxins, or toxin-antitoxin pairs.

| Strain ID | Plasmid ID | Plasmid Description |
|---|---|---|
| PH-SGI-E-0601 | pSGE05152 | pARA-GFP |
| PH-SGI-E-0599 | pSGE05144 | pARA-pemK + pTet-pemI |
| PH-SGI-E-0600 | pSGE05151 | pARA-pemK |
| PH-SGI-E-0606 | pSGE05157 | pARA-pemIK |

On day 0, the optical densities of the cultures were measured and the cultures diluted to OD730 of 0.3 in BG-11+ H2O or BG-11+2% L-arabinose. All of the cultures tested were incubated in the presence of 20 ug/mL kanamycin and final volume was 50 mL. Cultures were incubated at 30° C. with 1% CO2, 180 uE of light and shaken at 145 rpm. Over the 8 days, the OD730 of the cultures was recorded daily. In addition, cultures were scored for the appearance of chlorosis and on the final day, the Fv/Fm (a measurement of photosynthetic health) was also measured.

Figure 4:
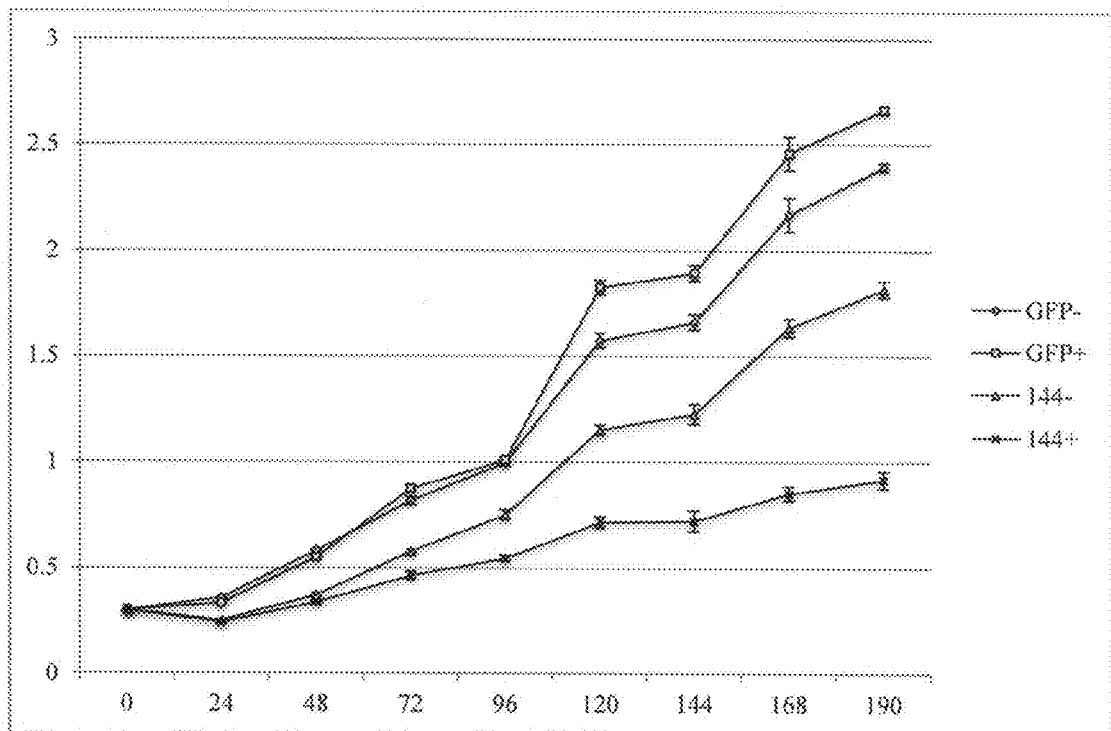
FIG. 4 depicts a graph showing the growth of cultures of PH-SGI-E-0601 (containing pARA-GFP) and PH-SGI-E-0599 (containing pARA-pemK and pTet-pemI) strain isolates noninduced (−) and induced (+) with 2% w/v L-arabinose.
Figure 5:
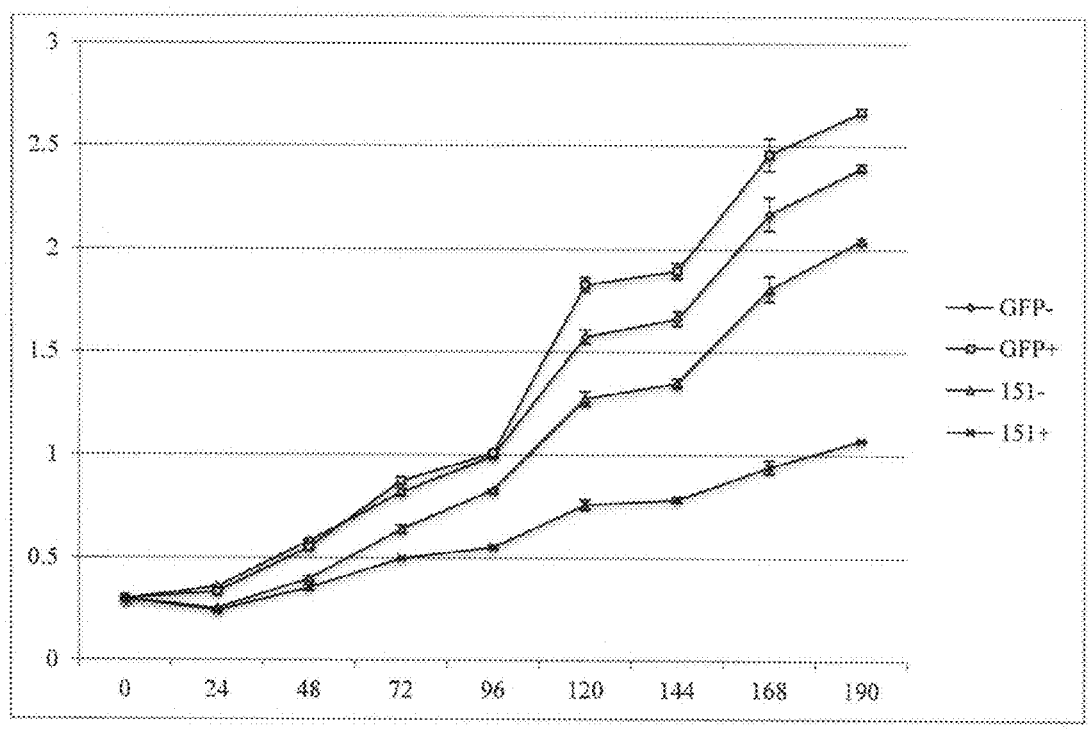
FIG. 5 depicts a graph showing the growth of cultures of the PH-SGI-E-0601 (containing pARA-GFP) and PH-SGI-E-0600 (containing pARA-pemK) strain isolates noninduced (−) and induced (+) with 2% w/v L-arabinose.

The presence of 2% L-arabinose had no negative effect on the PH-SGI-E-0601 control strain when growth is measured by OD730. Although it should be noted that the three pemK cell lines displayed a slower basal growth rate than control cells (potentially due to small levels of toxin expression during uninduced growth), in strains PH-SGI-E-0599 ("144" in FIG. 4) and PH-SGI-E-0600 ("151" in FIG. 5), addition of 2% L-arabinose resulted in a dramatic decrease in cell growth over the course of the experiment when compared to uninduced cultures and control cell lines. In the case of strain PH-SGI-E-0606, there was no difference in growth between induced and uninduced cultures.

Figure 6:
FIG. 6 shows cultures of, from left to right, strain PH-SGI-E-0599, noninduced [dark green]; strain PH-SGI-E-0599 [pale green], induced; strain PH-SGI-E-0600, noninduced [dark green]; strain PH-SGI-E-0600, induced [pale green]; strain PH-SGI-E-0601, noninduced [dark green]; strain PH-SGI-E-0601, induced [dark green]; strain PH-SGI-E-0606, noninduced [moderately green]; and strain PH-SGI-E-0606, induced [moderately green].

Additionally, a change in color (chlorosis) was observed in the L-arabinose induced pemK-expressing strains (PH-SGI-E-0599, -0600, and -0606), with the two strains containing pemK alone in the genome (PH-SGI-E-0599 and -0600) displaying the greatest reduction in coloration (FIG. 6). In this experiment, the pARA-pemIK strain (PH-SGI-E-0606) did not display the same degree of chlorosis as was observed in the 24-well plate experiment; however, this could be due to the different growth conditions employed for the large-scale growth curve experiment (50 mL vs. 1 mL), which potentially induced less stress upon the larger volume cultures over the prolonged period of growth (8 days). The cultures of the control cell line expressing GFP(PH-SGI-E-0601) grew to a dark green color, as expected, and were not negatively affected by the addition of 2% L-arabinose.

Fv/Fm (variable fluorescence divided by maximal fluorescence, e.g., Macedo et al. (2008) Toxicology in Vitro 22: 716-722) was measure to assess the photosynthetic capacity, an indicator for the photosynthetic "health" of the cells. As shown in the Table 5 below, the Fv/Fm measurements taken on the last day of the experiment indicate the pemK-engineered strains are photosynthetically impaired as compared to controls when pemK expression is induced with 2% L-arabinose.

TABLE 5

Fv/Fm values for *Synechocystis* PCC 6803 strains expressing of pemK toxin in response to arabinose induction (+) or not induced (−) for pemK toxin expression.

| | Strain | | | | | | | |
|---|---|---|---|---|---|---|---|---|
| | 0599− | 0599+ | 0600− | 0600+ | 0601− | 0601+ | 0606− | 0606+ |
| Fv/Fm | 0.369 | 0.08 | 0.414 | 0.102 | 0.429 | 0.444 | 0.238 | 0.218 |

The data show that the control strain PH-SGI-E-0601 gave the highest Fv/Fm yield and did not display a significant difference in Fv/Fm in the absence or presence of 2% L-arabinose (0.429 vs. 0.444, Table 5). In contrast, the two strains that showed a growth defect when treated with 2% L-arabinose, PH-SGI-E-0599 and PH-SGI-E-0600, which included the pemK toxin gene operably linked to the arabinose-inducible promoter, displayed slightly lower Fv/Fm yields (0.369 and 0.414) when not induced, but when treated with arabinose, the measured Fv/Fm values were 0.080 and 0.102, a dramatic decrease from uninduced cultures of the same strain. These data indicates the color loss observed in induced cultures is indeed chlorosis and that the general health, as well as photosynthetic capabilities of the cyanobacteria, is greatly compromised upon triggered expression of pemK in these strains, although, in accordance with OD and visual examination, there was no difference between induced and uninduced cultures.

PH-SGI-E-0606, which inducibly expressed the pemI antitoxin in addition to the pemK toxin, did not lose photosynthetic capability upon induction of these genes, indicating the protective effect of the antitoxin when expressed from the same promoter as the toxin gene.

Example 5

Cultivation of a Eukaryotic Alga Under Nutrient Deplete and Nutrient Replete Conditions A *Nannochloropsis gaditana* strain isolated from a culture obtained from the CCMP culture collection (CCMP1894) was grown under nutrient replete conditions as well as under nitrogen and phosphate limitation to identify genes whose transcripts were elevated under nutrient starvation with respect to nutrient replete conditions and vice versa. Three hundred mL cultures were grown in 500 mL shake flasks at 125 rpm on an orbital shaker under a (16 h light:8 h dark) diel cycle, using 90-100 µE constant light and 1% $CO_2$ at 25° C. Light intensity was measured using LI-COR Light Meter, LI-250A. Standard nutrient replete media was prepared by dissolving 35 g of Instant Ocean salts (Aquatic Eco Systems, Apopka, Fla.), 5.71 mL of a 1.75M $NaNO_3$ stock solution, and 5.41 mL of a 77 mM $K_2HPO_4.3H_2O$ stock solution in 981 mL of milliQ filtered water to make 1 liter. The solution was filter sterilized by passage through a 0.2 micron bottle top filter (Corning #430513). On the day of use, a stock vitamin mix and chelated trace metal stock solution was added and the media was mixed by shaking. The vitamin mix included 0.01% thiamine HCl, 0.37 µM cyanocobalamin, and 0.41 µM biotin. The chelated trace metal solution included 11.71 mM disodium EDTA, 11.65 mM $FeCl_3$, 39.2 µM $CuSO_4$, 77.5 µM $ZnSO_4$, 42 µm $CoCl_2$, 91 µM $MnCl_2$, and 26 µM $Na_2MoO_4$. Nitrogen-free media used the same recipe but lacked $NaNO_3$ solution, while phosphate-free media used the same recipe but lacked the $K_2HPO_4$ solution.

Example 6

Identification of Promoter Sequences

Transcript profiling was used to identify novel promoter and terminator regulatory regions. The *N. gaditana* strain was grown separately in nitrogen deplete, phosphate deplete, and nutrient replete culture media, and total RNA was collected approximately 6 hours after the onset of the experiment, as well as at noon on Day 1 and Day 2 (approximately 24 hours and 48 hours after the onset of the experiment).

RNA samples were sequenced by Ambry Genetics (Aliso Viejo, Calif.) after poly-A purification and fragmentation. mRNA was sequenced using sequencing-by-synthesis (Illumina HiSeq) to generate 100 bp paired-end reads using the mRNA-Seq procedure (described in Mortazavi et al. (2008) *Nature Methods* 5:621-628. Mappable reads were aligned to the *N. gaditana* reference genome sequence using CLC Genomics Workbench software. Expression levels were computed for every annotated gene normalized for gene length and total number of mappable reads per sample, and reported in FPKM units for every sample. FPKM is a measure of relative transcriptional levels that normalizes for differences in transcript length. Expression levels in FPKM were calculated for every gene and each condition using standard parameters allowing for reads to map up to 50 bp upstream and downstream from every gene.

For expression of toxin genes, Nannochloropsis transcripts were identified having a low or negligible level of expression under nutrient replete conditions and a high level of expression under conditions of nitrogen depletion and/or phosphate depletion (Table 6). These transcripts were mapped to the Nannochloropsis and sequences extending up to 1000 base pairs upstream of the presumed initiating ATG were identified as putative promoter-containing sequences. For example, the 5' upstream region of the AMT family ammonium or ammonia transporter gene (SEQ ID NO:56), the 5' upstream region of the ammonium transporter Rh type B gene (SEQ ID NO:57), the 5' upstream region of the copper amine oxidase/domain 3 gene (SEQ ID NO:58), the 5' upstream region of the plasma membrane Na+/H+ antiporter gene (SEQ ID NO:59), the 5' upstream region of the E3 ubiquitin-protein ligase ARI5 gene (SEQ ID NO:60), or the 5' upstream region of the NAD(P)-binding Rossmann-like domain gene (SEQ ID NO:61), or subfragments of any of these 5' regions having promoter activity that is induced by nitrogen depletion are candidate regulatory sequences that may be cloned upstream of a toxin gene such that the toxin gene can be expressed when a microorganism encounters nitrogen limitation, for example, when a microorganism such as a eukaryotic alga escapes from a growth area where nutrients such as nitrogen are replete. The 5' upstream region of the phosphate-repressible phosphate permease-like protein (SEQ ID NO:65) or a subfragment thereof is another sequence that can be used for expression of a toxin protein. In this case the toxin would be expressed when the escaped microorganisms, e.g., algae, experience phosphate limitation.

In order to identify promoters for use in heterologous expression of antitoxin genes, Nannochloropsis transcripts were also identified having a high level of expression under nutrient replete conditions and a lower or negligible level of expression under conditions of nitrogen depletion or phosphorus depletion (Table 6). For example, the 5' upstream region of the alpha/beta fold hydrolase (SEQ ID NO:62), the 5' upstream region of the hydroxylamine reductase 1 (SEQ ID NO:63), and the 5' upstream region of the ferredoxin component (SEQ ID NO:64), or subfragments of any of these 5' regions having promoter activity under nutrient replete conditions, and preferably lower activity under nitrogen and/or phosphate depletion are candidate regulatory sequences that may be cloned upstream of an antitoxin gene such that the antitoxin gene can be expressed when a microorganism such as a eukaryotic alga is cultured in a growth area where nutrients such as nitrogen are replete, but preferably is not expressed or expressed at a low level when the microorganism encounters nitrogen or phosphate limitation.

TABLE 6

Genes Differentially Expressed under Nutrient Limitation in *Nannochloropsis*

| Translation description | Replete 16 h | Replete 32 h | N minus, 16 h | N minus, 32 h | P minus, 16 h | P minus, 32 h | Upstream Genomic Sequence |
|---|---|---|---|---|---|---|---|
| AMT family ammonium or ammonia transporter | 68 | 32 | 375 | 646 | 66 | 43 | SEQ ID NO: 56 |
| Ammonium transporter Rh type B | 33 | 31 | 151 | 240 | 40 | 25 | SEQ ID NO: 57 |
| Copper amine oxidase/Domain 3 | 6 | 3 | 33 | 35 | 6 | 3 | SEQ ID NO: 58 |
| Plasma membrane Na+/H+ antiporter | 7 | 5 | 39 | 52 | 9 | 6 | SEQ ID NO: 59 |
| E3 ubiquitin-protein ligase ARI5 | 2 | 6 | 23 | 25 | 6 | 8 | SEQ ID NO: 60 |
| NAD(P)-binding Rossmann-like Domain | 19 | 3 | 20 | 24 | 2 | 3 | SEQ ID NO: 61 |
| Alpha/beta fold hydrolase | 24 | 23 | 7 | 9 | 36 | 28 | SEQ ID NO: 62 |
| Hydroxylamine reductase 1 | 104 | 108 | 15 | 12 | 125 | 140 | SEQ ID NO: 63 |
| Ferredoxin component | 24 | 105 | 1 | 1 | 6 | 11 | SEQ ID NO: 64 |
| Phosphate-repressible Phosphate Permease-like protein | 15 | 13 | 12 | 17 | 40 | 38 | SEQ ID NO: 65 |

Example 7

Vector Constructions and Transformation

Vectors for transformation can be constructed by in vitro recombination using Gibson's cloning method (Gibson et al. (2009) *Nat. Methods* 6:343-345) using PCR fragments treated with exonuclease to expose overlapping sequences, or by standard cloning techniques. The Simian virus 40 (SV40) promoter-5'-UTR and 3'-UTR-terminator sequences can be used to control expression of the ble gene encoding Zeocin resistance, to form an SV40-ble selectable marker in the transformation vector.

Vectors including an antitoxin gene operably linked to a promoter region regulating expression under nutrient replete conditions (e.g., SEQ ID NO:62, SEQ ID NO:63, or SEQ ID NO:64, or an active subfragment of any thereof) can be transformed into *Nannochloropsis gaditana* by linearizing the DNA with restriction endonucleases and purifying the digested DNA by phenol-chloroform extraction. A logarithmic-stage culture of *Nannochloropsis gaditana* is prepared for transformation by washing the cells three times with 384 mM sorbitol and resuspending in 384 mM sorbitol at $1 \times 10^{10}$ cells/mL. 100 ul of the washed cells are mixed thoroughly with 5 μg of linearized plasmid DNA in an ice-chilled 2 mm electroporation cuvette. The electroporation can be performed with BioRad GenePulser set at 50 μF capacitance, 500Ω resistance, 2.2 kV. After electroporation, 1 mL of 384 mM sorbitol is added and cells are transferred to 10 mL of PM024 media. The culture is incubated at 25° C. overnight in dim light (5 uE/m$^2$/s). $5 \times 10^8$ cells are then spread onto nutrient replete agar media in 80 mm polystyrene petri dishes with 5 μg/mL Zeocin. The cells are incubated at room temperature under constant light (70-80 μE/m$^2$/s) for three weeks. Transformants are patched on nutrient replete agar with 5 μg/mL Zeocin. Liquid suspension cultures can be grown in nutrient replete media with 5 μg/mL Zeocin.

Strains transformed with the antitoxin gene are not expected to display any growth defects. These strains can then be transformed with constructs that include a toxin gene cognate to the antitoxin gene that is operably linked to a promoter region regulating expression under nutrient deplete conditions (e.g., SEQ ID NO:56, SEQ ID NO:57, SEQ ID NO:58, SEQ ID NO:59, SEQ ID NO:60, or SEQ ID NO:65, or an active subfragment of any thereof).

For example, a eukaryotic algal species, such as, for example, an alga of a species of *Nannochloropsis, Chlamydomonas, Chlorella, Tetraselmis, Cyclotella*, or another eukaryotic algal species can be transformed with the *E. coli* pemI antitoxin gene (SEQ ID NO:71; protein sequence SEQ ID NO:72) operably linked to the 5' upstream region of the alpha/beta fold hydrolase (SEQ ID NO:62), or an active fragment thereof, or the promoter of an orthologous gene of the host species, such that the pemI antitoxin is expressed under nutrient replete condtions, but turned off under nitrogen depletion. The Nannochloropsis strain that includes the alpha/beta fold hydrolase promoter-pemI antitoxin gene construct can subsequently be transformed with a construct that includes the *E. coli* pemK toxin gene having a sequence altered to eliminate pemK endonuclease target sites (SEQ ID NO:74; protein sequence SEQ ID NO:75) operably linked to the 5' upstream region of the plasma membrane Na+/H+ antiporter gene (SEQ ID NO:59) or an active fragment thereof or the promoter of an orthologous gene of the host species, such that the pemK toxin gene is expressed under conditions of nitrogen limitation. The Nannochloropsis strain that includes the alpha/beta fold hydrolase promoter-pemI antitoxin gene construct and the plasma membrane Na+/H+ antiporter promoter-toxin insensitive pemK gene construct is engineered for biocontainment, such that the strain is protected against potential effects of leaky expression of the toxin gene under nitrogen replete conditions, but has sustained expression of the toxin gene when it experiences nutrient limitation if it escapes the cultivation area.

In another example, a *Nannochoropsis* strain can be transformed with the *E. coli* MazE antitoxin gene (SEQ ID NO:66; protein sequence SEQ ID NO:67) operably linked to the 5' upstream region of the ferredoxin component (SEQ ID NO:64), or an active fragment thereof, such that the pemI antitoxin is expressed under nutrient replete conditions, but turned off under nitrogen or phosphate depletion. The *Nannochloropsis* strain that includes the ferredoxin component promoter-MazE antitoxin gene construct can subsequently be transformed with a construct that includes the *E. coli* MazF toxin gene having a sequence altered to eliminate MazF endonuclease target sites (SEQ ID NO:69; protein sequence SEQ ID NO:70) operably linked to the 5' upstream region of the copper amine oxidase/domain 3 gene (SEQ ID NO:58) or an active fragment thereof. The *Nannochloropsis* strain that includes the ferredoxin component promoter-MazE antitoxin gene construct and the copper amine oxidase/domain 3 promoter-toxin insensitive MazF gene construct is engineered for biocontainment, such that the strain is protected against potential effects of leaky expression of the toxin gene under nutrient replete conditions, but has sustained expression of the toxin gene when it experiences nutrient limitation if it escapes the cultivation area.

In a further example, the *Nannochloropis* strain described immediately above transformed for biocontainment using the MazE gene and engineered MazF gene can be further transformed with the *E. coli* dinJ antitoxin gene (SEQ ID NO:76; protein sequence SEQ ID NO:77) operably linked to the 5' upstream region of the ferredoxin component (SEQ ID NO:64), or an active fragment thereof, such that the dinJ antitoxin is expressed under nutrient replete condtions, but turned off under nitrogen depletion. The Nannochloropsis strain that includes the exogenous MazE and MazF genes described above and the ferredoxin component promoter-dinJ antitoxin gene construct, can subsequently be transformed with a construct that includes the *E. coli* YafQ toxin gene having a sequence altered to eliminate both YafQ and MazF endonuclease target sites (SEQ ID NO:79; protein sequence SEQ ID NO:80) operably linked to the 5' upstream region of the plasma membrane Na+/H+ antiporter gene (SEQ ID NO:59) or an active fragment thereof, such that both the MazF and YafQ toxin genes are expressed under conditions of nitrogen limitation. The Nannochloropsis strain that includes the ferredoxin component promoter-dinJ antitoxin gene construct, the ferredoxin component promoter-MazE antitoxin gene construct, the copper amine oxidase/domain 3 promoter-toxin insensitive MazF gene construct and the plasma membrane Na+/H+ antiporter promoter-double toxin insensitive YafQ gene construct is engineered for biocontainment, such that the strain is protected against potential effects of leaky expression of the toxin genes under nitrogen replete conditions, but has sustained expression of the toxin gene when it experiences nutrient limitation if it escapes the cultivation area.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the term "or" as used in a phrase such as "A or B" herein is intended to include "A and B", "A or B", "A", and "B". The singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entireties.

What is claimed is:

1. A recombinant microorganism genetically engineered for controlled biocontainment, wherein the microorganism comprises two or more genes that each encode an exogenous Type II toxin having ribonuclease activity, wherein each gene is operably linked to a regulatable promoter, and wherein each gene is modified to exclude at least one endonuclease target site of the toxin.

2. The recombinant microorganism of claim 1, wherein each Type II toxin gene encodes a toxin of CcdB toxin family, RelE toxin family, MazF toxin family, ParE toxin family, PIN toxin family, AhaI toxin family, MNT toxin family, Doc toxin family, VapC toxin family, zeta toxin family, HipA toxin family, or HigB toxin family.

3. The recombinant microorganism of claim 2, wherein each Type II toxin gene encodes a RelE, MazF, ParE, PIN, AhaI, MNT, Doc, pemK, VapC, zeta, HipA, HigB, ChpI, StbE, YafQ, or YoeB toxin.

4. The recombinant microorganism of claim 1, wherein the regulatable promoter is regulated by light, temperature, pH, a compound or nutrient present in or absent from the media, or a combination thereof.

5. The recombinant microorganism of claim 4, wherein the regulatable promoter is responsive to a compound or nutrient present in or absent from the media.

6. The recombinant microorganism of claim 5, wherein the regulatable promoter is regulated by a sugar, an organic acid, a fatty acid, an amino acid, a lipid, a hydrocarbon, phosphate, nitrate, ammonium, nitrogen, sulfur, carbon dioxide, a metal, a quorum-sensing compound, a phenolic compound, a flavonoid, a protein or peptide, or any combination thereof.

7. The recombinant microorganism of claim 1, wherein the microorganism further comprises a gene encoding an antitoxin cognate to at least one of the Type II toxins.

8. The recombinant microorganism of claim 7, wherein the gene encoding an antitoxin cognate is operably linked to a promoter that is not regulated by or is regulated oppositely by the compound or nutrient present in or absent from the media that regulates the promoter operably linked to the corresponding Type II toxin gene.

9. The recombinant microorganism of claim 8, wherein the regulatable promoter operably linked to the Type II toxin gene is regulated by depletion of a nutrient from the growth media or environment of the microorganism.

10. The recombinant microorganism of claim 9, wherein the regulatable promoter operably linked to the Type II toxin gene is regulated by depletion of one or more of nitrogen, phosphate, sulfur, iron, copper, or $CO_2$ from the growth media or environment of the microorganism.

11. The recombinant microorganism of claim 1, wherein the microorganism is a photosynthetic microorganism.

12. The recombinant microorganism of claim 11, wherein the photosynthetic microorganism is a eukaryotic microalga.

13. The recombinant microorganism of claim 12, wherein the eukaryotic microalga is a species of *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Picochlorum, Platymonas, Pleurochrysis, Pleurococcus, Prototheca, Pseudochlorella, Pseudoneochloris, Pyramimonas, Pyrobotrys, Scenedesmus, Schizochlamydella, Skeletonema, Spyrogyra, Stichococcus, Tetrachorella, Tetraselmis, Thalassiosira, Viridiella*, or *Volvox*.

14. The recombinant microorganism of claim 11, wherein the photosynthetic microorganism is a cyanobacterium.

15. The recombinant microorganism of claim 14, wherein the cyanobacterium is an *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, The rmosynechocystis, Tolypothrix, Trichodesmium, Tychonema*, or *Xenococcus* species.

16. The recombinant microorganism of claim 14, wherein the recombinant cyanobacterium further comprises an exogenous gene encoding an antitoxin cognate to at least one of the Type II toxins.

17. The recombinant cyanobacterium of claim 14, wherein at least one of the Type II toxin genes is homologous with respect to the cyanobacterium.

18. The recombinant cyanobacterium of claim 14, wherein the recombinant cyanobacterium comprises an endogenous gene encoding an antitoxin cognate to at least one of the Type II toxins.

19. The recombinant cyanobacterium of claim 18, wherein the antitoxin gene encodes an antitoxin of Re1B antitoxin family, MazE antitoxin family, ParD antitoxin family, RHH antitoxin family, ArsR antitoxin family, HEPN antitoxin family, Phd antitoxin family, VapB antitoxin family, epsilon antitoxin family, HipB antitoxin family or HigA antitoxin family.

20. The recombinant cyanobacterium of claim 19, wherein the antitoxin gene encodes an Axe, CcdA, RelB, MazE, ParD, RHH, ArsR, HEPN, PemI, Kis, yfaN, stbD, dinJ, yoeM, PIN, Phd, VapB, epsilon, HipB or HigA antitoxin.

21. The recombinant microorganism of claim 1, wherein at least two of the Type II toxin genes are each operably linked to a different regulatable promoter, wherein each regulatable promoter is regulated by a different compound or environmental condition.

22. The recombinant microorganism of claim 21, wherein each regulatable promoter is regulated by depletion of a different nutrient.

23. The recombinant microorganism of claim 1, wherein at least one of the two or more Type II toxin genes is engineered to be insensitive to at least two of the toxins encoded by the two or more Type II toxin genes.

24. A recombinant microorganism genetically engineered for controlled biocontainment, wherein the microorganism comprises two or more genes that each encode an exogenous means for cleaving RNA, wherein each gene is operably linked to a means for regulating gene expression, and wherein each gene is modified to exclude at least one endonuclease target site of the RNA cleavage means.

* * * * *